US009416406B2

(12) United States Patent
Kuersten

(10) Patent No.: US 9,416,406 B2
(45) Date of Patent: *Aug. 16, 2016

(54) AMPLIFICATION AND DETECTION OF RIBONUCLEIC ACIDS

(71) Applicant: APPLIED BIOSYSTEM, LLC, Carlsbad, CA (US)

(72) Inventor: R. Scott Kuersten, Fitchburg, WI (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/571,142

(22) Filed: Dec. 15, 2014

(65) Prior Publication Data

US 2015/0099268 A1 Apr. 9, 2015

Related U.S. Application Data

(63) Continuation of application No. 13/960,780, filed on Aug. 6, 2013, now Pat. No. 8,932,816, which is a continuation of application No. 13/463,758, filed on May 3, 2012, now abandoned, which is a continuation of application No. 12/835,869, filed on Jul. 14, 2010, now Pat. No. 8,192,941, which is a continuation of application No. PCT/US2009/030822, filed on Jan. 13, 2009.

(60) Provisional application No. 61/020,913, filed on Jan. 14, 2008, provisional application No. 61/034,833, filed on Mar. 7, 2008, provisional application No. 61/039,460, filed on Mar. 26, 2008, provisional application No. 61/047,549, filed on Apr. 24, 2008.

(51) Int. Cl.
*C12P 19/34* (2006.01)
*C12Q 1/68* (2006.01)
*C12N 15/10* (2006.01)

(52) U.S. Cl.
CPC .......... *C12Q 1/6855* (2013.01); *C12N 15/1096* (2013.01)

(58) Field of Classification Search
USPC ...................................... 435/6.12, 91.1, 91.2
See application file for complete search history.

(56) References Cited

U.S. PATENT DOCUMENTS

| 5,185,243 | A | 2/1993 | Ullman et al. |
| 6,013,445 | A | 1/2000 | Albrecht et al. |
| 6,506,561 | B1 | 1/2003 | Cheval et al. |
| 6,511,810 | B2 | 1/2003 | Bi et al. |
| 6,797,470 | B2 | 9/2004 | Barany et al. |
| 6,806,049 | B1 | 10/2004 | Maekawa et al. |
| 7,153,658 | B2 | 12/2006 | Andersen et al. |
| 8,192,941 | B2 | 6/2012 | Kuersten |
| 2003/0119004 | A1 | 6/2003 | Wenz et al. |
| 2004/0219565 | A1 | 11/2004 | Kauppinen et al. |
| 2005/0272075 | A1 | 12/2005 | Jacobsen et al. |
| 2006/0003337 | A1 | 1/2006 | Brandis et al. |
| 2006/0051789 | A1 | 3/2006 | Kazakov et al. |
| 2006/0063181 | A1 | 3/2006 | Green et al. |
| 2006/0211000 | A1 | 9/2006 | Sorge et al. |
| 2006/0246464 | A1 | 11/2006 | Xia |
| 2007/0009944 | A1 | 1/2007 | Bowater et al. |
| 2007/0015187 | A1 | 1/2007 | Lao et al. |
| 2007/0020644 | A1 | 1/2007 | Kolykhalov et al. |
| 2008/0070238 | A1 | 3/2008 | Klussmann et al. |
| 2010/0029511 | A1 | 2/2010 | Raymond et al. |
| 2010/0297728 | A1 | 11/2010 | Ziman et al. |

FOREIGN PATENT DOCUMENTS

| EP | 0320308 | 6/1989 |
| WO | WO-90/01069 | 2/1990 |
| WO | WO-03/093504 | 11/2003 |
| WO | WO-2006/033020 | 3/2006 |
| WO | WO-2007/044066 | 4/2007 |
| WO | WO-2007/050990 | 5/2007 |
| WO | WO-2009/091719 | 7/2009 |
| WO | WO-2010/048605 | 4/2010 |
| WO | WO-2010/094040 | 8/2010 |

OTHER PUBLICATIONS

Ambros, et al., "MicroRNAs and Other Tiny Enfogenous RNAs in C. elegans", *Current Biology*, vol. 13, Issue 10, May 13, 2003, 807-818.

Applied Biosystems, "miRNA Discovery and Profiling with the SOLiD Small RNA Expression Kit", 2008, 1-4.

Applied Biosystems, "Whole Genome Analysis of Small RNA", 2008, 1-6.

Aravin, et al., "Identification and characterization of small RNAs involved in RNA silencing", *FEBS Letters*, vol. 579, No. 26, Oct. 31, 2005, 5830-5840.

Armour, et al., "Digital transcriptome profiling using selective hexamer priming for cDNA synthesis", *Nature Methods*, vol. 6, No. 9, Sep. 1, 2009, 647-649.

Bentwich, et al., "Identification of hundreds of conserved and nonconserved human micro RNAs", *Nature Genetics*, vol. 37, No. 7, Jun. 19, 2005, 766-770.

(Continued)

*Primary Examiner* — Kenneth Horlick

(57) ABSTRACT

Compositions, methods, and kits for detecting one or more species of RNA molecules are disclosed. In one embodiment, a first adaptor and a second adaptor are ligated to the RNA molecule using a polypeptide comprising double-strand specific RNA ligase activity, without an intervening purification step. The ligated product is reverse transcribed, then at least some of the ribonucleosides in the reverse transcription product are removed. Primers are added and amplified products are generated. In certain embodiments, the sequence of at least part of at least one species of amplified product is determined and at least part of the corresponding RNA molecule is determined. In some embodiments, at least some of the amplified product species are detected, directly or indirectly, allowing the presence and/or quantity of the RNA molecule of interest to be determined.

16 Claims, 16 Drawing Sheets

(56) References Cited

OTHER PUBLICATIONS

Figure 1:
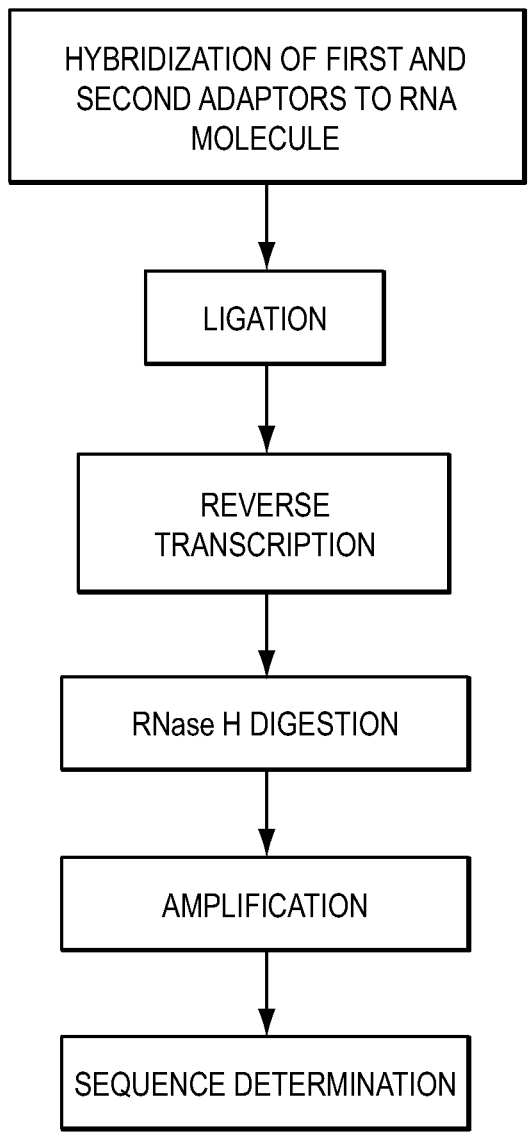

Berezikov, et al., "Approaches to microRNA discovery", *Nature Genetics Supplement*, vol. 38, Supplemental, Jun. 2006, 2-7.

Berezikov, et al., "Diversity of microRNAs in human and chimpanzee brain", *Nature Genetics*, vol. 38, No. 12, Dec. 2006, 1375-1377.

Berezikov, et al., "Many novel mammalian microRNA candidates identified by extensive cloning and RAKE analysis", *Genome Research*, vol. 16, No. 10, Oct. 2006, 1289-1298.

Biodynamics Laboratory Inc., "DynaExpress miRNA Cloning Kit AV", Code No. DS300AV, www.biodynamics.co.jp, prior to Jan. 13, 2009, 1-25.

Brennecke, et al., "Towards a Complete Description of the microRNA Complement of Animal Genomes", *Genome Biology*, vol. 4, No. 9, 2003, 228.1-228.3.

Brenner, et al., "Gene expression analysis by massively parallel signature sequencing (MPSS) on microbead arrays", *Nature Biotechnology*, vol. 18, No. 6, Jun. 2000, 630-634.

Brown, et al., "Targeted display: a new technique for the analysis of differential gene expression", *Methods in Enzymology*, vol. 303, Jan. 1, 1999, 392-408.

Caetano-Anolles, et al.,"DNA amplification fingerprinting using very short arbitrary oligonucleotide primers", *BioTechnology*, vol. 9, No. 6, Jun. 1, 1991, 553-557.

Carthew, "A New RNA Dimension to Genome Control", *Science*, vol. 313, No. 5785, Jul. 21, 2006, 305-306.

Cheung, et al., "Whole genome amplification using a degenerate oligonucleotide primer allows hundreds of genotypes to be performed on less than one nanogram of genomic DNA",*Proceedings of the National Academy of Sciences*, vol. 93, No. 25, Dec. 10, 1996, 14676-14679.

Consalez, et al., "A computer-driven approach to PCR-based differential screening, alternative to differential display", *BioInformatics*, vol. 15, No. 2, Feb. 1, 1999, 93-105.

Cruz-Reyes, et al., "Distinct Functions of Two RNA Ligases in Active Trypanosoma brucei RNA Editing Complexes", *Molecular and Cellular Biology*, vol. 22, No. 13, 2002, 4652-4660.

Cummins, et al., "The colorectal microRNAome", *Proceedings of the National Academy of Sciences*, vol. 103, No. 10, Mar. 7, 2006, 3687-3692.

Eddy, "Non-Coding RNA Genera and the Modern RNA World", *Nature Reviews Genetics*, vol. 2, Dec. 1, 2001, 919-929.

Elbashir, S., et al., "RNA Interference is Mediated by 21- and 22-nucleotide RNAs", *Genes & Development*, vol. 15, 2001, 188-200.

Fahlgren, et al., "High-Throughput Sequencing of Arabidopsis microRNAs: Evidence for Frequent Birth and Death of MIRNA Genes", *PLoS ONE*, Issue 2; e219, 2007, 1-14.

Fu, et al., "Identification of human fetal liver miRNAs by a novel method", *FEBS Letters*, vol. 579, No. 17, Jul. 4, 2005, 3849-3854.

Gao, et al., "Functional complementation of Trypanosoma brucei RNA in vitro editing with recombinant RNA ligase", *Proceedings of the National Academy of Sciences*, vol. 102, No. 13, Mar. 29, 2005, 4712-4717.

Gumport, et al., "T4 RNA Ligase as a Nucleic Acid Synthesis and Modification Reagent in Gene Amplification and Analysis", *Gene Amplification and Analysis*, vol. 2, 1981, 313-345.

Hamalainen, et al., "Major interference from Leukocytes in Reverse transcription-PCR identified as Neurotoxin Ribonuclease from Eosinophils: Detection of Residual Chronic Myelogenous Leukemia from Cell Lysates by Use of an Eosinophil-depleted Cell Preparation", *Clinical Chemistry*, vol. 45, No. 4, Apr. 1999, 465-471.

Hannon, et al., "The Expanding Universe of Noncoding RNAs", *Cold Spring Harbor Symposia on Quantitative Biology*, vol. LXXI, 2006, 551-564.

Ho, et al., "Bacteriophage T4 RNA ligase 2 (gp24.1) exemplifies a family of RNA ligases found in all phylogenetic domains", *Proceedings of the National Academy of Sciences*, vol. 99, No. 20, 2002, 12709-12714.

Ho, et al., "Structure and Mechanism of RNA Ligase", *Structure*, Vo. 12, 2004, 327-339.

Hutvagner, , "Small RNA asymmetry in RNAi: Function in RISC assembly and gene regulation", *FEBS Letters*, vol. 579, 2005, 5850-5857.

Illumina, Inc., "Preparing Samples for Analysis of Small RNA", Part # 11251913 Rev. A, 2007, 1-22.

Kim, et al., "Identification of many microRNAs that copurify with polyribosomes in mammalian neurons", *Proceedings of the National Academy of Sciences*, vol. 101, No. 1, 2004, 360-365.

Kim, et al., "Octamer-based genome scanning distinguishes a unique subpopulation of *Escherichia coli* 0157 :H7 strains in cattle", *Proceedings of the National Academy of Sciences*, vol. 96, No. 23, 1999, 13288-13293.

Kling, "Ultrafast DNA sequencing", *Nature Biotechnology*, vol. 21, No. 12, 2003, 1425-1427.

Lagos-Quintana, et al., "Identification of Novel Genes Coding for Small Expressed RNAs", *Science*, vol. 294, 2001, 853-858.

Lagos-Quintana, et al., "Identification of Tissue-Specific MicroRNAs from Mouse", *Current Biology*, vol. 12, No. 9, 2002, 735-739.

Lagos-Quintana, et al., "New microRNAs from mouse and human", *RNA*, vol. 9, No. 2, Feb. 2003, 175-179.

Lau, et al., "An Abundant Class of Tiny RNAs with Probable Regulatory Roles in Caenorhabditis elegans", *Science*, vol. 294, No. 5543, Oct. 26, 2001, 858-862.

Lau, et al., "Characterization of the piRNA Complex from Rat Testes", *Science*, vol. 313, No. 5785, Jul. 21, 2006, 363-367.

Lee, et al., "An Extensive Class of Small RNAs in Caenorhabditis elegans", *Science*, vol. 294, No. 5543, Oct. 26, 2001, 862-864.

Lindahl, et al., "Mammalian DNA Ligases", *Annual Reviews Biochemistry*, vol. 61, Jul. 1992, 251-281.

Lopez-Nieto, et al., "Selective amplification of protein-coding regions of large sets of genes using statistically designed primer sets", *Nature Biotechnology*, vol. 14, No. 7, Jul. 1, 1996, 857-861.

Lu, et al., "Elucidation of the Small RNA Component of the Transcriptome", *Science*, vol. 309, No. 5740, Sep. 2, 2005, 1567-1569.

Lu, et al., "MicroRNAs and other small RNAs enriched in the Arabidopsis RNA-dependent RNA polymerase-2 mutant", *Genome Research*, vol. 16, No. 10, Sep. 5, 2006, 1276-1288.

Margulies, et al., "Genome sequencing in microfabricated high-density picolitre reactors", *Nature*, vol. 437 (15), Jul. 31, 2005, 376-380.

Maroney, et al., "DIrect detection of small RNAs using splinted ligation", *Nature Protocols*, vol. 3, No. 2, 2008, 279-287.

Mattick, et al., "Non-coding RNA", *Human Molecular Genetics*, vol. 15, Review Issue 1, 2006, R17-R29.

McManus, et al., "Identification of candidate mitochondrial RNA editing ligases from Trypanosoma brucei", *RNA*, vol. 7, No. 2, Feb. 2001, 167-175.

Michael, "Cloning MicroRNAs From Mammalian Tissues", *Methods in Molecular Biology*, vol. 342, 2006, 189-207.

Mishima, et al., "RT-PCR-based analysis of microRNA (miR-1 and -124) expression in mouse CNS", *Brain Research*, vol. 1131, Feb. 2, 2007, 37-43.

Nandakumar, et al., "Dual Mechanisms whereby a Broken RNA End Assists the Catalysis of Its Repair by T4 RNA Ligase 2", *Journal of Biological Chemistry*, vol. 280, No. 25, Jun. 24, 2005, 23484-23489.

Nandakumar, et al., "How an RNA Ligase Discriminates RNA versus DNA Damage", *Molecular Cell*, vol. 16, No. 2, Oct. 22, 2004, 211-221.

Nandakumar, et al., "RNA Substrate Specificity and Structure-guided Mutational Analysis of Bacteriophage T4 RNA Ligase 2", *Journal of Biological Chemistry*, vol. 279, No. 30, Jul. 23, 2004, 31337-31347.

Omoto, et al., "Cloning and Detection of HIV-1 Encoded MicroRNA", *Methods in Molecular Biology*, vol. 342, 2006, 255-265.

PCT/US2009/030822, International Preliminary Report on Patentability mailed Jul. 29, 2010.

PCT/US2009/030822, PCT International Search Report with Written Opinion mailed, Jul. 6, 2009.

Pesole, et al., "GeneUp: a program to select short PCR primer pairs that occur in multiple members of sequence lists", *Biotechniques*, vol. 25, No. 1, Jul. 1, 1998, 112-123.

(56) References Cited

OTHER PUBLICATIONS

Prasanth, et al., "Eukaryotic regulatory RNAs: an answer to the 'genome complexity' conundrum", *Genes & Development*, vol. 21, No. 1, Jan. 1, 2007, 11-42.
Reinartz, et al., "Massively parallel signature sequencing (MPSS) as a tool for in-depth quantitative gene expression profiling in all organisms", *Briefing in Functional Genomics and Proteomics*, vol. 1, No. 1, 2002, 95-104.
Ro, et al., "A PCR-based Method for Detection and Quantification of small RNAs", *Biochem Biophys Res Commun.*, vol. 351, No. 3, Dec. 22, 2006, 756-763.
Ro, et al., "Cloning and expression profiling of small RNAs expressed in the mouse ovary", *RNA*, vol. 13, No. 12, Dec. 13, 2007, 2366-2380.
Ro, et al., "Cloning and expression profiling of testis-expressed piRNA-like RNAs", *RNA*, vol. 13, No. 10, Oct. 2007, 1693-1702
Roche Applied Science, "Genome Sequencer 20 System", 2005, 1-20.
Ruby, et al., "Large-Scale Sequencing Reveals 21U-RNAs and Additional MicroRNAs and Endogenous siRNAs in C. elegans", *Cell*, vol. 127, No. 6, Dec. 15, 2006, 1193-1207.
Rusche, et al., "The Two RNA Ligases of the Trypanosoma brucei RNA Editing Complex: Cloning the Essential Band IV Gene and Identifying the Band V Gene", *Molecular and Cellular Biology*, vol. 21, No. 4, Feb. 2001, 979-989.
Schnaufer, et al., "An RNA Ligase Essential for RNA Editing and Survival of the Bloodstream Form of Trypanosoma brucei", *Science*, vol. 291, No. 5511, Mar. 16, 2001, 2159-2162.
Silva, et al., "Generation of longer 3' cDNA fragments from massively parallel signature sequencing tags", *Nucleic Acids Research*, vol. 32, No. 12, 2004, 1-7.
Stahlberg, et al., "Properties of the reverse transcription reaction in mRNA quantification", *Clinical Chemistry*, vol. 50, No. 3, Mar. 1, 2004, 509-515.
System Biosciences, "Global MicroRNA Amplification Kit", Cat. # RA400A-1: User Manual (ver. 3-06090), 2006, 1-16.
System Biosciences, "MicroRNA Discovery Kit", Cat. # RA410A-1; User Manual (ver. 3-061101, 2006, 1-24.
System Biosciences, "Pre-Made MicroRNA-Enriched cDNAs", Cat # RA500A-1-RA509A-1; User Manual, XP002524777, 2006, 1-20.
Takada, et al., "Profiling of microRNA expression by mRAP", *Nature Protocols*, vol. 2, No. 12, Jan. 1, 2007, 3136-3145.
Tomkinson, et al., "DNA Ligases: Structure, Reaction Mechanism, and Function", *Chem. Rev.*, vol. 106, No. 2, Feb. 2006, 687-699.
Vater, et al., "Short bioactive Spiegelmers to migraine-associated calcitonin gene-related peptide rapidly identified by a novel approach: tailored-SELEX", *Nucleic Acids Research*, vol. 31, No. 21, Nov. 1, 2003, e130.
Wong, et al., "Use of Tagged Random Hexamer Amplification (TRHA) to Clone and Sequence Minute Quantities of DNA—Application to a 180 kb Plasmid Isolated from Sphingomonas F199", *Nucleic Acids Research*, vol. 24, No. 19, 1996, 3778-3783.
Wood, et al., "RNA Ligase: Picking Up the Pieces", *Molecular Cell*, vol. 13, No. 4, 2004, 455-456.
Yin, et al., "Characterization of bacteriophage KVP40 and T4 RNA ligase 2", *Virology*, vol. 319, No. 1, Feb. 5, 2004, 141-151.
Yin, et al., "Structure-Function Analysis of T4 RNA Ligase 2", *Journal of Biological Chemistry*, vol. 278, No. 20, May 16, 2003, 17601-17608.
Zhang, et al., "Differential priming of RNA templates during cDNA synthesis markedly affects both accuracy and reproducibility of quantitative competitive reverse-transcriptase PCR", *Biochemical Journal*, vol. 337, No. 2, Jan. 15, 1999, 231-241.

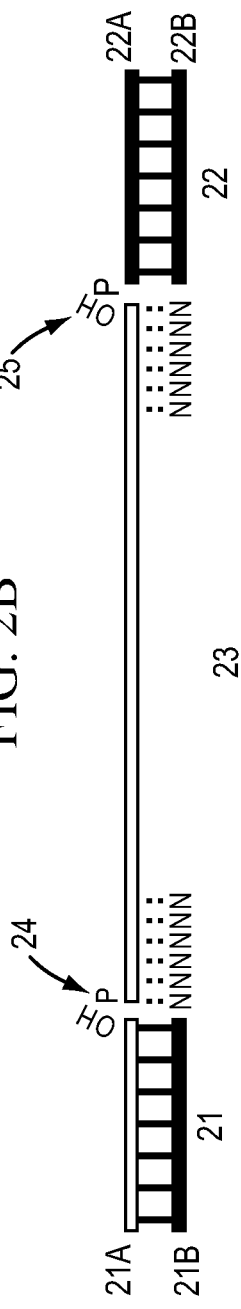
FIG. 2A
FIG. 2B

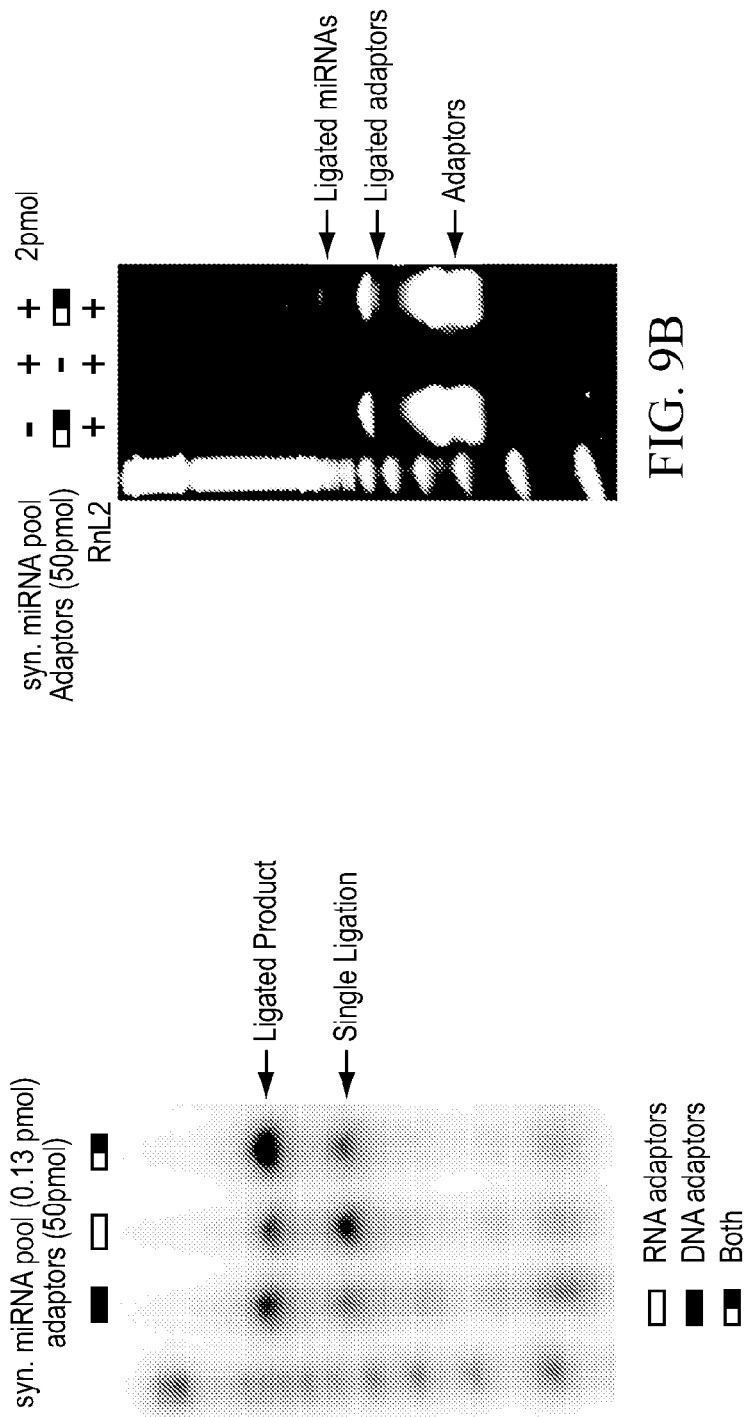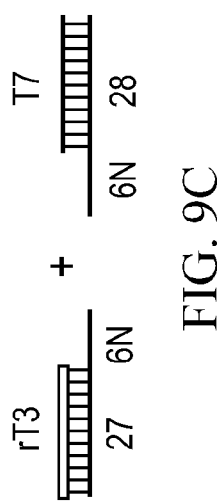
FIG. 9A
FIG. 9B
FIG. 9C

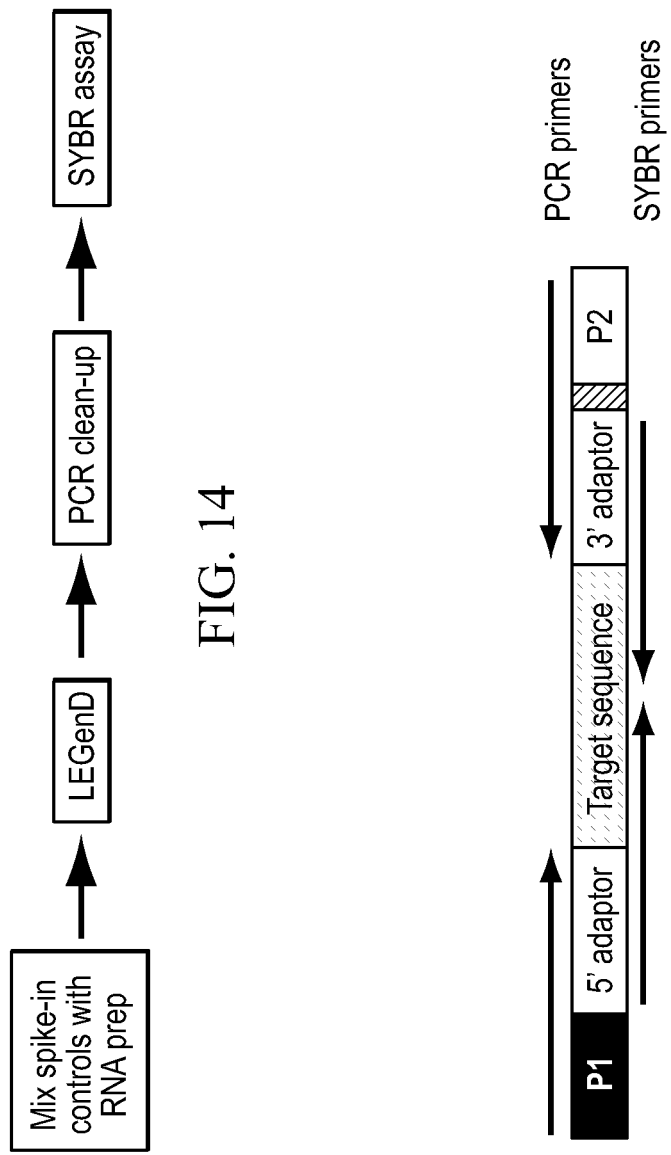

AMPLIFICATION AND DETECTION OF RIBONUCLEIC ACIDS

CROSS-RELATED APPLICATIONS

This application is a Continuation of U.S. application Ser. No. 13/960,780, filed on Aug. 6, 2013, now U.S. Pat. No. 8,932,816, which issued Jan. 13, 2015; which is a Continuation of U.S. application Ser. No. 13/463,758, filed on May 3, 2012 and now Abandoned; which is a Continuation of U.S. application Ser. No. 12/835,869, filed on Jul. 14, 2010 (now U.S. Pat. No. 8,192,941, which issued on Jun. 5, 2012); which is a Continuation of, and claims priority to, International Patent Application No. PCT/US2009/030822, having an international filing date of Jan. 13, 2009; which application claims the benefit of U.S. Provisional Application Nos. 61/020,913, filed on Jan. 14, 2008; 61/034,833, filed on Mar. 7, 2008; 61/039,460, filed on Mar. 26, 2008; and 61/047,549, filed on Apr. 24, 2008. Each application is incorporated by reference herein in its entirety.

FIELD

The present teachings generally relate to methods, reagents, and kits for detecting, amplifying, and quantifying ribonucleic acid (RNA), including but not limited to coding RNA and non-coding RNA (ncRNA).

INTRODUCTION

Analysis of genome expression patterns provides valuable insight into the role of differential expression in a wide variety of biological processes, including but not limited to, various disease states. Such analysis, whether mRNA-based gene expression or small non-coding RNA-based expression analysis, is becoming a rapidly expanding avenue of investigation in many disciplines in the biological sciences. Small non-coding RNA discovery is also an area of great scientific and medical interest. It is believed that by knowing what parts of the genome are transcribed when and why, a better understanding of many complex and inter-related biological processes may be obtained.

Small non-coding RNAs are rapidly emerging as significant effectors of gene regulation in a multitude of organisms spanning the evolutionary spectrum. Animals, plants and fungi contain several distinct classes of small RNAs; including without limitation, miRNAs, siRNAs, piRNAs, and rasiRNAs. These tiny gene expression modulators typically fall within the size range of ~18-40 nt in length, however their effect on cellular processes is profound. They have been shown to play critical roles in developmental timing and cell fate mechanisms, tumor progression, neurogenesis, transposon silencing, viral defense and many more. They function in gene regulation by binding to their targets and negatively effecting gene expression by a variety of mechanisms including heterochromatin modification, translational inhibition, mRNA decay and even nascent peptide turnover mechanisms. Therefore, identification of the small RNAs in a given sample can greatly facilitate gene expression analysis.

Some small RNAs are produced from defined locations within the genome. MicroRNAs are such a class; they are typically transcribed by RNA polymerase II from polycistronic gene clusters or can also be generated from pre-mRNA introns. Thus far several thousand unique miRNA sequences are known. Other classes of small RNAs, such as piRNAs or endogenous siRNA, are not typically transcribed from a defined locus in the genome. Instead, they are generated in response to events such as viral infections or retrotransposon expression and serve to silence these 'foreign' sequences that would otherwise result in serious detriment to the cell. Descriptions of ncRNA can be found in, among other places, Eddy, Nat. Rev. Genet. 2:919-29, 2001; Mattick and Makunin, Human Mol. Genet. 15:R17-29, 2006; Hannon et al., Cold Springs Harbor Sympos. Quant. Biol. LXXI:551-64, 2006. Sequencing the entire population of small RNAs in a sample provides a direct method to identify and even profile all classes of these RNAs at one time.

SUMMARY

The present teachings are directed to methods, reagents, and kits for detecting and quantitating: (i) small RNA molecules, also referred to as untranslated functional RNA, non-coding RNA (ncRNA), and small non-messenger RNA (snmRNA); and (ii) coding RNA, which may or may not be fragmented and/or fractionated by methods known in the art.

According to certain disclosed methods, a ligation reaction composition is formed comprising at least one RNA molecule to be detected, at least one first adaptor, at least one second adaptor, and a double-strand specific RNA ligase. The first adaptor comprises a first oligonucleotide comprising at least two ribonucleosides on the 3'-end and a second oligonucleotide that comprises a single-stranded portion when the first oligonucleotide and the second oligonucleotide are hybridized together. The second adaptor comprises a third oligonucleotide that comprises a 5' phosphate group and a fourth oligonucleotide that comprises a single-stranded portion when the third oligonucleotide and the fourth oligonucleotide are hybridized together. A first adaptor and a second adaptor are ligated to an RNA molecule in the ligation reaction composition by the double-strand specific RNA ligase to form a ligated product. The first adaptor and the second adaptor anneal with the RNA molecule in a directional manner due to their structure and each adaptor is ligated simultaneously or nearly simultaneously to the RNA molecule with which it is annealed, rather than sequentially (for example, when a second adaptor and the RNA molecule are combined with a ligase and the second adaptor is ligated to the 3' end of the RNA molecule, then subsequently a first adaptor is combined with the ligated RNA molecule-second adaptor and the first adaptor is then ligated to the 5' end of the RNA molecule-second adaptor, with an intervening purification step between ligating the second adaptor to the RNA molecule and ligating the first adaptor to the RNA molecule, see, e.g., Elbashir et al, Genes and Development 15: 188-200, 2001; Berezikov et al., Nat. Genet. Supp. 38: S2-S7, 2006). It is to be appreciated that the order in which components are added to the ligation reaction composition is not limiting and that the components may be added in any order. It is also to be appreciated that during the process of adding components, an adaptor may be ligated with a corresponding RNA molecule in the presence of a ligase before all of the components of the reaction composition are added, for example but without limitation, a second adaptor may be ligated with a corresponding RNA molecule in the presence of a ligase before the first adaptors are added, and that such reactions are within the intended scope of the current teachings, provided there is not a purification procedure between the time one adaptor is ligated to the RNA molecule and the time the other adaptor is ligated to the RNA molecule. An RNA-directed DNA polymerase (sometimes referred to as an RNA-dependent DNA polymerase) is combined with the ligated product to form reaction mixture, which is incubated under conditions suitable for a reverse transcribed product. The reverse transcribed product is combined with a ribonuclease, typically ribonuclease H (RNase H), and at least some of the ribonucleosides are digested from the reverse transcribed product to form an amplification template.

The amplification template is combined with at least one forward primer, at least one reverse primer, and a DNA-directed DNA polymerase (sometimes referred to as a DNA-dependent DNA polymerase) to form an amplification reaction composition. The amplification reaction composition is thermocycled under conditions suitable to allow amplified products to be generated. In some embodiments, at least one species of amplified product is detected. In some embodiments, a reporter probe and/or a nucleic acid dye is used to indirectly detect the presence of at least one of the RNA species in the sample. In certain embodiments, an amplification reaction composition further comprises a reporter probe, for example but not limited to a TaqMan® probe, molecular beacon, Scorpion™ primer or the like, or a nucleic acid dye, for example but not limited to, SYBR® Green or other nucleic acid binding dye or nucleic acid intercalating dye. In certain embodiments of the current teachings, detecting comprises a real-time or end-point detection technique, including without limitation, quantitative PCR. In some embodiments, the sequence of at least part of the amplified product is determined, which allows the corresponding RNA molecule to be identified. In some embodiments, a library of amplified products comprising a library-specific nucleotide sequence is generated from the RNA molecules in a starting material, wherein at least some of the amplified product species share a library-specific identifier, for example but not limited to a library-specific nucleotide sequence, including without limitation, a barcode sequence or a hybridization tag, or a common marker or affinity tag. In some embodiments, two or more libraries are combined and analyzed, then the results are deconvoluted based on the library-specific identifier.

According to certain disclosed methods, only one polymerase, a DNA polymerase comprising both DNA-directed DNA polymerase activity and RNA-directed DNA polymerase activity, is employed in the reverse transcription reaction composition and no additional polymerase is used. In other method embodiments, both an RNA-directed DNA polymerase and a DNA-directed DNA polymerase are added to the reverse transcription reaction composition and no additional polymerase is added to the amplification reaction composition.

In some embodiments, a method for detecting a RNA molecule in a sample comprises combining the sample with at least one first adaptor, at least one second adaptor, and a polypeptide comprising double-strand specific RNA ligase activity to form a ligation reaction composition in which the at least one first adaptor and the at least one second adaptor are ligated to the RNA molecule of the sample to form a ligated product in the same ligation reaction composition, and detecting the RNA molecule of the ligated product or a surrogate thereof. In some embodiments, the at least one first adaptor comprises a first oligonucleotide having a length of 10 to 60 nucleotides and comprising at least two ribonucleosides on the 3'-end, and a second oligonucleotide comprising a nucleotide sequence substantially complementary to the first oligonucleotide and further comprising a single-stranded 5' portion of 1 to 8 nucleotides when the first oligonucleotide and the second oligonucleotide are duplexed. In some embodiments, the at least one second adaptor comprises a third oligonucleotide having a length of 10 to 60 nucleotides and comprising a 5' phosphate group, and a fourth oligonucleotide comprising a nucleotide sequence substantially complementary to the third oligonucleotide and further comprising a single-stranded 3' portion of 1 to 8 nucleotides when the third oligonucleotide and the fourth oligonucleotide are duplexed. In some embodiments, the single-stranded portions independently have a degenerate nucleotide sequence, or a sequence that is complementary to a portion of the RNA molecule. In some embodiments, the first and third oligonucleotides have a different nucleotide sequence. In the ligation reaction composition, the RNA molecule to be detected hybridizes with the single-stranded portion of the at least one first adaptor and the single-stranded portion of the at least one second adaptor.

In some embodiments, detecting the RNA molecule or a surrogate thereof comprises combining the ligated product with i) a RNA-directed DNA polymerase, ii) a DNA polymerase comprising DNA dependent DNA polymerase activity and RNA dependent DNA polymerase activity, or iii) a RNA-directed DNA polymerase and a DNA-directed DNA polymerase; reverse transcribing the ligated product to form a reverse transcribed product; digesting at least some of the ribonucleosides from the reverse transcribed product with ribonuclease H to form an amplification template; combining the amplification template with at least one forward primer, at least one reverse primer, and a DNA-directed DNA polymerase when the ligated product is combined as in i), to form an amplification reaction composition; cycling the amplification reaction composition to form at least one amplified product, and determining the sequence of at least part of the amplified product, thereby detecting the RNA molecule.

In some embodiments, a method for generating an RNA library comprises combining a multiplicity of different RNA molecules with a multiplicity of first adaptor species, a multiplicity of second adaptor species, and a double-strand specific RNA ligase to form a ligation reaction composition, wherein the at least one first adaptor comprises a first oligonucleotide comprising at least two ribonucleosides on the 3'-end and a second oligonucleotide that comprises a single-stranded portion when the first oligonucleotide and the second oligonucleotide are hybridized together, and wherein the at least one second adaptor comprises a third oligonucleotide that comprises a 5' phosphate group and a fourth oligonucleotide that comprises a single-stranded portion when the third oligonucleotide and the fourth oligonucleotide are hybridized together and ligating the at least one first adaptor and the at least one second adaptor to the RNA molecule to form a multiplicity of different ligated product species, wherein the first adaptor and the second adaptor are ligated to the RNA molecule in the same ligation reaction composition. The method further comprises combining the multiplicity of ligated product species with an RNA-directed DNA polymerase, reverse transcribing at least some of the multiplicity of ligated product species to form a multiplicity of reverse transcribed product species, digesting at least some of the ribonucleosides from at least some of the multiplicity of reverse transcribed products with a ribonuclease H (RNase H) to form a multiplicity of amplification template species, combining the multiplicity of amplification template species with at least one forward primer, at least one reverse primer, and a DNA-directed DNA polymerase to form an amplification reaction composition, and cycling the amplification reaction composition to form a library comprising a multiplicity of amplified product species, wherein at least some of the amplified product species comprise an identification sequence that is common to at least some of the other amplified product species in the library.

Kits for performing certain of the instant methods are also disclosed. These and other features of the present teachings are set forth herein.

DRAWINGS

The skilled artisan will understand that the drawings, described below, are for illustration purposes only. These figures are not intended to limit the scope of the present teachings in any way.

FIG. 1 provides a schematic overview of various exemplary method embodiments of the current teachings.

FIG. 2A-FIG. 2B: FIG. 2A schematically depicts an exemplary first adaptor 21 and an exemplary second adaptor 22; FIG. 2B schematically depicts the exemplary first and second adaptors shown in FIG. 1A directionally annealed to an exemplary RNA molecule 23. The ligation junction for the first adaptor 21 and the 5' end of the RNA molecule 23 is shown by arrow 24 and the ligation junction for the second adaptor 22 and the 3' end of the RNA molecule 23 is shown by arrow 25. Open rectangles depict RNA sequence such as for 21A and 23. Horizontal solid lines depict DNA sequence such as for 21B and 22A.

Figure 3:
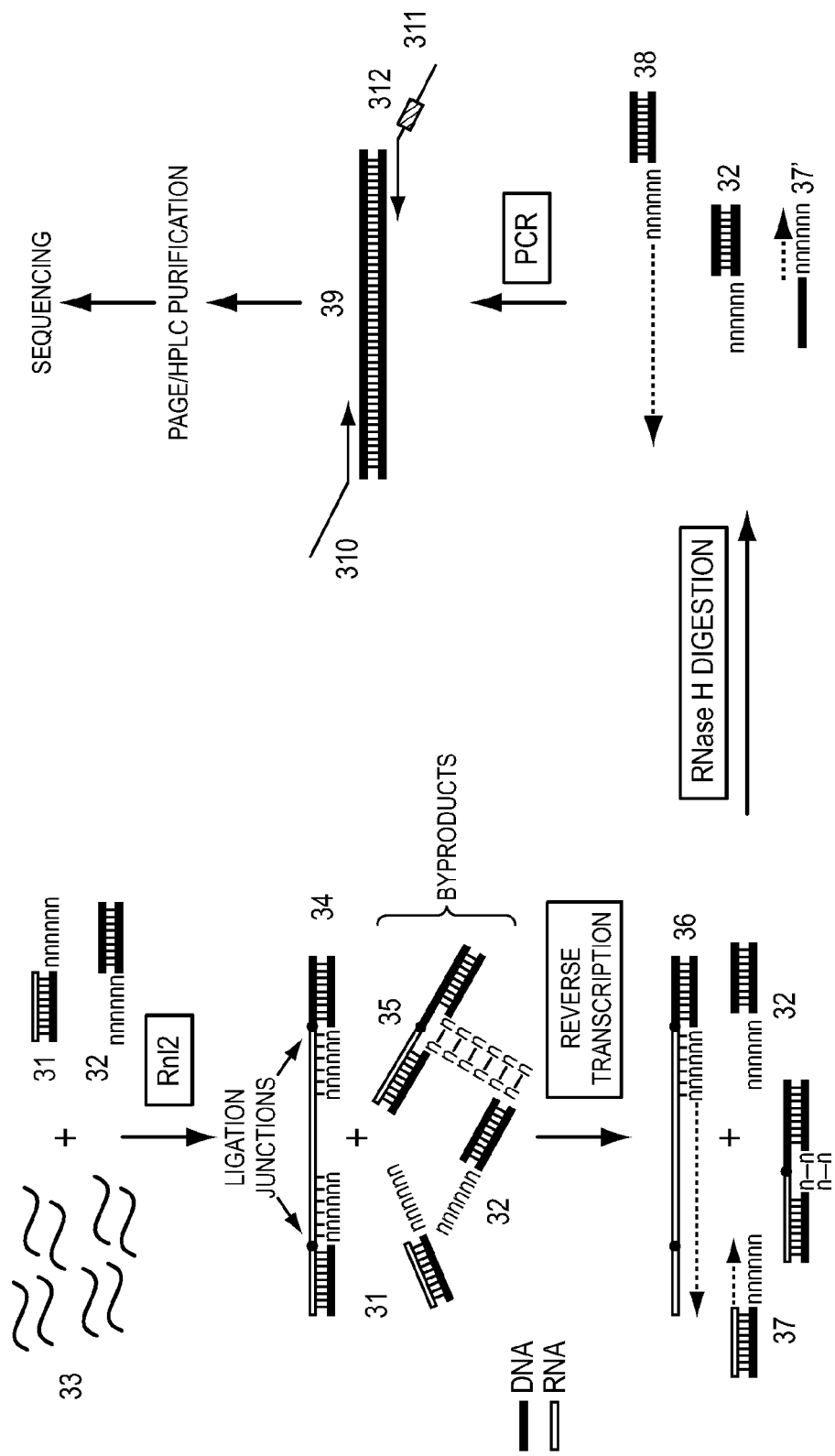

FIG. 3 provides a schematic overview of an exemplary embodiment of the current teachings. A population of small RNA molecules 33 is combined with a first adaptor 31 and a second adaptor 32 and Rnl2 ligase to form ligated product 34. Unannealed adaptors and/or undesired annealed byproduct molecules 35 may also be present in the ligated reaction composition. The reaction composition is combined with an RNA-directed DNA polymerase to generate reverse transcribed product 36, which composition is then combined with ribonuclease H to generate amplification template 38. The amplification template 38 is combined with a DNA-directed DNA polymerase, a forward primer 310 and a reverse primer 311 to form an amplification reaction composition. In this illustrative embodiment, the reverse primer further comprises an identification sequence 312, sometimes referred to as a "bar code" sequence.

Figure 4:
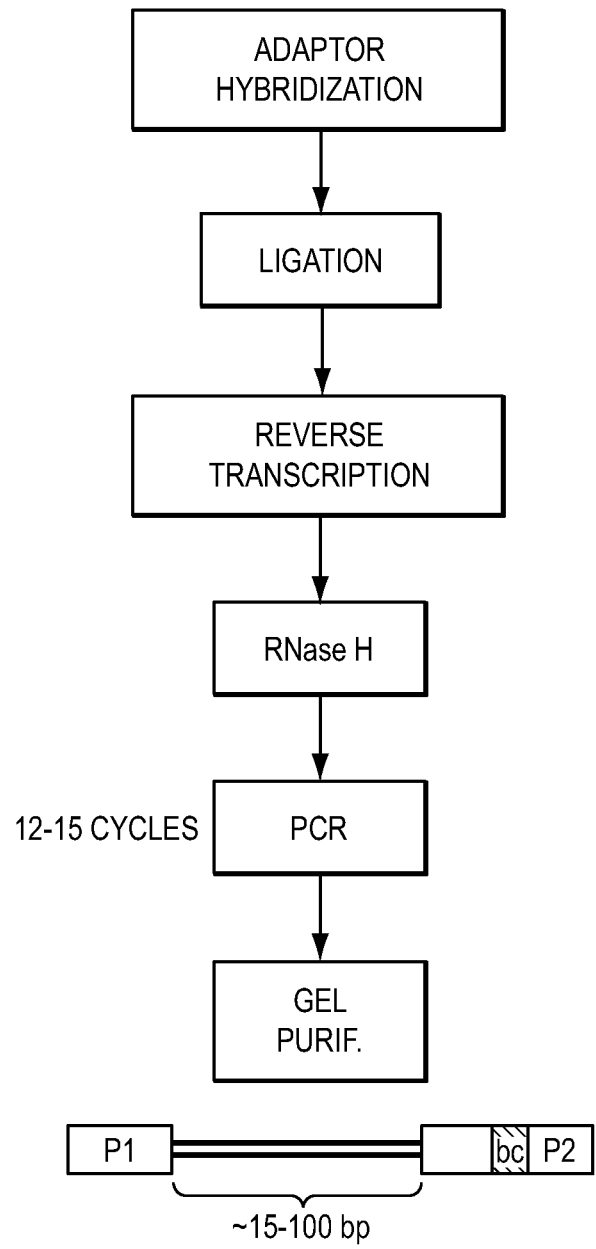

FIG. 4 provides a schematic overview of an exemplary embodiment of the current teachings. In this illustrative embodiment, the amplified product is gel purified (Gel Purif.) and comprises an insert sequence (shown by a curved bracket in FIG. 4), a first primer region (shown as P1 in FIG. 4), and a second primer region (shown as P2 in FIG. 4) that includes a bar code or identification sequence (shown as be in FIG. 4).

Figure 5:
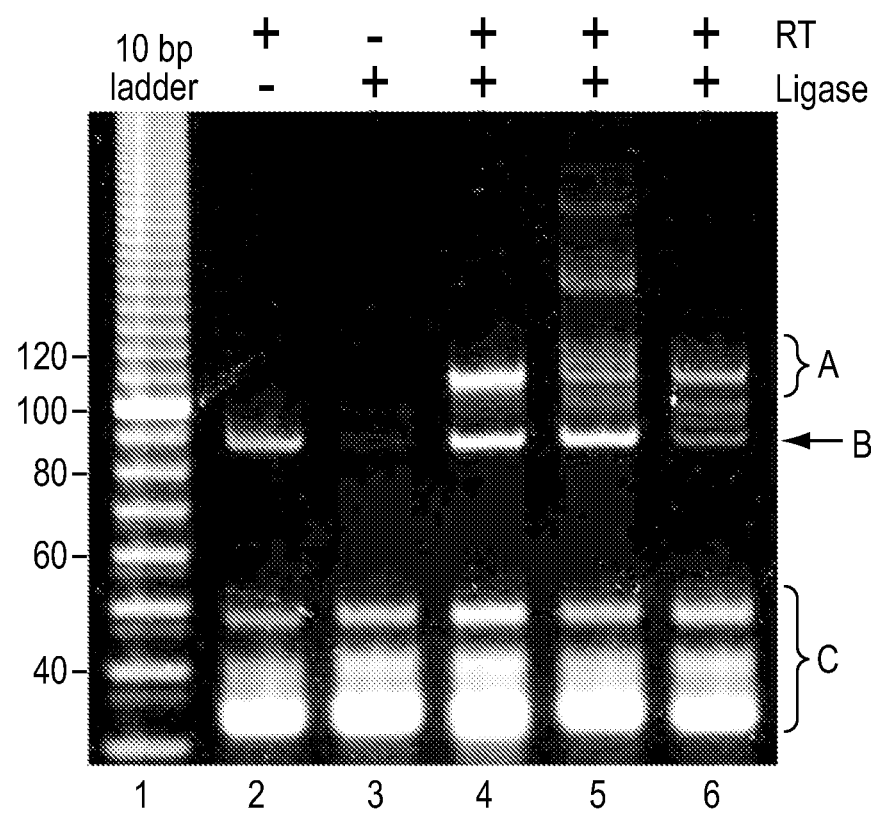

FIG. 5 depicts an electropherogram of the exemplary amplified products generated as described in Example 1.

Lane 1: 10 bp DNA ladder (100 ng; Invitrogen P/N 10821-015, Carlsbad, Calif.);
Lane 2: starting material was 100 ng total RNA, minus ligase control;
Lane 3: starting material was 100 ng total RNA, minus RT control;
Lane 4: starting material was 100 fmol mirVana™ Reference Panel v. 9.1 (Applied Biosystems P/N 4388891, Foster City, Calif.);
Lane 5: starting material was 100 ng total RNA; and
Lane 6: starting material was flashPAGE™ Fractionator System-purified RNA from 5 µg total RNA.

Figure 6:
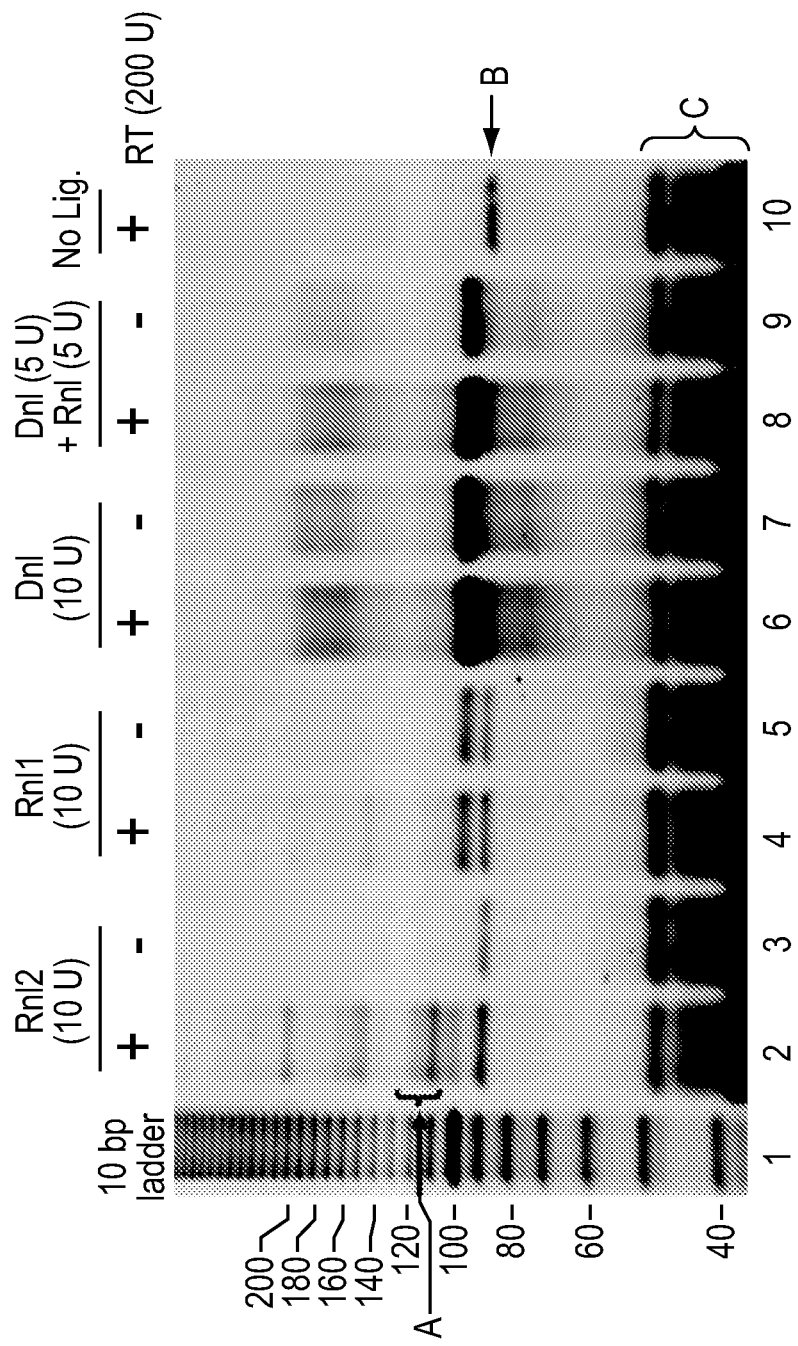

FIG. 6 depicts an electropherogram of the exemplary amplified products generated using various double strand-dependent ligases, alone or in combination, as described in Example 2.

Lane 1: 100 ng 10 bp DNA ladder (Invitrogen);
Lane 2: 10 units of bacteriophage T4 RNA ligase 2, 200 U reverse transcriptase (RT);
Lane 3: 10 units of bacteriophage T4 RNA ligase 2, no RT;
Lane 4: 10 units bacteriophage T4 RNA ligase I, 200 U RT;
Lane 5: 10 units bacteriophage T4 RNA ligase 1, no RT;
Lane 6: 10 units bacteriophage T4 DNA ligase, 200 U RT;
Lane 7: 10 units bacteriophage T4 DNA ligase, no RT;
Lane 8: 5 units each of bacteriophage T4 RNA ligase I and bacteriophage T4 DNA ligase, 200 U RT;
Lane 9: 5 units each of bacteriophage T4 RNA ligase I and bacteriophage T4 DNA ligase, no RT; and
Lane 10: no ligase, 200 U RT.

Figure 7A:
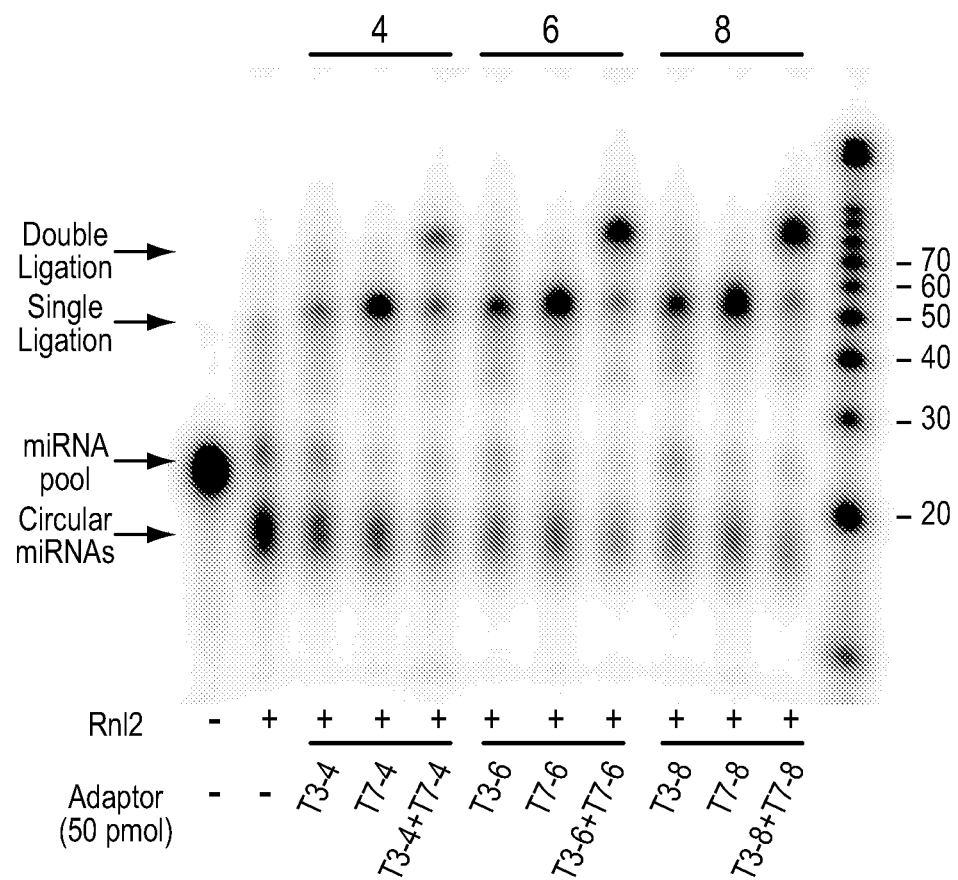

FIG. 7A depicts an electropherogram of exemplary ligated products (shown by arrow annotated double ligation) generated in a ligation reaction composition comprising various first adaptors, various second adaptors, or combinations of various first adaptors and various second adaptors, with a multiplicity of different miRNA molecules comprised of approximately equimolar concentrations of about five hundred different species of synthetic miRNA molecules and RNA ligase 2 of bacteriophage T4, as described in Example 4. The numbers 4, 6, and 8 across the top of FIG. 7A correspond to the number of degenerate nucleotide sequences on the second oligonucleotide of each of the first adaptors and the fourth oligonucleotide of each of the second adaptors in the reaction composition (shown as N in FIG. 7B).

X-axis:

T3-4 indicates that the corresponding ligation products were generated in a ligation composition comprising only first adaptors comprising the structure T3:27 N (see FIG. 7B), where in this case N equals 4 degenerate nucleotides;

T3-6 indicates that the corresponding ligation products were generated in a ligation reaction composition containing only first adaptors comprising the structure T3:27 N, where N in this case equals 6 degenerate nucleotides;

T3-8 indicates that the corresponding ligation products were generated in a ligation reaction containing only first adaptors comprising the structure T3:27 N, where N in this case equals 8 degenerate nucleotides;

T7-4 indicates that the corresponding ligation products were generated in a ligation reaction with only second adaptors comprising the structure T7:N 28 (see FIG. 7B), where N in this case equals 4 degenerate nucleotides;

T7-6 indicates that the corresponding ligation products were generated in a ligation reaction with only second adaptors comprising the structure T7:N 28 (see FIG. 7B), where N in this case equals 6 degenerate nucleotides;

T7-8 indicates that the corresponding ligation products were generated in a ligation reaction with only second adaptors comprising the structure T7:N 28, where N in this case equals 8 degenerate nucleotides;

T3-4+T7-4 indicates that the corresponding ligation products were generated in a ligation reaction with first adaptors comprising the structure T3:27 N and second adaptors comprising the structure T7:N 28, where N in this case equals 4 degenerate nucleotides in all species of both adaptors;

T3-6+T7-6 indicates that the corresponding ligation products were generated in a ligation reaction with first adaptors comprising the structure T3:27 N and second adaptors comprising the structure T7:N 28, where N in this case equals 6 degenerate nucleotides in all species of both adaptors; and T3-8+T7-8 indicates that the corresponding ligation products were generated in a ligation reaction with first adaptors comprising the structure T3:27 N and second adaptors comprising the structure T7:N 28, where N in this case equals 8 degenerate nucleotides in all species of both adaptors.

The number 27 refers to the length of the first oligonucleotide of the first adaptor and the number 28 refers to the length of the third nucleotide of the second adaptor.

Figure 7B:
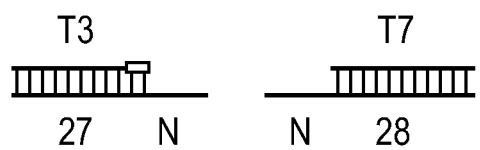

FIG. 7B schematically depicts exemplary first and second adaptors of the current teachings, where N represents a series of degenerate nucleosides on the lower strand of either the exemplary first adaptor or the second adaptor, i.e., the second oligonucleotide or the fourth oligonucleotide, respectively.

Figure 8A:
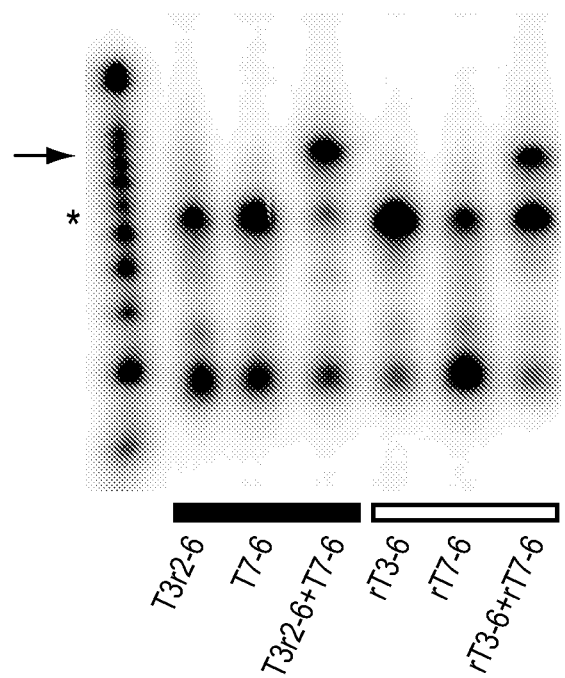
Figure 8B:
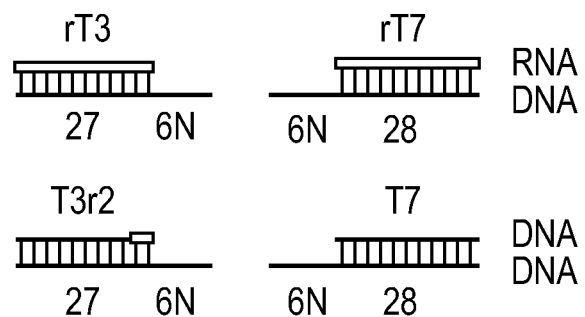

FIG. 8A: depicts an electropherogram of exemplary ligated products (indicated by arrow) generated using various first adaptors, various second adaptors, or combinations of various first adaptors and various second adaptors, as described in Example 5 and depicted in FIG. 8B.

X-axis:

T3r2-6 indicates that the corresponding ligation products were generated in a ligation reaction with only first adaptors comprising T3r2:27 6N (see FIG. 8B), where 6N equals six degenerate nucleotides and r2 designates two 3' ribonucleotides;

T7-6 indicates that the corresponding ligation products were generated in a ligation reaction with only second adaptors comprising T7:6N 28 (see FIG. 8B), where 6N equals six degenerate nucleotides;

T3r2-6+T7-6 indicates that the corresponding ligation products were generated in a ligation reaction with first adaptors comprising T3r2:27 6N and second adaptors comprising T7: 6N 28, where and r2 designates two 3' ribonucleotides and where 6N equals six degenerate nucleotides in all species of both adaptors;

rT3-6 indicates that the corresponding ligation products were generated in a ligation reaction with only first adaptors comprising rT3:27 6N, where 6N equals six degenerate nucleotides and rT3 designates all ribonucleotides, rT7-6 indicates that the corresponding ligation products were generated in a ligation reaction with only second adaptors comprising rT7:6N 28, where rT7 designates all ribonucleotides, 6N equals six degenerate nucleotides; and rT3-6+rT7-6 indicates that the corresponding ligated products were generated in a ligation reaction with first adaptors comprising rT3:27 6N and second adaptors comprising rT7: 6N 28, where rT3 and rT7 designate all ribonucleotides and 6N equals six degenerate nucleotides in all species of both adaptors.

FIG. 8B schematically depicts two exemplary sets of first and second adaptors of the current teachings (the two sets comprise (i) rT3:27 6N (top first adaptor) and rT7:6N 28 (top second adaptor) and (ii) T3r2:27 6N (bottom first adaptor) and T7:6N 28 (bottom second adaptor), where 6N represents a series of six degenerate nucleosides on the lower strand of the exemplary first adaptors and the lower strand of the exemplary second adaptors.

FIG. 9A-FIG. 9C. FIG. 9A and FIG. 9B depict electropherograms of exemplary ligated products generated according to certain embodiments of the current teachings as described in Example 6. Three different combinations of first adaptors and second adaptors were tested for double ligation efficiency. These combinations included first adaptors and second adaptors with both DNA upper strands (i.e., first and third oligonucleotides) except for two ribonucleosides on the 3' end of the first oligonucleotide, both RNA upper strands (i.e., first and third oligonucleotides), or RNA upper strand on 5' (first) adaptor (i.e., first oligonucleotide) and DNA upper strand on 3' (second) adaptor (i.e., third oligonucleotide). FIG. 9C provides a schematic of the latter adaptor structure embodiment having exemplary first adaptors (rT3: 27 6N) and second adaptors (T7:6N 28) (individually also described in FIG. 8B).

Figure 10A:
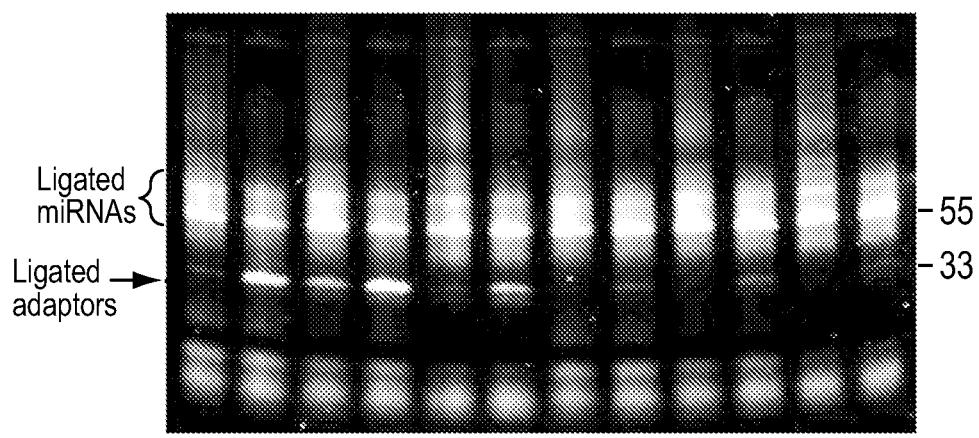
Figure 10B:
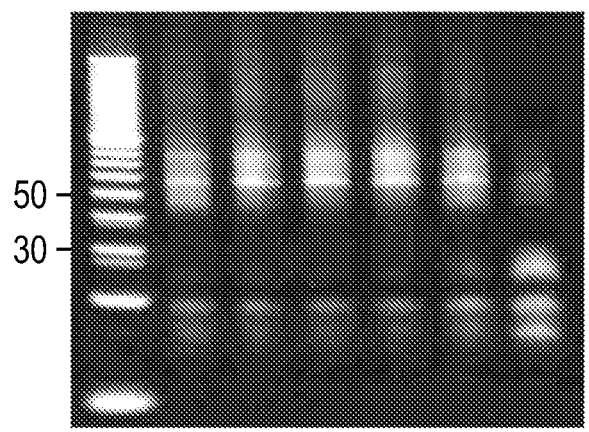

FIG. 10A and FIG. 10B depict two electropherograms showing exemplary ligation products generated according to certain embodiments of the current teachings using a series of ligation reaction compositions, each comprising (1) Rnl2 ligase, (ii) a pool of synthetic miRNA molecules (mirVana miRNA Reference Panel v 9.1, P/N 4388891 (Ambion, Austin, Tex.; described herein) at a concentration of 2 and 0.2 picomoles (pmol), and (iii) first and second adaptors as disclosed herein at upper to lower strand ratios of 10/50, 5/25, 1/5, 1/50, 5/50, 10/50, 25/50, 5/100 or 5/500 (upper strand/lower strand) as shown and described in Example 6.

Figure 11:
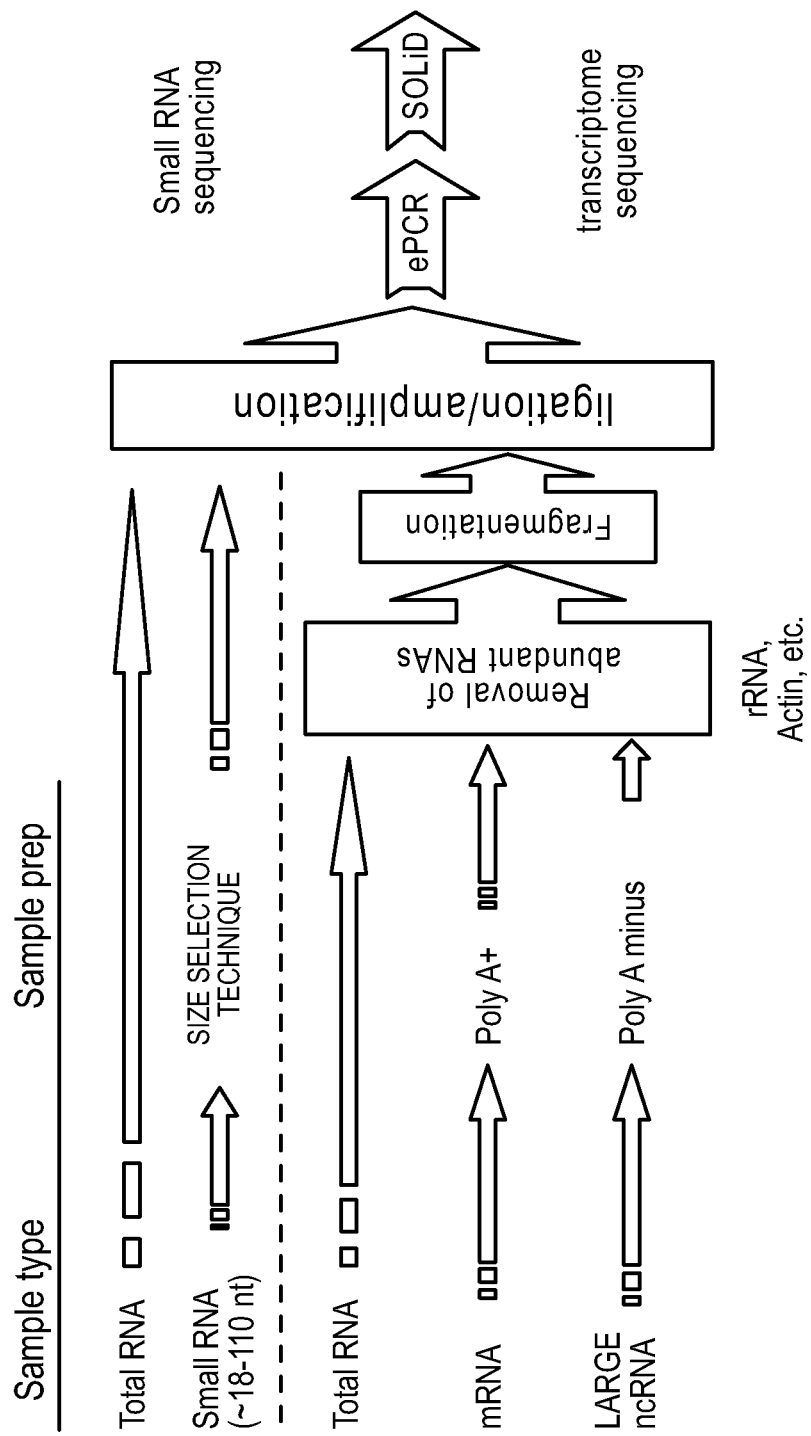

FIG. 11 schematically depicts certain embodiments of the current teachings wherein various subpopulations of nucleic acid are removed and/or purified from the sample. Embodiments of the methods can be used for small RNA detection and isolation and for whole transcriptome sequencing.

Figure 12:
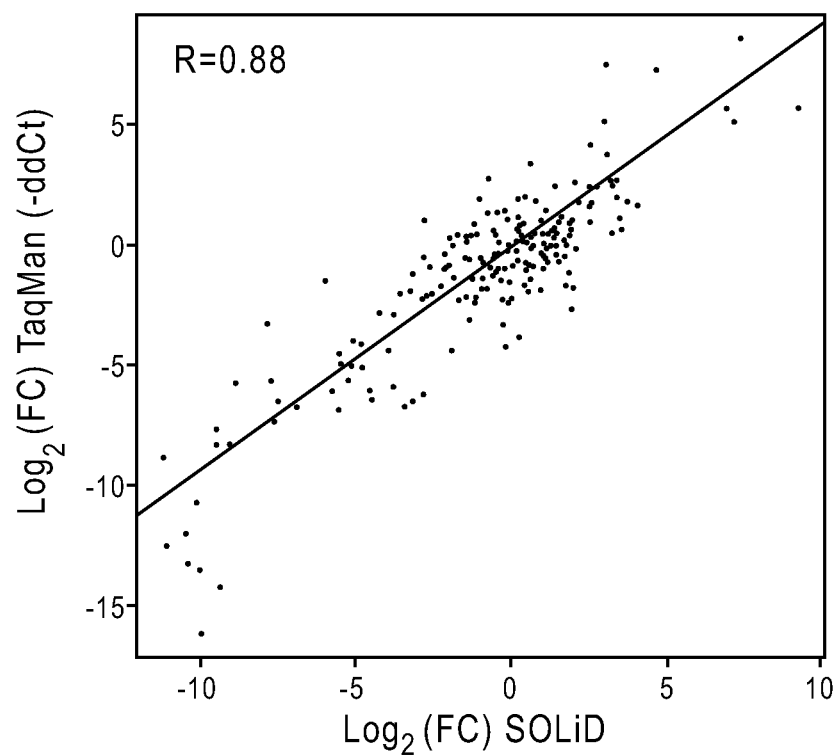

FIG. 12 depicts a graph of $\log_2$ fold change (FC) in $-\Delta\Delta CT$ determined using an exemplary TaqMan®-based detection of illustrative amplified products generated according to one method of the current teachings (shown on y-axis as Log2 (FC) TaqMan (–ddCt)) versus the Log2 (FC) determined using an exemplary sequencing detection technique using the SOLiD™ Sequencing System with an aliquot of the same illustrative amplified products (shown on x-axis as Log2 (FC SOLiD™) as provided by Example 7.

Figure 13A:
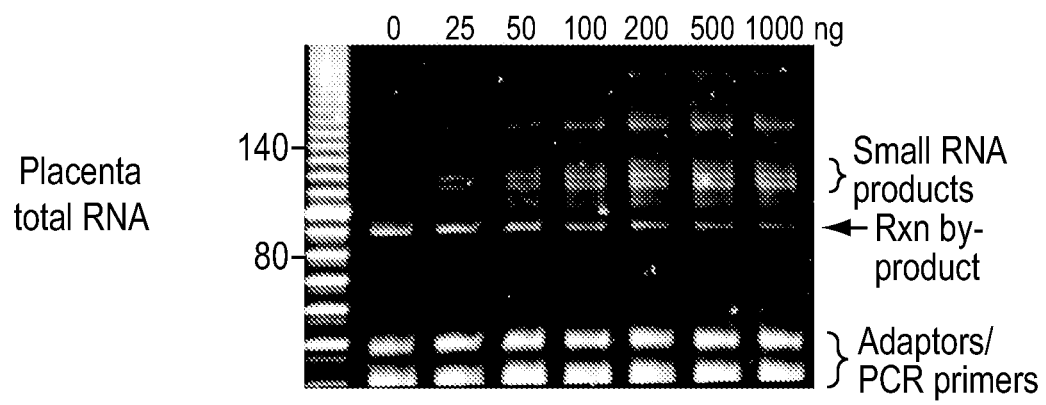
Figure 13B:
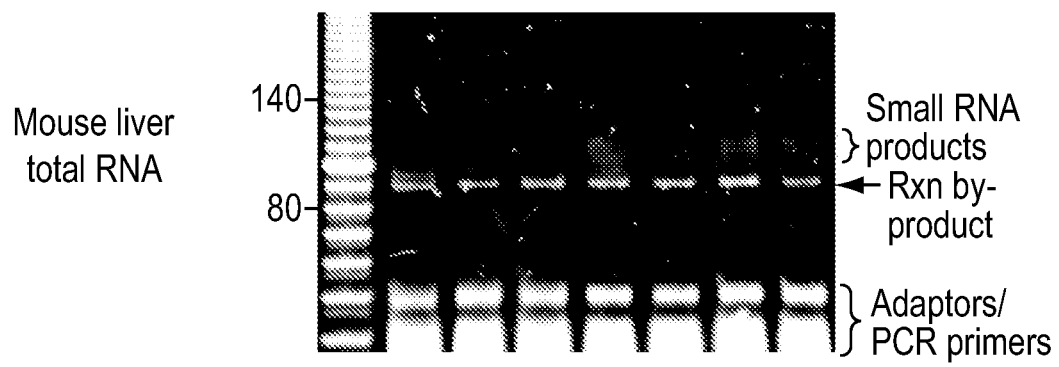

FIG. 13A and FIG. 13B depict electropherograms comprising exemplary amplified products generated by certain embodiments of the current teachings visualized using SYBR® Gold staining as described in Example 7.

FIG. 14 schematically depicts various embodiments of the current teachings comprising detecting RNA molecules of interest by quantitating exemplary amplified products generated according to the current teachings using an intercalating dye, SYBR® Green (e.g., Example 8), for detection in a real-time PCR reaction or SYBR® Gold staining of electrophoretically separated amplified products ("SYBR® Assay"). LEGenD: Ligase Enhanced Gene Detection refers to use of double-strand dependent ligase for assays as provided herein.

FIG. 15 schematically depicts an amplified product of the current teachings as described in Example 8. P1 refers to a portion of the forward PCR primer. P2 refers to a portion of the reverse PCR primer.

Figure 16A:
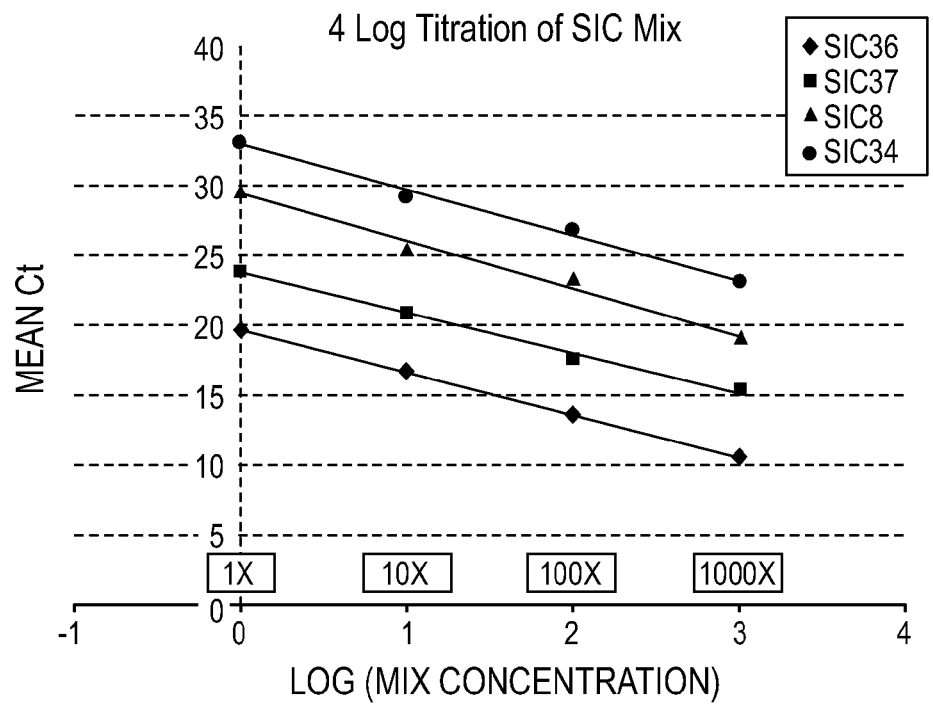
Figure 16B:
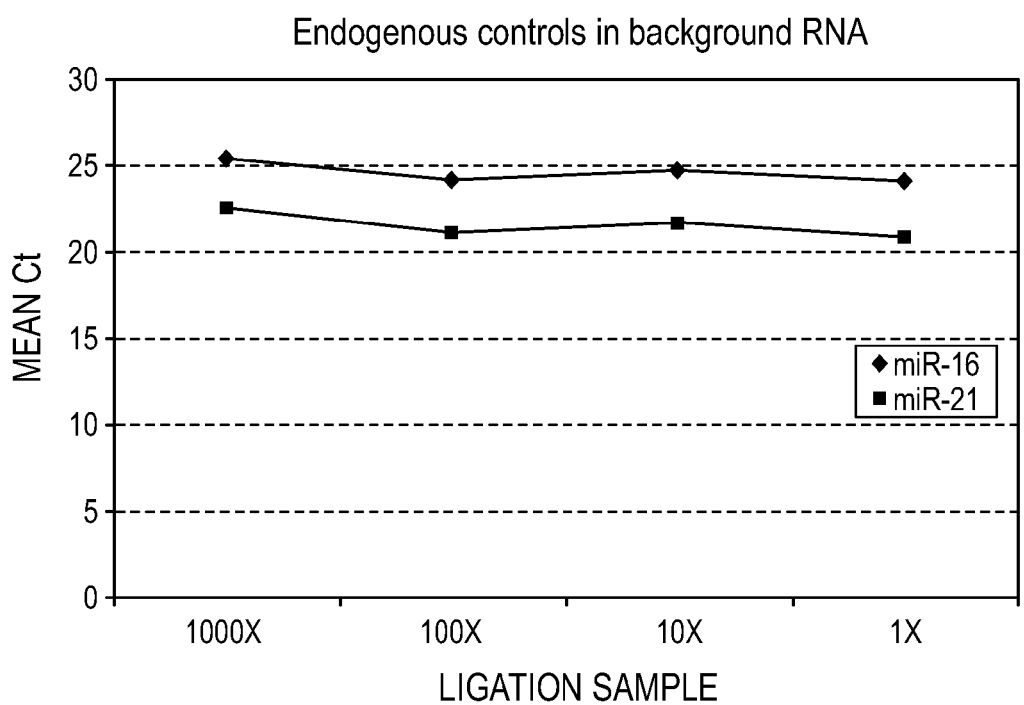

FIG. 16A and FIG. 16B depict illustrative plots of real-time PCR detected RNA molecules, either added to exemplary samples (FIG. 16A) or two ncRNA molecules present in the sample (endogenous miRNAs miR-16 (FIG. 16B, top curve with diamond symbols) and miR-21 (FIG. 16B, bottom curve with square symbols), as described in Example 8. The slope and y-intercepts for FIG. 16A are: SIC 34 (circles, top line): $y=-3.2568x+32.916$, $R^2=0.9918$; SIC 8 (triangles): $y=-3.4116x+29.444$, $R^2=0.9886$; SIC 37 (squares): $y=-2.8517x+23.685$, $R^2=0.9935$; and SIC 36 (diamonds, bottom line): $y=-3.0381x+19.587$, $R^2=0.999$.

Figure 17:
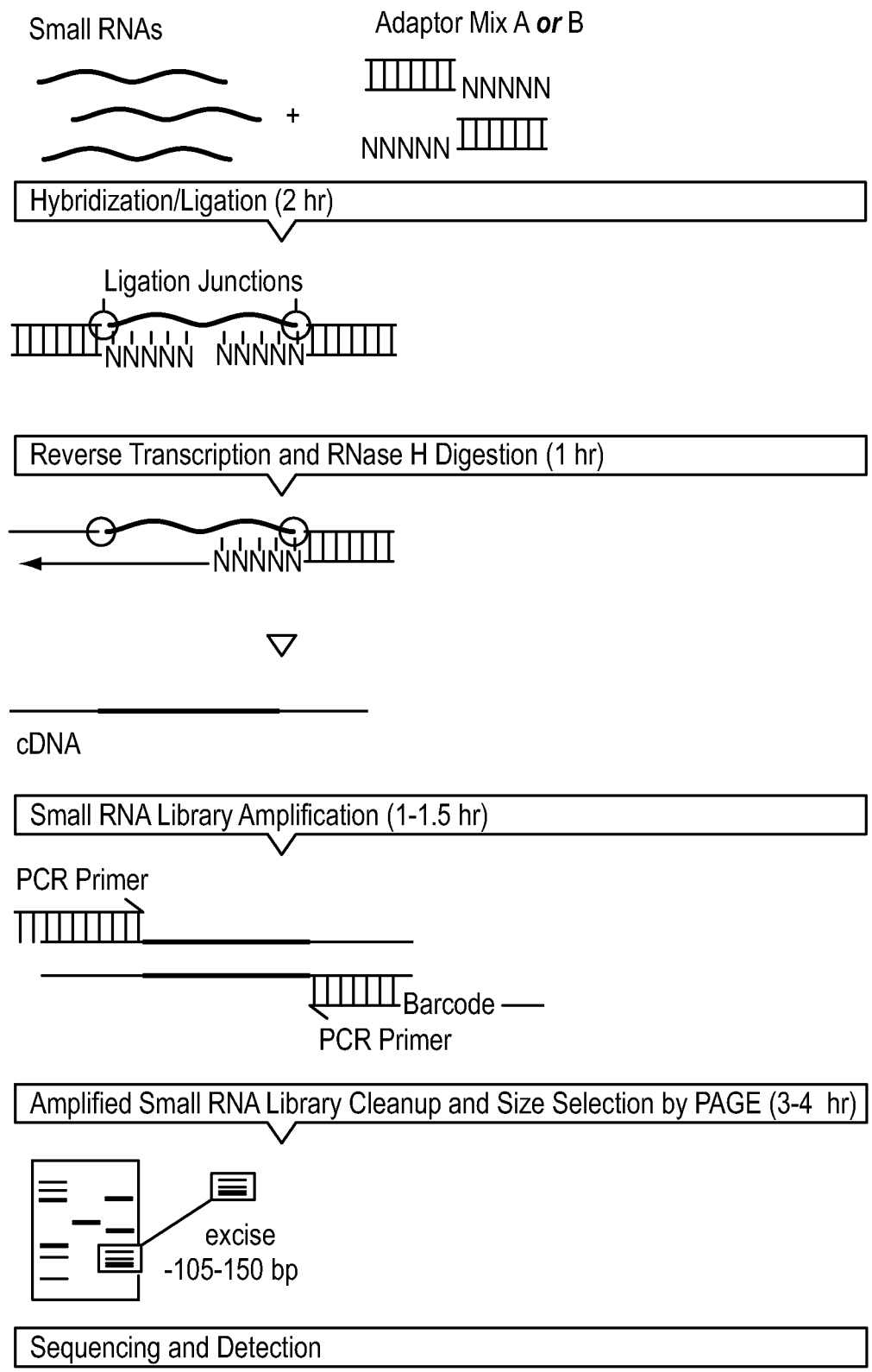

FIG. 17 provides an overview of a SOLiD™ Small RNA Expression Kit procedure for generating a small RNA library as provided in Example 11. Size-selected amplified small RNA enters the SOLiD™ emulsion PCR procedure at the "templated bead preparation" stage.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a forward primer" means that more than one forward primer can be present; for example, one or more copies of a particular forward primer species, as well as one or more different forward primer species. Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including patents, patent applications, articles, books, and treatises are expressly incorporated by reference in their entirety for any purpose. In the event that one or more of the incorporated literature and similar materials defines or uses a term in such a way that it contradicts that term's definition in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

According to certain disclosed methods, for example but not limited to, the exemplary embodiment shown in FIG. 1, a ligation reaction composition is formed comprising at least one RNA molecule to be detected, at least one first adaptor, at least one second adaptor, and a double-strand specific RNA ligase (shown as Hybridization of First and Second Adaptors to RNA Molecule). Typically, the starting material comprises a multiplicity of RNA species and multiplicities of different first adaptors and different second adaptors.

As shown in FIG. 2A and FIG. 2B, the at least one first adaptor 21 comprises a first oligonucleotide 21A comprising at least two ribonucleosides on the 3'-end and a second oligonucleotide 21B that comprises a single-stranded 5' portion 21C when the first oligonucleotide 21A and the second oligonucleotide 21B are hybridized together (FIG. 2A), and wherein the at least one second adaptor 22 comprises a third oligonucleotide 22A that comprises a 5' phosphate group (shown as "P" in FIG. 2B) and a fourth oligonucleotide 22B that comprises a single-stranded 3' portion 22C when the third oligonucleotide 22A and the fourth oligonucleotide 22B are hybridized together (FIG. 2A). It is to be appreciated that in this illustrative embodiment, all of the nucleosides in the first oligonucleotide are ribonucleosides, but that in other embodiments as many as all and as few as two of the nucleosides of the first oligonucleotide can be ribonucleosides, provided that the two 3'-most nucleosides of the first oligonucleotide 21A are ribonucleosides; the remainder of the first oligonucleotide may comprise ribonucleosides, deoxyribonucleosides, or a combination of both.

The single-stranded portions of the illustrative second and fourth oligonucleotides (21C of 21B and 22C of 22B, respectively) of FIG. 2A are depicted as degenerate hexamer sequences (shown as NNNNNN). However, the use of first and/or second adaptors with sequence-specific single stranded portions and also longer and shorter single-stranded portions is within the scope of the current teachings. In some embodiments, the degenerate sequences are deoxyribonucleotides. In some embodiments, the length of the degenerate sequences is 4, 6, or 8 nucleotides. In some embodiments, the first oligonucleotide comprises ribonucleosides and the second, third and fourth oligonucleotides comprise deoxyribonucleotides.

First and second oligonucleotides are designed to be substantially complementary with the exception of the single stranded portion 21C. The substantially complementary portion can have a length of 10 to 60 nucleotides. When annealed or duplexed to form a first adaptor, the first and second oligonucleotides can have one blunt end (as in FIG. 2A and FIG. 2B) or can have an overhang of 1, 2, or 3 nucleotides at the end opposite the end having a single stranded portion. The overhang may be on either the first or the second oligonucleotide.

Third and fourth oligonucleotides are designed to be substantially complementary with the exception of the single stranded portion 22C. The substantially complementary portion can have a length of 10 to 60 nucleotides. When annealed or duplexed to form a second adaptor, the third and fourth oligonucleotides can have one blunt end (as in FIG. 2A and FIG. 2B) or can have an overhang of 1, 2, or 3 nucleotides at the end opposite the end having a single stranded portion. The overhang may be on either the first or the second oligonucleotide.

Returning to FIG. 1, the ligation reaction composition is incubated under conditions suitable for a first adaptor and a second adaptor to anneal with an RNA molecule. The first and third oligonucleotides ("upper strands") may be present in a 1:1 to 1:10 molar ratio to the second and fourth oligonucleotides ("lower strands"). In some embodiments, the molar ratio of "upper strands" to "lower strands" is 1:5 or 1:2. A polypeptide comprising double-strand specific RNA ligase activity is used to ligate the annealed first adaptor-RNA molecule-second adaptor complex to form a ligated product (shown as "Ligation" in FIG. 1). The first adaptor and the second adaptor are ligated to the RNA molecule in the same reaction composition, rather than as two separate sequential ligation reactions with one or more intervening separation or purification steps between ligating the two adaptors to the RNA molecule. It is to be understood the order in which the components of the ligation reaction composition are added and the sequence in which the two adaptors are ligated to the RNA molecule are typically not limitations of the current teachings provided.

As shown in FIG. 2B, in certain embodiments, the first and second adaptors are hybridized to the RNA molecule such that (i) the 3' end of the first oligonucleotide of a first adaptor and the 5' end of the RNA molecule are adjacently annealed to form a first ligation junction (for example, 24 in FIG. 2B) (due to complementarity between the RNA molecule and the single stranded portion of the first adaptor) and (ii) the 5' end of third oligonucleotide of a second adaptor and 3' end of the same RNA molecule are adjacently annealed to form a second ligation junction (for example, 25 in FIG. 2B) (due to complementarity between the RNA molecule and the single stranded portion of the second adaptor), wherein the first and the second ligation junctions are both suitable for ligation using a polypeptide comprising double strand-specific RNA ligase activity. In some embodiments, the polypeptide comprising double strand-specific RNA ligase activity comprises an Rnl2 family ligase, including without limitation, Rnl2 ligase.

An RNA-directed DNA polymerase is combined with the ligated product, along with suitable nucleotide triphosphates and a buffer solution comprising appropriate salts. This reaction mixture is incubated under conditions suitable for a reverse transcribed product to be generated using the ligated product as the template (shown as "Reverse Transcription" in FIG. 1). A separate reverse transcription primer is not needed since the fourth oligonucleotide serves as the RT primer.

In some embodiments, the reverse transcribed product is placed on an array and detected using standard methods known by one of skill in the art. In some embodiments, the reverse transcribed product is labeled with biotin and detection is by using streptavidin binding thereto. In some embodiments, the reverse transcribed product is purified using glass fiber filters, beads or is gel-purified. In some embodiments, the reverse transcribed product is combined with a peptide comprising ribonuclease activity to form a digestion reaction composition and incubated under conditions suitable for digesting at least some of the ribonucleosides from the reverse transcribed product to form an amplification template. In some embodiments, the peptide comprising ribonuclease activity comprises ribonuclease H (RNase H) activity (shown as "RNase H Digestion" in FIG. 1).

The amplification template is combined with at least one forward primer, at least one reverse primer, and a peptide comprising DNA-directed DNA polymerase activity to form an amplification reaction composition. When a DNA polymerase having both RNA-directed and DNA-directed polymerase activities is used in the reverse transcription reaction above, a further peptide comprising DNA-directed DNA polymerase does not need to be added. The amplification reaction composition is thermocycled under conditions suitable to allow amplified products to be generated (shown as "Amplification" in FIG. 1). The sequence of at least part of the amplified product is determined, which allows the corresponding RNA molecule to be detected (shown as "Sequence Determination" in FIG. 1).

According to one exemplary embodiment, depicted schematically in FIG. 3, a population of small RNA molecules 33 is combined with a first adaptor 31 comprising a first oligonucleotide comprising RNA (shown in the open box) and a second adaptor 32 and Rnl2 ligase to form a ligation reaction composition. The ligation reaction composition is incubated under conditions suitable for annealing to occur and a first adaptor and a second adaptor anneal with a small RNA molecule to form a ligation template comprising the first adaptor annealed to the 5'-end of the RNA molecule and the second adaptor annealed to the 3'-end of the small RNA molecule. The ligase will generate a ligated product 34 by ligating the first adaptor to the 5'-end of the RNA molecule and the second adaptor to the 3'-end of the RNA molecule at the ligation junctions (shown as solid dots in FIG. 3 and indicated by arrows). Depending on the concentration of adaptors and RNA molecules in the ligation reaction composition, some unannealed first adaptors 31 and/or second adaptors 32 may also be present in the ligation reaction composition. Additionally, particularly when the first and/or second adaptors comprise degenerate sequences, undesired annealed byproduct molecules 35 can also form.

The reaction composition comprising the ligated product is combined with an RNA-directed DNA polymerase and under suitable conditions a reverse transcribed product 36 is generated. The reaction composition comprising the reverse transcribed product 36 is combined with ribonuclease H and at least some of the ribonucleosides of the ligated product are digested and an amplification template 38 is generated. Those in the art will appreciate that, at this point, the amplification template comprises, in essence, the cDNA strand of the reverse transcribed product annealed with the third oligonucleotide of the second adaptor. The amplification template 38 is combined with a DNA-directed DNA polymerase, a forward primer 310 and a reverse primer 311 to form an amplification reaction composition. In this illustrative embodiment, the reverse primer further comprises an identification sequence 312, sometimes referred to as a "bar code" sequence. If all of the reverse primers in a given amplification reaction composition comprise the same identification sequence and that sequence is incorporated into subsequent amplicons, then all of the amplicons generated from the same amplification reaction composition can be identified as having come from that reaction composition.

The amplification reaction composition is temperature cycled to allow the polymerase chain reaction to occur and a plurality of amplified products is generated. In this illustrative embodiment, the amplified products are purified using polyacrylamide gel electrophoresis (PAGE) and/or high performance liquid chromatography (HPLC; sometimes referred to as high pressure liquid chromatography). The purified amplified products are sequenced using any technique known in the art, and the RNA molecule corresponding to that sequence is identified. Those in the art will appreciate that the disclosed method may be useful for a variety of analyses, including without limitation, expression profiling, quantitating one or more specific RNA molecules in one or more corresponding samples (e.g., with and without drug treatment; a malignant/tumor tissue and the corresponding normal tissue sample; developmental studies using corresponding embryonic, neonatal, adolescent, and/or adult tissues), and small RNA discovery.

It is to be appreciated that if multiple libraries of amplified product are to be generated, each amplified product library can be identified by a unique identification sequence or barcode for that library. In some embodiments, the PCR primer mix for a given amplified product library comprises a forward primer (for illustration purposes, see forward primer 310 in FIG. 3) and a reverse primer that contains a unique identification sequence or barcode (for illustration purposes, see reverse primer 311 comprising identifier sequence 312 in FIG. 3). When an amplification reaction composition comprising such a primer pair is cycled, the barcode is becomes incorporated into the amplified products of that library. Thus, the exemplary first primer can be matched with any of these exemplary reverse primers in an amplification reaction composition to generate a library of amplified products comprising the barcode of the reverse primer or its complement.

For illustration purposes but not as a limitation, each amplified product in a first library generated using a PCR primer mix including the exemplary forward primer and exemplary reverse primer BC1 (see Example 11) will contain the barcode sequence AAGCCC and/or its complement; while each amplified product in a second library generated using a PCR primer mix including the exemplary forward primer and exemplary reverse primer BC2 will contain the barcode sequence CACACC and/or its complement; and so forth. Thus, multiple libraries of amplified product can be pooled prior to sequencing and the RNA molecules in the starting material corresponding to each library can be identified using the target (RNA molecule) sequence or at least part of that sequence combined with the barcode or identification sequence for that library. Those in the art will appreciate that various identification sequences can be employed to uniquely mark the amplified products generated in a given amplification reaction composition.

FIG. 4 schematically depicts another exemplary embodiment of the current teachings. According to this embodiment, the first and second adaptors are hybridized with the RNA molecule (shown as Adaptor Hybridization in FIG. 4) and under suitable conditions and in the presence of an appropriate ligase, ligated product is generated (shown as Ligation in FIG. 4). Reverse transcriptase is added to the ligated product and a reverse transcribed product is generated under suitable conditions (shown as Reverse Transcription in FIG. 4). The reverse transcribed product is digested with ribonuclease H and an amplification template is formed (shown as RNase H in FIG. 4). An amplification reaction composition is formed comprising the amplification template, forward primer, reverse primer, and a DNA-directed DNA polymerase. The amplification reaction composition is thermocycled for a number of cycles that stays within a linear range of amplification (generally, ~12-15 cycles or 12-18 cycles according to one exemplary embodiment), allowing the polymerase chain reaction to occur and amplified product to be generated (shown as PCR in FIG. 4). In this illustrative embodiment, the amplified product is gel purified (shown as Gel Purif. in FIG. 4) resulting in purified amplified product. Provided that appropriately size fractionated or fragmented RNA molecules were used, the amplified product comprises an insert sequence (shown by a curved bracket in FIG. 4; in certain embodiments, insert sizes are about 15 base pairs to about 100 base pairs), a first primer region (shown as P1 in FIG. 4), and a second primer region (shown as P2 in FIG. 4) that includes a bar code or identification sequence (shown as be in FIG. 4).

As used herein, the terms "polynucleotide", "oligonucleotide", and "nucleic acid" are used interchangeably and refer to single-stranded and double-stranded polymers of nucleoside monomers, including 2'-deoxyribonucleosides (DNA) and ribonucleosides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleosides, entirely of ribonucleosides, or chimeric mixtures thereof. As further described below, for example, first adaptors include a first oligonucleotide having at least two ribonucleosides on its 3' end. First oligonucleotides can have 2, 3, 4, 5, 6, 7, 8, 9, 10, 11, 12, 13, 14, 15, 20, 25, or more ribonucleosides and in some embodiments, the ribonucleosides are contiguous. In some embodiments, second, third or fourth oligonucleotides comprise deoxyribonucleotides. The nucleotide monomer units may comprise any of the nucleotides described herein, including, but not limited to, nucleotides and nucleotide analogs. Polynucleotides typically range in size from a few monomeric units, e.g. 5-40 or 5-60 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right.

RNA Molecule to be Detected:

In some embodiments, the RNA molecules of the current teachings comprise total RNA, a subset or fraction of total RNA, or both. In some embodiments, a sample comprising the RNA molecule to be detected comprises all of the RNA obtained from a particular sample or pool of samples. In other embodiments, the total RNA is fractionated into subsets and the RNA molecule to be detected is present in one or more of the fractionated subsets. Typically, RNA molecules are extracted from a sample using any technique known in the art that yields total RNA or a subset of RNA molecules in the sample.

In some embodiments, the RNA molecules to be detected are fragmented, typically prior to forming the ligation reaction composition. In some embodiments, total RNA can be fragmented or fractionated RNA can be fragmented and analyzed using methods provided herein. In some embodiments, the RNA molecule to be detected comprises a plurality of different RNA species, including without limitation, a plurality of different mRNA species, which may or may not be fragmented prior to generating ligation products. In some embodiments the RNA is fragmented chemically, enzymatically, mechanically, by heating, or combinations thereof using methods well known in the art. Fragmented RNA is analyzed using methods provided herein. Whole transcriptome analysis can thus be carried out wherein sequences that are transcribed from DNA are analyzed, including coding RNA (e.g., for expression analysis) or noncoding RNA.

In some embodiments, small RNA molecules and/or fragmented RNA in a certain size range are obtained from a sample, for example using a size fractionation procedure. In some embodiments, the total RNA is fragmented and may also be size fractionated prior to ligating the first and second adaptors; while in other embodiments total RNA is used in the ligation reaction composition. For illustration purposes, but not as a limitation, certain fractionation techniques are depicted in FIG. 11.

In some embodiments, a poly A selection process is performed to separate messenger RNA (mRNA) from those RNA molecules that lack poly A (poly A minus RNA molecules). In some embodiments, the total RNA is fractionated into subsets by separating at least some of the mRNA from the total RNA, for example but not limited to, using a polyA selection technique known in the art, including without limitation, oligo-dT chromatography. In such embodiments, either the poly A+ fraction or the poly A depleted fraction may be employed in the current teachings to detect at least some of the RNA molecules that are present in that fraction. In some embodiments, both fractions may be used separately to detect at least some of the RNA molecules that are present in each fraction. In some embodiments, the RNA molecules of interest comprise poly A minus RNA molecules, for example but not limited to large non-coding RNA.

In certain embodiments, a population of mRNA molecules or a population of poly A minus RNA molecules is depleted of at least one species of abundant RNA molecule in the population, for example but not limited to, ribosomal RNA, or mRNA from housekeeping or highly expressed genes, including without limitation, actin mRNA and globin mRNA. For example, certain mRNAs or classes of RNA are depleted from the total RNA, for example but not limited to, high copy number mRNAs such as actin, GAPDH, globin and other "housekeeping" mRNA; and classes of RNA for example but not limited to 18S RNA and 28S RNA (for example, using commercially available kits such as the RiboMinus (Invitrogen, Carlsbad, Calif.) or GLOBINclear™ (Ambion, Austin, Tex.) Kits (see also U.S. Patent Application Publication US 2006/0257902, Methods and Compositions for Depleting Abundant RNA Transcripts).

The term chemical fragmentation is used in a broad sense herein and includes without limitation, exposing the sample comprising the RNA to metal ions, for example but not limited to, zinc ($Zn^{2+}$), magnesium ($Mg^{2+}$), and manganese ($Mn^{2+}$) and heat.

The term enzymatic fragmentation is used in a broad sense and includes combining the sample comprising the RNA with a peptide comprising nuclease activity, such as an endoribonuclease or an exoribonuclease, under conditions suitable for the peptide to cleave or digest at least some of the RNA molecules. Exemplary nucleases include without limitation, ribonucleases (RNases) such as RNase A, RNase T1, RNase T2, RNase U2, RNase PhyM, RNase III, RNase PH, ribonuclease V1, oligoribonuclease (e.g., EC 3.1.13.3), exoribonuclease I (e.g., EC 3.1.11.1), and exoribonuclease II (e.g., EC 3.1.13.1), however any peptide that catalyzes the hydrolysis of an RNA molecule into one or more smaller constituent components is within the contemplation of the current teachings. Fragmentation of RNA molecules by nucleic acids, for example but not limited to, ribozymes, is also within the scope of the current teachings.

The term mechanical fragmentation is used in a broad sense and includes any method by which nucleic acids are fragmented upon exposure to a mechanical force, including without limitation, sonication, collision or physical impact, and shear forces.

In some embodiments, very small fragments of RNA are removed using a "clean up" step, for example but not limited to, purification using gel electrophoresis, glass fiber filters or using magnetic beads, prior to using the remaining larger RNA molecules according to the current teachings.

In certain embodiments, the methods of the current teachings employ RNA molecules that were fractionated using a physical separation method, including without limitation, size separation methods such as centrifugation, column chromatography/gel sieving, and electrophoretic separation. In some embodiments, electrophoretic separation of RNA molecules of interest comprise the flashPAGE™ Fractionator System (Ambion, Austin, Tex.) or size selection by slicing a band from an agarose or polyacrylamide gel according to methods known in the art. In some embodiments, the RNA molecules used in certain disclosed methods can be obtained by extracting a subset of RNA molecules in a sample using any of a variety of sample preparation kits and reagents, including without limitation, the mirVana™ miRNA Isolation Kit (Ambion). In some embodiments, RNA may be immunoprecipitated.

The terms non-coding RNA or ncRNA refer to any RNA molecule, regardless of size, that is not translated into a protein. Exemplary ncRNAs include transfer RNA (tRNA), ribosomal RNA (rRNA), microRNA (miRNA), small nuclear RNA (snRNA), small nucleolar RNA (snoRNA), guide RNA (gRNA), efference RNA (eRNA), Piwi-interacting RNA (piRNA), Repeat-associated siRNA (rasiRNA), signal recognition particle RNA, promoter RNA (pRNA), small interfering RNA (siRNA), and transfer-messenger RNA (tmRNA).

Those of skill in the art will appreciate that the length of RNA molecule to be detected is not a limitation of the current teachings since longer molecules can be fractionated and/or fragmented and the fractions and/or fragments detected so as to reconstruct the RNA molecule. In some embodiments, the length of the RNA molecule to be detected is 12 to 500 nucleotides, 15 to 110 nucleotides, 15 to 100 nucleotides, 18 to 110 nucleotides, 20 to 80 nucleotides, 25 to about 60 nucleotides, 20 to about 45 nucleotides, 20 to about 41 nucleotides, 20 to about 40 nucleotides, 21, 22, 23, 24, or 25 to about 36, 37, 38, 39, 40, or 41 nucleotides, or any integer range therebetween. In some embodiments, the RNA molecule to be detected has a length of 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 nucleotides.

Those in the art will appreciate that the techniques used to fractionate or fragment RNA is not a limitation of the current teachings and that various fractionation or fragmentation techniques can typically be employed, depending on which fraction(s) or fragment(s) of RNA molecules is to be detected.

In certain embodiments, the starting material comprises at least one synthetic RNA molecule, such as a spike-in control that may be used for, among other things, calibration or standardization. In some embodiments, at least one synthetic RNA molecule species is added to a sample comprising naturally occurring RNA molecules and the presence of at least one synthetic RNA species and at least one naturally occurring RNA species is detected according to the disclosed methods.

In some embodiments, the RNA molecule to be detected has a 5'-monophosphate and a 3'-hydroxyl for efficient ligation. For example, some small RNA biogenesis results in RNA molecules with 5'-ends comprising triphosphates. According to certain embodiments of the current teachings, such RNA molecules are not suitable for adaptor ligation and amplification. Thus, intact mRNA molecules with a 5' cap structure, and RNA molecules with a 5' triphosphate, including small RNAs such as endogenous siRNA from *C. elegans* (Pak 2007), cannot be effectively ligated to the hybridized adaptors in the reaction composition, unless they are first treated with a decapping enzyme, for example but not limited to, tobacco acid pyrophosphatase (TAP), nuclease P1, Dcp1p decapping enzyme, Dcp2 decapping enzyme, or DcpS decapping enzyme to convert the 5' ends of RNA molecules to 5' monophosphates. Where the RNA molecule of interest comprises 5'-triphosphates, certain embodiments of the current teachings employ tobacco acid pyrophosphatase to convert the 5'-ends of RNA molecules to 5' monophosphates, rendering them suitable for ligation.

In some embodiments, fragments generated by certain fragmentation techniques do not initially possess a terminus that is suitable for enzymatic ligation; in some embodiments, such fragments are treated with a kinase, for example but not limited to, bacteriophage T4 polynucleotide kinase, to render the 5'-ends or 3'-ends suitable for ligating according to the current teachings.

RNA to be detected may be single stranded or double stranded since the RNA to be detected is combined with at least one first adaptor, at least one second adaptor, and annealed such that a polypeptide comprising double-strand specific RNA ligase can form a ligated product.

According to the current teachings, an RNA molecule of interest can be either synthetic or naturally occurring. RNA molecules can be synthesized using oligonucleotide synthesis methods that are well-known in the art. RNA molecules can also be synthesized biochemically, in vivo or in vitro, according to methods known in the art, for example but not limited to in vitro transcription techniques, including without limitation, U.S. Pat. Nos. 5,958,688; 5,723,290; 5,514,545; 5,021,335; 5,168,038; 5,545,522; 5,716,785; 5,891,636; and 6,291,170. Detailed descriptions of such techniques can be found in, among other places, Current Protocols in Nucleic Acid Chemistry, Beaucage et al., eds., John Wiley & Sons, New York, N.Y., including updates through May 2005 (hereinafter "Beaucage et al."); and Blackburn and Gait. Automated nucleic acid synthesizers useful for synthesizing RNA molecules, adaptors, and primers are commercially available from numerous sources, including for example, Applied Biosystems (Foster City, Calif.). RNA molecules, adaptors, and primers can also be generated biosynthetically, using in vivo methodologies and/or in vitro methodologies that are well known in the art. Descriptions of such technologies can be found in, among other places, Sambrook et al. and Ausubel et al. Nucleoside analogs, such as 2'-OMe-, LNA-, halo-, or arabino-derivatives, for example, or universal nucleobases can be incorporated into adaptors as long as the fourth oligonucleotide is a primeable substrate. Purified or partially purified RNA is commercially available from numerous sources, including FirstChoice® Total RNA, FirstChoice® Poly(A), FirstChoice® Tumor RNA, and the mirVana™ miRNA Reference Panel (Ambion, Austin, Tex.); Reference Total RNA, Human and Mouse, and Universal Reference RNAs (Stratagene, La Jolla, Calif.); and the American Type Culture Collection (ATCC), Manassas, Va.

In some embodiments, the RNA molecule to be detected is present in a sample. The term "sample" is used in a broad sense herein and is intended to include a wide range of biological materials as well as compositions derived or extracted from such biological materials comprising or suspected of comprising RNA. Exemplary samples include whole blood; red blood cells; white blood cells; buffy coat; hair; nails and cuticle material; swabs, including buccal swabs, throat swabs, vaginal swabs, urethral swabs, cervical swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; pulmonary lavages; lung aspirates; and tissues, including, liver, spleen, kidney, lung, intestine, brain, heart, muscle, pancreas, biopsy material, and the like. The skilled artisan will appreciate that lysates, extracts, or materials obtained from any of the above exemplary biological samples are also within the scope of the current teachings. Tissue culture cells, including explanted material, primary cells, secondary cell lines, and the like, as well as lysates, extracts, or materials obtained from any cells, are also within the meaning of the term biological sample as used herein. Materials comprising or suspected of comprising at least one RNA molecule that are obtained from forensic, agricultural, and/or environmental settings are also within the intended meaning of the term sample. In certain embodiments, a sample comprises a synthetic nucleic acid sequence. In some embodiments, a sample is totally synthetic, for example but not limited to, a control sample comprising a buffer solution containing at least one synthetic nucleic acid sequence. In certain embodiments, the sample is an environmental sample, such as a soil, water, or air sample.

Plant miRNAs can have a 2'-O-methyl group at the 3' end and can be ligated in a ligation reaction as cited herein. However, the efficiency of such a ligation will be reduced compared to RNA species with a 2'-OH at the 3' end.

First Adaptors and Second Adaptors:

As stated above, at least one first adaptor comprises a first oligonucleotide comprising at least two ribonucleosides on the 3'-end and a second oligonucleotide that comprises a single-stranded 5' portion when the first oligonucleotide and the second oligonucleotide are hybridized together as depicted in FIG. 2A. First and second oligonucleotides are designed to be substantially complementary with the exception of the single stranded portion, further described below. The substantially complementary portion can have a length of 10 to 60 nucleotides. In some embodiments, the substantially complementary portion can have a length of 10 to 40 nucleotides, 12 or 15 to 30 nucleotides, 20, 21, 22, or 23 to 25, 27 or 29 nucleotides, or any integer range between any of these ranges. When annealed or duplexed to form a first adaptor, the first and second oligonucleotides can have one blunt end (as in FIG. 2A and FIG. 2B) or can have an overhang of 1, 2, or 3 nucleotides at the end opposite the end having a single stranded portion. The overhang may be on either the first or the second oligonucleotide.

Also as stated above, at least one second adaptor comprises a third oligonucleotide that comprises a 5' phosphate group and a fourth oligonucleotide that comprises a single-stranded 3' portion when the third oligonucleotide and the fourth oligonucleotide are hybridized together also as depicted in FIG. 2A. Third and fourth oligonucleotides are designed to be substantially complementary with the exception of a single stranded portion, further described below. The substantially complementary portion can have a length of 10 to 60 nucleotides. When annealed or duplexed to form a second adaptor, the third and fourth oligonucleotides can have one blunt end (as in FIG. 2A and FIG. 2B) or can have an overhang of 1, 2, or 3 nucleotides at the end opposite the end having a single stranded portion. The overhang may be on either the first or the second oligonucleotide.

In some embodiments, first, second, third and fourth oligonucleotides independently comprise deoxyribonucleosides, ribonucleotides, or both deoxyribonucleotides and ribonucleotides with the exception that the first oligonucleotide comprises at least two ribonucleosides on the 3'-end. It is to be appreciated that in the illustrative embodiment of FIG. 2A, all of the nucleosides in the first oligonucleotide are ribonucleosides, but that in other embodiments as many as all and as few as two of the nucleosides of the first oligonucleotide can be ribonucleosides, provided that the two 3'-most nucleosides of the first oligonucleotide are ribonucleosides; the remainder of the first oligonucleotide may comprise ribonucleosides, deoxyribonucleosides, or a combination of both. In some embodiments, the second, third and fourth oligonucleotides comprise deoxyribonucleosides and the first oligonucleotide comprises all ribonucleosides. In some embodiments, the first oligonucleotide comprises ribonucleosides and the second, third and fourth oligonucleotides comprise deoxyribonucleotides. The length of oligonucleotides of first and second adaptors is independent of each other.

The sequences of the first, second, third and fourth oligonucleotides are such that substantial complementarity is achieved in the duplexed portion of the adaptors as described above. In some embodiments, the sequences of the first and the third oligonucleotides are different. The specific sequence of nucleotides of the duplexed portions of the adaptors is not limiting for the methods herein. In some embodiments, a portion of an adaptor sequence comprises a "promoter sequence," including without limitation a sequence suitable for initiating transcription using a suitable polymerase, for example but not limited to, T3 RNA polymerase, T7 RNA polymerase, or SP6 RNA polymerase. In some embodiments, a first adaptor comprises a "promoter sequence" for a first promoter and a second adaptor comprises a "promoter sequence" for a second promoter.

The 3'-end of the first oligonucleotide and the 5'-end of the third oligonucleotide are suitable for ligation to an RNA molecule to be detected, which also is suitable for ligation. Oligonucleotides "suitable for ligation" refers to at least one RNA molecule to be detected, and at least one first adaptor and/or at least one second adaptor, each comprising an appropriate reactive group. Exemplary reactive groups include, but are not limited to, a free hydroxyl group on the 3' end of the first oligonucleotide of a first adaptor and a free phosphate group on the 5' end of the RNA molecule to be detected, a free hydroxyl group on the 3' end of the RNA molecule to be detected and a free phosphate group on the 5' end of the third oligonucleotide of a second adaptor.

Single-Stranded Portions of Adaptors:

The single-stranded portions of the illustrative second and fourth oligonucleotides are depicted in FIG. 2A as degenerate hexamer sequences (shown as NNNNNN). However, the use of first and/or second adaptors with sequence-specific single-stranded portions and also longer and shorter single-stranded portions is within the scope of the current teachings.

In some embodiments, the single-stranded portions comprise, independently, deoxyribonucleosides, ribonucleosides or a combination of deoxyribonucleosides and ribonucleosides. In some embodiments, the single-stranded portions comprise deoxyribonucleosides.

In some embodiments of single-stranded portions of adaptors, the length of the single-stranded portion is as short as one nucleotide and as long as 8 nucleotides. In some embodiments, the length of the single-stranded portion is 2, 4, 6, or 8 nucleotides. In some embodiments, the length of the single-stranded portion is 4 or 6 nucleotides. The length of the single-stranded portion of the second oligonucleotide is independent of the length of the single-stranded portion of the fourth oligonucleotide.

In some embodiments the nucleoside sequence of a single-stranded portion is designed to be complementary to a 5'-sequence or a 3'-sequence of a specific RNA molecule to be detected. In some embodiments, the specific RNA molecule to be detected hybridizes with the single-stranded portion of at least one first adaptor and the single-stranded portion of at least one second adaptor such that a ligation reaction can occur. For hybridizing to specific sequences in some embodiments, the length of the single-stranded portions are independently 4 to 6 nucleotides long. In such a method, the RNA molecule is directionally detected by methods herein. One of ordinary skill in the art can design a single-stranded portion corresponding to the 5'-sequence or a 3'-sequence of the RNA molecule to be detected and using the detection methods provided herein detect either the sense sequence or the antisense sequence corresponding to the RNA molecule.

In some embodiments, the sequence of a single-stranded portion is designed to be a degenerate sequence to allow all RNA molecules of a sample having complementary to the degenerate sequence to anneal to the single-stranded portion of the adaptor. In some embodiments, degenerate single-stranded portions have a length of 1 to 8 nucleotides. In some embodiments, degenerate single-stranded portions have a length of 4, 6, or 8 nucleotides. In some embodiments, the degenerate nucleoside sequences are deoxyribonucleotides.

In some embodiments, the sequence of a single-stranded portion of a second or fourth oligonucleotide is a degenerate sequence and the sequence of the other of the second or fourth oligonucleotide is a sequence corresponding to the RNA molecule to be detected.

Annealing or Hybridizing:

The terms "annealing" and "hybridizing" including, without limitation, variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. For example, conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether annealing takes place is influenced by, among other things, the length of the complementary portion of the nucleic acids, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of nucleic acids can also influence hybridization conditions. Thus, the preferred annealing conditions will depend upon the particular application. Such conditions, however, can be routinely determined by persons of ordinary skill in the art, without undue experimentation. Typically, annealing conditions are selected to allow nucleic acids to selectively hybridize with a complementary or substantially complementary sequence, but not hybridize to any significant degree to other sequences in the reaction.

The term "selectively hybridize" and variations thereof means that, under suitable conditions, a given sequence anneals with a second sequence comprising a complementary or a substantially complementary string of nucleotides, but does not anneal to undesired sequences. In this application, a statement that one sequence selectively hybridizes or anneals with another sequence encompasses situations where the entirety of both of the sequences hybridize to one another, and situations where only a portion of one or both of the sequences hybridizes to the entire other sequence or to a portion of the other sequence. For the purposes of this definition, the term "sequence" includes nucleic acid sequences, polynucleotides, oligonucleotides, primers, target-specific portions, amplification product-specific portions, primer-binding sites, hybridization tags, and hybridization tag complements.

The term "corresponding" as used herein refers to at least one specific relationship between the elements to which the term relates. For example, a single-stranded 5' portion of a first adaptor corresponds to a RNA molecule having a terminal nucleotide sequence that hybridizes to the single-stranded portion. A single-stranded 3' portion of a second adaptor corresponds to a RNA molecule having a terminal nucleotide sequence that hybridizes to the single-stranded portion. Further examples include where a primer binds to the corresponding complementary or substantially complementary primer-binding portion of a nucleic acid, where a particular affinity tag binds to the corresponding affinity tag, for example but not limited to, biotin binding to streptavidin, and where a particular hybridization tag anneals with its corresponding hybridization tag complement; and the like.

In this application, a statement that one sequence is the same as, substantially the same as, complementary to, or substantially complementary to another sequence encompasses situations where both of the sequences are completely the same as, substantially the same as, or complementary or substantially complementary to one another, and situations where only a portion of one of the sequences is the same as, substantially the same as, complementary to, or substantially complementary to a portion or the entire other sequence. For the purposes of this definition, the term "sequence" includes RNA, DNA, polynucleotides, oligonucleotides, primers, ligated products, reverse transcribed products, amplification templates, amplified products, primer-binding sites, hybridization tags, and hybridization tag complements.

The terms "denaturing" or "denaturation" as used herein refer to any process in which a double-stranded polynucleotide, including a double-stranded amplification product or a double-stranded DNA or a DNA:RNA duplex is converted to two single-stranded polynucleotides. Denaturing a double-stranded polynucleotide includes without limitation, a variety of thermal or chemical techniques for denaturing a duplex, thereby releasing its two single-stranded components. Those in the art will appreciate that the denaturing technique employed is generally not limiting unless it inhibits or appreciably interferes with a subsequent amplifying and/or detection step.

Ligation: The term "ligating," or forms thereof, is used herein to refer to an enzymatic ligation process that uses a polypeptide comprising double-strand specific RNA ligase activity in which an inter-nucleotide linkage is formed between immediately adjacent ends of oligonucleotides that are adjacently hybridized to a template. Formation of the linkage is double-strand dependent and specific, also termed duplex-dependent and specific or template-dependent and specific. The internucleotide linkage can include, but is not limited to, phosphodiester bond formation between a 3'-ribonucleoside and a 5'-ribonucleotide, or a 3'-ribonucleoside and a 5'-deoxyribonucleoside. The term "double-strand specific RNA ligase" as used herein refers to a polypeptide comprising RNA ligase activity that preferentially seals or ligates a nick between an oligonucleotide having a 3'-terminal ribonucleotide and an oligonucleotide having a 5' phosphate group, specifically when the oligonucleotides are immediately adjacently hybridized to a template molecule. For example, but without limitation, a nick between the 3'-end of the first oligonucleotide of the first adaptor and the RNA molecule to which the first adaptor is annealed is schematically presented as ligation junction 24 in FIG. 2B.

In certain embodiments, the polypeptide comprising double-strand specific RNA ligase activity is an Rnl2 family ligase exemplified by the bacteriophage T4 RNA ligase 2 (T4 Rnl2), including without limitation, an enzymatically active mutant or variant of Rnl2. T4 Rnl2 is a prototype ligase for an RNA ligase family that differs from the Rnl1 family of ligases due to variant nucleotidyl transferase motifs (see, e.g., Ho and Shuman, *Proc. Natl. Acad. Sci.* 99(20):12709-14 (2002); and Yin et al., *J. Biol. Chem.* 278:17601-08 (2003)). The T4 Rnl2 family includes vibriophage KVP40 Rnl2, the RNA-editing ligases (RELs) of *Trypanosoma brucei* (TbREL1 and TbREL2) and of *Leishmania tarentolae* (LtREL1 and LtREL2), poxvirus AmEPV (entomopoxvirus) ligase, baculovirus AcNPV ligase, and baculovirus XcGV ligase, among others. In some embodiments using REL ligases, the second and fourth oligonucleotides can comprise ribonucleotides and, in certain embodiments, the single stranded portions of the second and fourth oligonucleotides can comprise ribonucleotides.

T4 Rnl2 ligase is commercially available from NEW ENGLAND BIOLABS® (Ipswich, Mass.) or the ligase can be isolated as described in Nandakumar et al., *JBC* 280(25): 23484-23489, 2005; Nandakumar et al., *JBC* 279(30):31337-31347, 2004; and Nandakumar et al., *Molecular Cell* 16:211-221, 2004. The T4 Rnl2 enzyme is encoded by gene gp24.1 of phage T4. In certain embodiments, a polypeptide comprising ligase activity comprises T4 Rnl2 or another member of the Rnl2 family of ligases, or an enzymatically active mutant or variant thereof.

In certain embodiments, the polypeptide comprising double-strand specific RNA ligase activity is a *Deinococcus radiodurans* RNA ligase (DraRnl) (Raymond et al., *Nucl Acids Res* 35(3):839-849, 2007), or a DraRnl-type ligase, including without limitation, a ligase having Gen Bank accession no. XP_367846 from the fungi *Magnaporthe grisea*, Gen Bank accession no. CAE76396 from *Neurospora crassa*, accession no. XP_380758 from *Gibberella zeae*, or Accession no. EAL61744 from the amoeba *Dictyostelium discoideum*. In some embodiments, a ligase can include a combination of any of the above-cited ligases, or enzymatically active mutants or variants thereof.

In certain embodiments, a polypeptide comprising double-strand specific RNA ligase activity can be preadenylated, the 5'-terminal nucleotide of the third oligonucleotide can be preadenylated, or the 5'-terminal nucleotide of the RNA molecule to be detected can be preadenylated, or a combination thereof. Ho et al. (*Structure* 12:327-339) sets forth a mechanism for T4 Rnl2 where the C-terminal domain thereof functions in sealing 3'-OH and 5'-P RNA ends. The N-terminal segment (1-249) of the Rnl2 protein is reported to function as an autonomous adenylyltransferase/App-RNA ligase domain. In general, RNA ligases join 3'-OH and 5'-$PO_4$ RNA termini through a series of three nucleotidyl transfer steps involving activated covalent intermediates. RNA ligase reacts with ATP to form a covalent ligase-AMP intermediate plus pyrophosphate. AMP is then transferred from ligase-adenylate to a 5'-$PO_4$ RNA end to form an RNA-adenylate intermediate (AppRNA). Ligase then catalyzes attack by an RNA 3'-OH on the RNA-adenylate to seal the two ends via a phosphodiester bond and release AMP. Mechanisms for RNA ligation are further discussed by Nandakumar et al. (ibid 2005, 2004a, 2004b) Yin et al. (*JBC* 278:20, 17601-17608; *Virology* 319:141-151, 2004), Ho et al. (ibid; *PNAS*, 99:20, 12709-12714, 2002), Gumport et al. (in *Gene Amplification and Analysis*, Vol 2, edited by Chirikjian, J. G., and Papas, T. S., 1981, 313-345) and by Raymond et al. (*Nucleic Acids Res.* 35:3, 839-849, 2007). Preadenylated agents such as ligase-adenylate, RNA-adenylate, or a chimeric DNA/RNA-adenylate are contemplated for use in some embodiments of the current teachings.

According to certain embodiments, at least one species of first adaptor, at least one species of second adaptor, at least one species of RNA molecule, and a polypeptide comprising double-strand specific RNA ligase activity are combined in a ligation reaction composition. It is to be appreciated that the adaptors of the current teachings are each ligated with the corresponding RNA molecule in the same reaction composition during the same incubation period, that is simultaneously or nearly simultaneously, in contrast to other techniques in which one adaptor is ligated to one end of an RNA molecule of interest in one reaction, then another adaptor is ligated or incorporated onto the opposite side of the same RNA molecule of interest in a second reaction, often with an intervening gel purification, phosphorylation, or reverse transcription step (see, e.g., Elbashir et al., *Genes and Development* 15:188-200, 2001; Ambros and Lee, *Methods in Mol. Biol.* 265:131-58, 2004; Berezikov et al., *Nature Genet. Supp.* 38:S2-S7, 2006; Takada et al., *Nucl. Acids Res.* 34(17):e115, 2006; Michael, *Methods in Mol. Biol.* 342:189-207, 2006; and Takada and Mano, *Nature Protocols* 2(12):3136-45, 2007). It is to be understood that, with respect to the current teachings, the order of adding components to the ligation reaction composition is generally not significant and is intended to be encompassed within the term "forming a ligation reaction composition" or similar terms used herein, unless expressly stated otherwise. Thus, the sequential addition of one adaptor (for example, a first adaptor) to a reaction composition comprising RNA molecules and a ligase, followed by the subsequent addition of the other adaptor (in this example, the second adaptor) to that reaction composition is within the intended scope of the instant teachings, regardless of whether there is an incubation step between the addition of one adaptor and the addition of the other adaptor.

Reverse Transcription: In some embodiments, detecting the RNA molecule comprises reverse transcribing the ligated product to form a reverse transcribed product. The terms "reverse transcribing" and "reverse transcription" and forms thereof as used herein refer to the process of generating a double-stranded RNA-DNA hybrid molecule, starting with the ligated product, based on the sequential catalytic addition of deoxyribonucleotides or analogs of deoxyribonucleotides to the hybrid molecule in a template dependent manner using a polypeptide having RNA-directed DNA polymerase transcription activity. According to the current teachings, the fourth oligonucleotide of the second adaptor can serve as the primer for reverse transcribing the ligation product to generate the reverse transcribed product. Addition of a separate primer for reverse transcription, therefore, is not necessary.

In some embodiments, the polypeptide having RNA-directed DNA polymerase transcription activity comprises MMLV reverse transcriptase, including enzymatically active mutants or variants thereof, for example but not limited to, ArrayScript™ reverse transcriptase (Ambion), SuperScript™ reverse transcriptase (Invitrogen); or a polypeptide comprising reverse transcription activity but that has decreased RNAse H activity when compared to the corresponding wild-type reverse transcriptase, for example but not limited to, an "RNase H minus" mutant, such as RNase H-minus HIV-1 reverse transcriptase (Wu et al., J. Virol. 73(6): 4794-4805, 1999).

In some embodiments, the RNA-directed DNA polymerase transcription activity can be carried out by a DNA-directed DNA polymerase that possesses RNA-directed DNA polymerase activity under certain reaction conditions, for example but not limited to, Tth DNA polymerase and DNA polymerase I from *Carboxydothermus hydrogenoformans*.

Ribonuclease H Digestion: In some embodiments, the reverse transcribed product is digested with ribonuclease H to remove at least some of the ribonucleosides to form an amplification template. The term "digesting", particularly in reference to a ribonuclease, refers to the catalysis of RNA into smaller components, for example but not limited to, cleavage of the RNA strand of the reverse transcribed product by RNase H to generate a single-stranded or substantially single-stranded cDNA molecule that can serve as an amplification template of the current teachings.

Amplification: The terms "amplifying" and "amplification" are used in a broad sense and refer to any technique by which at least a part of an amplification template, at least part of an amplified product, or both, is reproduced or copied (including the synthesis of a complementary copy), typically in a template-dependent manner, including without limitation, a broad range of techniques for amplifying nucleic acid sequences, either linearly or exponentially. Some non-limiting examples of amplification techniques include the polymerase chain reaction (PCR) including without limitation, reverse transcription PCR (RT-PCR), asynchronous primer PCR, emulsion PCR (ePCR), quantitative PCR (qPCR), and asymmetric PCR, primer extension, strand displacement amplification (SDA), multiple displacement amplification (MDA), nucleic acid strand-based amplification (NASBA), rolling circle amplification (RCA), transcription-mediated amplification (TMA), transcription, and the like, including multiplex versions or combinations thereof. Descriptions of such techniques can be found in, among other places, Sambrook and Russell ibid.; Sambrook et al.; Ausubel et al.; PCR Primer: A Laboratory Manual, Diffenbach, Ed., Cold Spring Harbor Press (1995); The Electronic Protocol Book, Chang Bioscience (2002); Msuih et al., *J. Clin. Micro.* 34:501-07 (1996); McPherson and Moller, PCR The Basics, Bios Scientific Publishers, Oxford, U.K., 2000 ("McPherson"); Rapley, The Nucleic Acid Protocols Handbook (2000), Humana Press, Totowa, N.J. ("Rapley"); U.S. Pat. Nos. 6,027,998 and 6,511,810; PCT Publication Nos. WO 97/31256 and WO 01/92579; Ehrlich et al., *Science* 252:1643-50 (1991); Innis et al., PCR Protocols: A Guide to Methods and Applications, Academic Press (1990); Favis et al., *Nature Biotechnology* 18:561-64 (2000); Williams et al., *Nature Methods* 3(7):545-50 (2006); and Rabenau et al., *Infection* 28:97-102 (2000).

Amplification can comprise thermocycling (sometimes referred to as cycling or thermal cycling) or can be performed isothermally. In certain embodiments, amplifying comprises at least one cycle, and typically multiple cycles, of the sequential steps of: hybridizing a primer with a complementary or substantially complementary sequence of an amplification template, an amplified product, or the complement of either; synthesizing a strand of nucleotides in a template-dependent manner using a polymerase; and denaturing the newly-formed nucleic acid duplex to separate the strands. The cycle may or may not be repeated, as desired. In some embodiments, amplifying comprises a cycling the amplification reaction composition in a thermocycler, for example but not limited to a GeneAmp® PCR System 9700, 9600, 2700, or 2400 thermocycler (all from Applied Biosystems). In certain embodiments, newly-formed nucleic acid duplexes are not initially denatured, but are used in their double-stranded form in one or more subsequent steps and either or both strands can, but need not, serve as a surrogate for the corresponding RNA molecule of interest. In certain embodiments, single-stranded amplicons are generated, for example but not limited to asymmetric PCR, asynchronous PCR, or transcription.

Primer extension is an amplifying technique that comprises elongating a primer that is annealed to a template in the 5'=>3' direction using an extending enzyme such as a polymerase to form an extension product, for example but not limited to reverse transcribing a ligated product or amplifying an amplification template or an amplified product. According to certain embodiments, with appropriate buffers, salts, pH, temperature, and nucleotide triphosphates, a polymerase incorporates nucleotides complementary to the template strand starting at the 3'-end of an annealed primer, to generate a complementary strand. In certain embodiments, the polymerase used for primer extension lacks or substantially lacks 5'-exonuclease activity.

In some embodiments, the amplification template is combined with at least one forward primer, at least one reverse primer, and a polypeptide having DNA-directed DNA polymerase activity to form an amplification reaction composition.

The term "DNA polymerase" is used in a broad sense herein and refers to any polypeptide that is able to catalyze the addition of deoxyribonucleotides or analogs of deoxyribonucleotides to a nucleic acid polymer in a template dependent manner for example, but not limited to, the sequential addition of deoxyribonucleotides to the 3'-end of a primer that is annealed to a nucleic acid template during a primer extension reaction. Typically DNA polymerases include DNA-directed DNA polymerases and RNA-directed DNA polymerases, including reverse transcriptases. Some reverse transcriptases possess DNA-directed DNA polymerase activity under certain reaction conditions, including AMV reverse transcriptase and MMLV reverse transcriptase. Some DNA-directed DNA polymerases possess reverse transcriptase under certain reaction conditions, for example, but not limited to *Thermus thermophilus* (Tth) DNA polymerase. Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005 (hereinafter "Ausubel et al."); Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis. Expressly within the intended scope of the terms DNA-directed DNA polymerase and RNA-directed DNA polymerase are enzymatically active mutants or variants thereof, including enzymes modified to confer different temperature-sensitive properties (see, e.g., U.S. Pat. Nos. 5,773,258; 5,677,152; and 6,183,998; and *DNA Amplification: Current Techniques and Applications*, Demidov and Broude, eds., Horizon Bioscience, 2004, particularly in Chapter 1.1).

Enzymatically Active Mutants or Variants of Enzymes: For the purposes of the current teachings, when a specific enzyme or a polypeptide comprising enzymatic activity is described or claimed, enzymatically active mutants or variants of that enzyme/polypeptide are intended to be included, unless specifically stated otherwise. For illustration purposes but not as a limitation, when the terms "Rnl2" or "Rnl2 ligase" are used in this specification or the appended claims, the naturally-occurring or wild-type Rnl2 ligase as well as all enzymatically active mutants or variants of Rnl2 ligase are intended to be included, unless specifically stated otherwise. Similarly, an RNA-directed DNA polymerase, a ribonuclease, or a DNA-directed DNA polymerase, is considered an equivalent to an enzymatically active mutant or variant thereof. The term "enzymatically active mutant or variant thereof," refers to one or more polypeptides derived from the corresponding enzyme that retains at least some of the desired enzymatic activity, such as ligating, reverse transcribing, digesting, amplifying, or as appropriate. Also within the scope of this term are: enzymatically active fragments, including but not limited to, cleavage products, for example but not limited to Klenow fragment, Stoffel fragment, or recombinantly expressed fragments and/or polypeptides that are smaller in size than the corresponding enzyme; mutant forms of the corresponding enzyme, including but not limited to, naturally-occurring mutants, such as those that vary from the "wild-type" or consensus amino acid sequence, mutants that are generated using physical and/or chemical mutagens, and genetically engineered mutants, for example but not limited to random and site-directed mutagenesis techniques; amino acid insertions and deletions, truncated forms, and changes due to nucleic acid nonsense mutations, missense mutations, and frameshift mutations (see, e.g., Sriskanda and Shuman, *Nucl. Acids Res.* 26(2):525-31, 1998; Odell et al., *Nucl. Acids Res.* 31(17):5090-5100, 2003); reversibly modified nucleases, ligases, and polymerases, for example but not limited to those described in U.S. Pat. No. 5,773,258; biologically active polypeptides obtained from gene shuffling techniques (see, e.g., U.S. Pat. Nos. 6,319,714 and 6,159,688), splice variants, both naturally occurring and genetically engineered, provided that they are derived, at least in part, from one or more corresponding enzymes; polypeptides corresponding at least in part to one or more such enzymes that comprise modifications to one or more amino acids of the native sequence, including without limitation, adding, removing or altering glycosylation, disulfide bonds, hydroxyl side chains, and phosphate side chains, or crosslinking, provided such modified polypeptides retain at least some of the desired catalytic activity; and the like. Expressly within the meaning of the term "enzymatically active mutants or variants thereof" when used in reference to a particular enzyme(s) are enzymatically active mutants of that enzyme, enzymatically active variants of that enzyme, or enzymatically active mutants of that enzyme and enzymatically active variants of that enzyme.

The skilled artisan will readily be able to measure enzymatic activity using an appropriate assay known in the art. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups, such as disclosed herein. Protocols for such assays may be found, among other places, in Sambrook et al., *Molecular Cloning, A Laboratory Manual*, Cold Spring Harbor Press (1989) (hereinafter "Sambrook et al."), Sambrook and Russell, editors, *Molecular Cloning*, Vol 3, 3rd edition, Cold Spring Harbor Press (2001), Ausubel et al., and Housby and Southern, *Nucl. Acids Res.* 26:4259-66, 1998) and the references cited below for the family of Rnl2 ligases.

Amplification Primers: The term "primer" refers to a polynucleotide that selectively hybridizes to a corresponding primer-binding site of an amplification template, an amplified product, or both; and allows the synthesis of a sequence complementary to the corresponding polynucleotide template from its 3' end. A "primer pair" comprises a forward primer and a reverse primer that anneal to one strand of an amplification product or its complement. Primer pairs are particularly useful in certain exponential amplification techniques, such as the polymerase chain reaction. In certain embodiments, a forward primer and the corresponding reverse primer of a primer pair have different melting temperatures (Tm) to permit asynchronous primer PCR.

As used herein, "forward" and "reverse" are used to indicate relative orientation of primers on a polynucleotide sequence such as an amplification template or an amplified product. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward" primer is designed to anneal with the complement of the upstream primer-binding site at or near the "5'-end" of the polynucleotide in a 5' to 3' "forward" orientation, left to right. Thus, the reverse primer comprises a sequence that is complementary to the "reverse" or downstream primer-binding site of the polynucleotide and the forward primer comprises a sequence that is the same as the forward or upstream primer-binding site. It is to be understood that the terms "3-end" and "5'-end" as used in this paragraph are illustrative only and do not necessarily refer literally to the respective ends of the polynucleotide, as such primer-binding sites may be located internally. Rather, the only limitation is that the reverse primer of this exemplary primer pair anneals with a reverse primer-binding site that is downstream or to the right of the forward primer-binding site that comprises the same sequence as the corresponding forward primer. As will be recognized by those of skill in the art, these terms are not intended to be limiting, but rather to provide illustrative orientation in a given embodiment.

A primer may comprise a nucleotide sequence of an adaptor oligonucleotide or a nucleotide sequence corresponding to an adaptor oligonucleotide. For example, forward primer having SEQ ID NO:5 comprises the sequence of first oligonucleotide having SEQ ID NO:1 (with T's instead of U's). Some embodiments of relationships between primers and adaptor sequences can be understood by the schematic of FIG. 15 in which arrows depict variously, forward and reverse PCR primers or forward and reverse SYBR primers. P1 and P2 refer to primer portions.

As used herein, the term "primer-binding site" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer-binding sites are present on a single polynucleotide (for example but not limited to a first extension product or a second extension product), the orientation of the two primer-binding sites is generally different. For example, one primer of a primer pair is complementary to and can hybridize with to the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. In addition, "universal" primers and primer-binding sites as used herein are generally chosen to be as unique as possible given the particular assays and host genomes to ensure specificity of the assay.

In some embodiments, a primer and/or an amplified product comprises a "promoter sequence", including without limitation a sequence suitable for initiating transcription using a suitable polymerase, for example but not limited to, T3 RNA polymerase, T7 RNA polymerase, or SP6 RNA polymerase. Some embodiments of the current teachings employ a "promoter-primer" in a method of incorporating a promoter sequence into an amplification product. In some embodiments, a promoter sequence comprises a multiplicity of different sequences suitable for binding an RNA polymerase, for example but not limited to a first sequence suitable for binding a first RNA polymerase and a second sequence suitable for binding a second RNA polymerase. Those in the art understand that as an amplification product comprising a promoter sequence is amplified by certain amplification methods, the complement of the promoter sequence may be synthesized in the complementary amplicon. Thus, it is to be understood that the complement of a promoter sequence is expressly included within the intended meaning of the term promoter sequence, as used herein. Some embodiments of the disclosed methods and kits employ a "promoter-primer" in methods of incorporating a desired promoter sequence into an amplification product.

Those in the art understand that as an amplified product is amplified by certain amplification methods, the complement of the primer-binding site is synthesized in the complementary amplicon. Thus, it is to be understood that the complement of a primer-binding site is expressly included within the intended meaning of the term primer-binding site, as used herein.

In some embodiments, the amplification methods of the current teachings comprise a Q-PCR reaction. The terms "quantitative PCR", "real time PCR", or "Q-PCR" refer to a variety of methods used to quantify the results of the polymerase chain reaction for specific nucleic acid sequences. Such methods typically are categorized as kinetics-based systems that generally determine or compare the amplification factor, such as determining the threshold cycle (CT), or as co-amplification methods, that generally compare the amount of product generated from simultaneous amplification of target and standard templates. Many Q-PCR techniques comprise reporter probes, intercalating agents, or both. For example but not limited to TaqMan® probes (Applied Biosystems), i-probes, molecular beacons, Eclipse probes, scorpion primers, Lux™ primers, FRET primers, ethidium bromide, SYBR® Green I (Molecular Probes), and PicoGreen® (Molecular Probes). In some embodiments, detecting comprises a real-time detection instrument. Exemplary real-time instruments include, the ABI PRISM® 7000 Sequence Detection System, the ABI PRISM® 7700 Sequence Detection System, the Applied Biosystems 7300 Real-Time PCR System, the Applied Biosystems 7500 Real-Time PCR System, the Applied Biosystems 7900 HT Fast Real-Time PCR System (all from Applied Biosystems); the LightCycler™ System (Roche Molecular); the Mx3000P™ Real-Time PCR System, the Mx3005P™ Real-Time PCR System, and the Mx4000® Multiplex Quantitative PCR System (Stratagene, La Jolla, Calif.); and the Smart Cycler System (Cepheid, distributed by Fisher Scientific). Descriptions of real-time instruments can be found in, among other places, their respective manufacturer's users manuals; McPherson; DNA Amplification: Current Technologies and Applications, Demidov and Broude, eds., Horizon Bioscience, 2004; and U.S. Pat. No. 6,814,934.

In certain embodiments, an amplification reaction comprises multiplex amplification, in which a multiplicity of different amplification templates, a multiplicity of different amplification product species, or both, are simultaneously amplified using a multiplicity of different primer pairs (see, e.g., Henegariu et al., *BioTechniques* 23:504-11, 1997; and Rapley, particularly in Chapter 79). Certain embodiments of the disclosed methods comprise a single-plex amplification reaction, including without limitation, an amplification reaction comprising a multiplicity of single-plex amplifications performed in parallel, for example but not limited to certain TaqMan® Array configurations wherein approximately 100 nuclease assays are performed in parallel to determine whether specific amplified products are present and in what quantity.

In certain embodiments, an amplifying reaction comprises asymmetric PCR. According to certain embodiments, asymmetric PCR comprises an amplification composition comprising (i) at least one primer pair in which there is an excess of one primer, relative to the corresponding primer of the primer pair, for example but not limited to a five-fold, a ten-fold, or a twenty-fold excess; (ii) at least one primer pair that comprises only a forward primer or only a reverse primer; (iii) at least one primer pair that, during given amplification conditions, comprises a primer that results in amplification of one strand and a corresponding primer that is disabled; or (iv) at least one primer pair that meets the description of both (i) and (iii) above. Consequently, when an amplification template or an amplification product is amplified, an excess of one strand of the subsequent amplification product (relative to its complement) is generated. Descriptions of asymmetric PCR, can be found in, among other places, McPherson, particularly in Chapter 5; and Rapley, particularly in Chapter 64.

In certain embodiments, one may use at least one primer pair wherein the melting temperature ($Tm_{50}$) of one of the primers is higher than the $Tm_{50}$ of the other primer, sometimes referred to as asynchronous primer PCR (A-PCR, see, e.g., U.S. Pat. No. 6,887,664). In certain embodiments, the $Tm_{50}$ of the forward primer is at least 4-15° C. different from the $Tm_{50}$ of the corresponding reverse primer. In certain embodiments, the $Tm_{50}$ of the forward primer is at least 8-15° C. different from the $Tm_{50}$ of the corresponding reverse primer. In certain embodiments, the $Tm_{50}$ of the forward primer is at least 10-15° C. different from the $Tm_{50}$ of the corresponding reverse primer. In certain embodiments, the $Tm_{50}$ of the forward primer is at least 10-12° C. different from the $Tm_{50}$ of the corresponding reverse primer. In certain embodiments, in at least one primer pair, the $Tm_{50}$ of a forward primer differs from the $Tm_{50}$ of the corresponding reverse primer by at least about 4° C., by at least about 8° C., by at least about 10° C., or by at least about 12° C.

In certain amplifying embodiments, in addition to the difference in $Tm_{50}$ of the primers in a primer pair, there is also an excess of one primer relative to the other primer in the primer pair. In certain embodiments, there is a five- to twenty-fold excess of one primer relative to the other primer in the primer pair. In certain embodiments of A-PCR, the primer concentration is at least 50 nM.

In A-PCR according to certain embodiments, one may use conventional PCR in the first cycles of amplification such that both primers anneal and both strands of a double-stranded amplicon are amplified. By raising the temperature in subsequent cycles of the same amplification reaction, however, one may disable the primer with the lower $T_m$ such that only one strand is amplified. Thus, the subsequent cycles of A-PCR in which the primer with the lower $T_m$ is disabled result in asymmetric amplification. Consequently, when the target region or an amplification product is amplified, an excess of one strand of the subsequent amplification product (relative to its complement) is generated.

According to certain embodiments of A-PCR, the level of amplification can be controlled by changing the number of cycles during the first phase of conventional PCR cycling. In such embodiments, by changing the number of initial conventional cycles, one may vary the amount of the double-stranded amplification products that are subjected to the subsequent cycles of PCR at the higher temperature in which the primer with the lower $T_m$ is disabled.

In certain embodiments, amplifying comprises in vitro transcription. In some embodiments, a first adaptor, a second adaptor, a first primer, a second primer, or combinations thereof, comprise a promoter sequence or its complement, for example but not limited to, a promoter-primer. In some embodiments, a reverse transcribed product comprising a promoter or an amplified product comprising a promoter is combined with ribonucleotide triphosphates, an appropriate buffer system, and a suitable RNA polymerase, for example but not limited to, SP6, T3, or T7 RNA polymerase and amplified RNA (aRNA) are generated according to known methods. The aRNA may be used for array analysis, such as microarray or bead array analysis, wherein the sequence and quantity of the aRNA species can be determined. Thus, in certain embodiments, such aRNA serves as a surrogate for the corresponding RNA molecule.

Certain methods of optimizing amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the primers used. For example, the length of the primers, as well as the G-C:A-T ratio may alter the efficiency of primer annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. September 2004, Promega Corp., Madison, Wis.

Purifying the amplified product according to the present teachings comprises any process that removes at least some unligated adaptors, unligated RNA molecules, byproducts, primers, enzymes or other components of the ligation reaction composition, the amplification reaction composition, or both following at least one cycle of amplification. Such processes include, but are not limited to, molecular weight/size exclusion processes, e.g., gel filtration chromatography or dialysis, sequence-specific hybridization-based pullout methods, affinity capture techniques, precipitation, adsorption, gel electrophoresis, conventional cloning, conventional cloning with concatamerization, or other nucleic acid purification techniques. In some embodiments purifying the amplified product comprises gel electrophoresis, including without limitation, polyacrylamide gel electrophoresis (PAGE) and/or agarose gel electrophoresis. In certain embodiments, the amplified product is purified using high-performance liquid chromatography (HPLC; sometimes also referred to as high-pressure liquid chromatography).

Detection: The RNA molecule of interest is detected by detecting the ligated product or a surrogate thereof. In some embodiments, the ligated product is reverse transcribed as described above and the reverse transcribed product is placed on an array and detected using standard methods known by one of skill in the art. In some embodiments, the reverse transcribed product is labeled with biotin and detection is by using streptavidin binding thereto. In some embodiments, the reverse transcribed product is purified using glass fiber filters, beads or is gel-purified. In some embodiments, the reverse transcribed product is combined with a peptide comprising ribonuclease activity to form a digestion reaction composition and incubated under conditions suitable for digesting at least some of the ribonucleosides from the reverse transcribed product to form an amplification template.

The terms "detecting" and "detection" are used in a broad sense herein and encompass any technique by which one can determine whether or not a particular RNA molecule i.e., an RNA molecule of interest, is present in a sample. In some embodiments, the presence of a surrogate is detected, directly or indirectly, allowing the presence or absence of the corresponding RNA molecule to be determined. For example, the presence of a surrogate is detected by detecting a family of labeled sequencing products obtained using an amplified product or a ligated product as the template; or detecting the fluorescence generated when a nuclease reporter probe, annealed to an amplified product, is cleaved by a polymerase, wherein the detectable signal or detectable change in signal indicates that the corresponding amplified product and/or ligated product has been amplified and thus the corresponding RNA molecule is present in the sample. In some embodiments, detecting comprises quantitating the detectable signal, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products. In some embodiments, detecting an RNA molecule comprises a nucleic acid dye, for example but not limited to, in a Q-PCR reaction composition. Those in the art will understand that the ligated products, reverse transcribed products, amplification templates, and amplified sequences each serve as a surrogate for the RNA molecule from which they were directly or indirectly generated and that by detecting any of these products one is directly or indirectly detecting the corresponding RNA molecule.

The term "reporter probe" refers to a sequence of nucleotides, nucleotide analogs, or nucleotides and nucleotide analogs, that specifically anneals with a corresponding amplicon, for example but not limited to a PCR product, and when detected, including but not limited to a change in intensity or of emitted wavelength, is used to identify, detect, and/or quantify the corresponding amplicon and thus the corresponding RNA molecule. Thus, by indirectly detecting the amplicon, one can determine that the corresponding RNA molecule is present in the sample. Most reporter probes can be categorized based on their mode of action, for example but not limited to: nuclease probes, including without limitation TaqMan® probes; extension probes including without limitation scorpion primers, Lux™ primers, Amplifluors, and the like; and hybridization probes including without limitation molecular beacons, Eclipse® probes, light-up probes, pairs of singly-labeled reporter probes, hybridization probe pairs, and the like. In certain embodiments, reporter probes comprise an amide bond, a locked nucleic acid (LNA), a universal base, or combinations thereof, and can include stem-loop and stemless reporter probe configurations. Certain reporter probes are singly-labeled, while other reporter probes are doubly-labeled. Dual probe systems that comprise FRET between adjacently hybridized probes are within the intended scope of the term reporter probe. In certain embodiments, a reporter probe comprises a fluorescent reporter group and a quencher (including without limitation dark quenchers and fluorescent quenchers). Some non-limiting examples of reporter probes include TaqMan® probes; Scorpion probes (also referred to as scorpion primers); Lux™ primers; FRET primers; Eclipse® probes; molecular beacons, including but not limited to FRET-based molecular beacons, multicolor molecular beacons, aptamer beacons, PNA beacons, and antibody beacons; labeled PNA clamps, labeled PNA openers, labeled LNA probes, and probes comprising nanocrystals, metallic nanoparticles and similar hybrid probes (see, e.g., Dubertret et al., *Nature Biotech*. 19:365-70, 2001; Zelphati et al., *BioTechniques* 28:304-15, 2000). In certain embodiments, reporter probes further comprise minor groove binders including but not limited to TaqMan® MGB probes and TaqMan® MGB-NFQ probes (both from Applied Biosystems). In certain embodiments, reporter probe detection comprises fluorescence polarization detection (see, e.g., Simeonov and Nikiforov, *Nucl. Acids Res*. 30:e91, 2002).

The term "reporter group" is used in a broad sense herein and refers to any identifiable tag, label, or moiety. The ordinarily skilled artisan will appreciate that many different species of reporter groups can be used in the present teachings, either individually or in combination with one or more different reporter group. In certain embodiments, a reporter group emits a fluorescent, a chemiluminescent, a bioluminescent, a phosphorescent, or an electrochemiluminescent signal. Some non-limiting examples of reporter groups include fluorophores, radioisotopes, chromogens, enzymes, antigens including but not limited to epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer-compatible reporter groups, such as mass tags, charge tags, and isotopes (see, e.g., Haff and Smirnov, *Nucl. Acids Res*. 25:3749-50, 1997; Xu et al., *Anal. Chem*. 69:3595-3602, 1997; Sauer et al., *Nucl. Acids Res*. 31:e63, 2003).

The term reporter group also encompasses an element of multi-element reporter systems, including without limitation, affinity tags such as biotin:avidin, antibody:antigen, and the like, in which one element interacts with one or more other elements of the system in order to effect the potential for a detectable signal. Some non-limiting examples of multi-element reporter systems include an oligonucleotide comprising a biotin reporter group and a streptavidin-conjugated fluorophore, or vice versa; an oligonucleotide comprising a DNP reporter group and a fluorophore-labeled anti-DNP antibody; and the like. Detailed protocols for attaching reporter groups to nucleic acids can be found in, among other places, Hermanson, *Bioconjugate Techniques*, Academic Press, San Diego, 1996; *Current Protocols in Nucleic Acid Chemistry*, Beaucage et al., eds., John Wiley & Sons, New York, N.Y. (2000), including supplements through April 2005; and Haugland, *Handbook of Fluorescent Probes and Research Products*, 9$^{th}$ ed., Molecular Probes, 2002.

Multi-element interacting reporter groups are also within the intended scope of the term reporter group, such as fluorophore-quencher pairs, including without limitation fluorescent quenchers and dark quenchers (also known as non-fluorescent quenchers). A fluorescent quencher can absorb the fluorescent signal emitted from a fluorophore and after absorbing enough fluorescent energy, the fluorescent quencher can emit fluorescence at a characteristic wavelength, e.g., fluorescent resonance energy transfer (FRET). For example without limitation, the FAM™-TAMRA™ dye pair can be illuminated at 492 nm, the excitation peak for FAM™ dye, and emit fluorescence at 580 nm, the emission peak for TAMRA™ dye. A dark quencher, appropriately paired with a fluorescent reporter group, absorbs the fluorescent energy from the fluorophore, but does not itself fluoresce. Rather, the dark quencher dissipates the absorbed energy, typically as heat. Some non-limiting examples of dark or nonfluorescent quenchers include Dabcyl, Black Hole Quenchers, Iowa Black, QSY-7, AbsoluteQuencher, Eclipse® non-fluorescent quencher, metal clusters such as gold nanoparticles, and the like. Certain dual-labeled probes comprising fluorophore-quencher pairs can emit fluorescence when the members of the pair are physically separated, for example but without limitation, nuclease probes such as TaqMan® probes. Other dual-labeled probes comprising fluorophore-quencher pairs can emit fluorescence when the members of the pair are spatially separated, for example but not limited to hybridization probes such as molecular beacons or extension probes such as Scorpion™ primers. Fluorophore-quencher pairs are well known in the art and used extensively for a variety of reporter probes (see, e.g., Yeung et al., *BioTechniques* 36:266-75, 2004; Dubertret et al., *Nat. Biotech*. 19:365-70, 2001; and Tyagi et al., *Nat. Biotech*. 18:1191-96, 2000).

The term "nucleic acid dye" as used herein refers to a fluorescent molecule that is specific for a double-stranded polynucleotide or that emits a substantially greater fluorescent signal when associated with a double-stranded polynucleotide than with a single-stranded polynucleotide. Typically nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a nalthalene diimide derivative carrying two fluorescent tetradentate β-diketone-Eu3+ chelates (NDI-(BHHCT-Eu$^{3+}$)$_2$), see, e.g., Nojima et al., *Nucl. Acids Res*. Supplement No. 1, 105-06 (2001)), ethidium bromide, and certain unsymmetrical cyanine dyes such as SYBR® Green, SYBR® Gold, PicoGreen®, and BOXTO.

In certain embodiments, detecting comprises an instrument, i.e., using an automated or semi-automated detecting device that can, but need not comprise a computer algorithm. In certain embodiments, a detecting instrument comprises or is coupled to a device for graphically displaying the intensity of an observed or measured parameter of an extension product or its surrogate on a graph, monitor, electronic screen, magnetic media, scanner print-out, or other two- or three-dimensional display and/or recording the observed or measured parameter. In certain embodiments, the detecting step is combined with or is a continuation of at least one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; or a microarray with a data recording device such as a scanner or CCD camera. In certain embodiments, the detecting step is combined with an amplifying step, for example but not limited to, real-time analysis such as Q-PCR. Exemplary systems for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, among others (see also Gerry et al., *J. Mol. Biol.* 292:251-62, 1999; De Bellis et al., *Minerva Biotec* 14:247-52, 2002; and Stears et al., *Nat. Med.* 9:140-45, including supplements, 2003) or bead array platforms (Illumina, San Diego, Calif.). Exemplary software includes GeneMapper™ Software, GeneScan® Analysis Software, and Genotyper® software (all from Applied Biosystems).

In certain embodiments, an RNA molecule can be detected and quantified based on the mass-to-charge ratio (m/z) of at least a part of an amplified product and/or a ligated product. For example, in some embodiments, a primer or an adapter comprises a mass spectrometry-compatible reporter group, including without limitation, mass tags, charge tags, cleavable portions, or isotopes that are incorporated into an amplified product and can be used for mass spectrometer detection (see, e.g., Haff and Smirnov, *Nucl. Acids Res.* 25:3749-50, 1997; and Sauer et al., *Nucl. Acids Res.* 31:e63, 2003). An amplified product can be detected by mass spectrometry allowing the presence or absence of the corresponding RNA molecule to be determined. In some embodiments, a primer or an adaptor comprises a restriction enzyme site, a cleavable portion, or the like, to facilitate release of a part of an amplified product for detection. In certain embodiments, a multiplicity of amplified products are separated by liquid chromatography or capillary electrophoresis, subjected to ESI or to MALDI, and detected by mass spectrometry. Descriptions of mass spectrometry can be found in, among other places, *The Expanding Role of Mass Spectrometry in Biotechnology*, Gary Siuzdak, MCC Press, 2003.

In certain embodiments, surrogates such as a reporter probe or a cleaved portion of a reporter probe are detected, directly or indirectly. For example but not limited to, hybridizing an amplified product to a reporter probe comprising a quencher, including without limitation, a molecular beacon, including stem-loop and stem-free beacons, a TaqMan® probe or other nuclease probe, a LightSpeed™ PNA probe, or a microarray capture probe. In certain embodiments, the hybridization occurs when the molecular beacon and the amplified product are free in solution and a detectable signal or a detectably different signal is emitted. In other embodiments, an amplified product hybridizes to or is bound to a solid surface such as a microarray and a detectable signal or a detectably different signal is emitted (see, e.g., EviArrays™ and EviProbes™, Evident Technologies).

In certain embodiments, detecting comprises measuring or quantifying the detectable signal of a reporter group or the change in a detectable signal of a reporter group, typically due to the presence of an amplified product. For illustration purposes but not as a limitation, an unhybridized reporter probe may emit a low level, but detectable signal that quantitatively increases when hybridized with the amplified product, including without limitation, certain molecular beacons, LNA probes, PNA probes, and light-up probes (see, e.g., Svanik et al., *Analyt. Biochem.* 281:26-35, 2000; Nikiforov and Jeong, *Analyt. Biochem.* 275:248-53, 1999; and Simeonov and Nikiforov, *Nucl. Acids Res.* 30:e91, 2002). In certain embodiments, detecting comprises measuring fluorescence polarization.

In some embodiments, determining whether a particular RNA molecule is present in a sample comprises evaluating an internal standard or a control sequence, such as a standard curve for the corresponding target region, an internal size standard, or combinations thereof. In some embodiments, a control sequence or an internal reference dye is employed to account for lane-to-lane, capillary-to-capillary, and/or assay-to-assay variability. In certain embodiments, an internal control sequence comprises an unrelated nucleic acid that is amplified in parallel to validate the amplification reaction or the detection technique.

Those in the art understand that the detection techniques employed are generally not limiting. Rather, a wide variety of detection methods are within the scope of the disclosed methods and kits, provided that they allow the presence or absence of an RNA molecule in the sample to be determined.

In some embodiments, the disclosed methods and kits comprise a microfluidics device, "lab on a chip", or micrototal analytical system (pTAS). In some embodiments, sample preparation is performed using a microfluidics device. In some embodiments, an amplification reaction is performed using a microfluidics device. In some embodiments, a sequencing or Q-PCR reaction is performed using a microfluidic device. In some embodiments, the nucleotide sequence of at least a part of an amplified product is obtained using a microfluidics device. In some embodiments, detecting comprises a microfluidic device, including without limitation, a TaqMan® Low Density Array (Applied Biosystems). Descriptions of exemplary microfluidic devices can be found in, among other places, Published PCT Application Nos. WO/0185341 and WO 04/011666; Kartalov and Quake, *Nucl. Acids Res.* 32:2873-79, 2004; and Fiorini and Chiu, *BioTechniques* 38:429-46, 2005.

Sequencing: In some embodiments, the sequence of at least part of the amplified product is determined thereby detecting the RNA molecule of interest. The term "sequencing" is used in a broad sense herein and refers to any technique known in the art that allows the order of at least some consecutive nucleotides in at least part of a RNA to be identified, including without limitation at least part of an extension product or a vector insert. Some non-limiting examples of sequencing techniques include Sanger's dideoxy terminator method and the chemical cleavage method of Maxam and Gilbert, including variations of those methods; sequencing by hybridization, for example but not limited to, hybridization of amplified products to a microarray or a bead, such as a bead array; pyrosequencing (see, e.g., Ronaghi et al., *Science* 281:363-65, 1998); and restriction mapping. Some sequencing methods comprise electrophoreses, including without limitation capillary electrophoresis and gel electrophoresis; mass spectrometry; and single molecule detection. In some embodiments, sequencing comprises direct sequencing, duplex sequencing, cycle sequencing, single-base extension sequencing (SBE), solid-phase sequencing, or combinations thereof. In some embodiments, sequencing comprises an detecting the sequencing product using an instrument, for example but not limited to an ABI PRISM® 377 DNA Sequencer, an ABI PRISM® 310, 3100, 3100-Avant, 3730, or 3730xl Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR (see, e.g., Williams et al., *Nature Methods* 3(7):545-50, 2006.) In certain embodiments, sequencing comprises a high throughput sequencing technique, for example but not limited to, massively parallel signature sequencing (MPSS). Descriptions of MPSS can be found, among other places, in Zhou et al., *Methods of Molecular Biology* 331:285-311, Humana Press Inc.; Reinartz et al., *Briefings in Functional Genomics and Proteomics*, 1:95-104, 2002; Jongeneel et al., *Genome Research* 15:1007-14, 2005. In some embodiments, sequencing comprises incorporating a dNTP, including without limitation a dATP, a dCTP, a dGTP, a dTTP, a dUTP, a dITP, or combinations thereof and including dideoxyribonucleotide versions of dNTPs, into an amplified product.

Further exemplary techniques that are useful for determining the sequence of at least a portion of a nucleic acid molecule include, without limitation, emulsion-based PCR followed by any suitable massively parallel sequencing or other high-throughput technique. In some embodiments, determining the sequence of at least a part of an amplified product to detect the corresponding RNA molecule comprises quantitating the amplified product. In some embodiments, sequencing is carried out using the SOLiD™ System (Applied Biosystems) as described in, for example, PCT patent application publications WO 06/084132 entitled "Reagents, Methods, and Libraries For Bead-Based Sequencing and WO07/121489 entitled "Reagents, Methods, and Libraries for Gel-Free Bead-Based Sequencing." In some embodiments, quantitating the amplified product comprises real-time or end-point quantitative PCR or both. In some embodiments, quantitating the amplified product comprises generating an expression profile of the RNA molecule to be detected, such as an mRNA expression profile or a miRNA expression profile. In certain embodiments, quantitating the amplified product comprises one or more 5'-nuclease assays, for example but not limited to, TaqMan® Gene Expression Assays and TaqMan® miRNA Assays, which may comprise a microfluidics device including without limitation, a low density array. Any suitable expression profiling technique known in the art may be employed in various embodiments of the disclosed methods.

Those in the art will appreciate that the sequencing method employed is not typically a limitation of the present methods. Rather, any sequencing technique that provides the order of at least some consecutive nucleotides of at least part of the corresponding amplified product or RNA to be detected or at least part of a vector insert derived from an amplified product can typically be used in the current methods. Descriptions of sequencing techniques can be found in, among other places, McPherson, particularly in Chapter 5; Sambrook and Russell; Ausubel et al.; Siuzdak, The Expanding Role of Mass Spectrometry in Biotechnology, MCC Press, 2003, particularly in Chapter 7; and Rapley. In some embodiments, unincorporated primers and/or dNTPs are removed prior to a sequencing step by enzymatic degradation, including without limitation exonuclease I and shrimp alkaline phosphatase digestion, for example but not limited to the ExoSAP-IT® reagent (USB Corporation). In some embodiments, unincorporated primers, dNTPs, and/or ddNTPs are removed by gel or column purification, sedimentation, filtration, beads, magnetic separation, or hybridization-based pull out, as appropriate (see, e.g., ABI PRISM® Duplex™ 384 Well F/R Sequence Capture Kit, Applied Biosystems P/N 4308082).

Those in the art will appreciate that, in certain embodiments, the read length of the sequencing/resequencing technique employed may be a factor in the size of the RNA molecules that can effectively be detected (see, e.g., Kling, *Nat. Biotech.* 21(12):1425-27). In some embodiments, the amplified products generated from the RNA molecules from a first sample are labeled with a first identification sequence (sometimes referred to as a "barcode" herein) or other marker, the amplified products generated from the RNA molecules from a second sample are labeled with a second identification sequence or second marker, and the amplified products comprising the first identification sequence and the amplified products comprising the second identification sequence are pooled prior to determining the sequence of the corresponding RNA molecules in the corresponding samples. In certain embodiments, three or more different RNA libraries, each comprising a identifier sequence that is specific to that library, are combined. In some embodiments, a first adaptor, a second adaptor, a forward primer, a reverse primer, or combinations thereof, comprise an identification sequence or the complement of an identification sequence. In certain embodiments, the identification sequence comprises one of (i) 5'-AAGCCC, (ii) 5'-CACACC, (iii) 5'-CCCCTT, (iv) 5'-CATCGG, (v) 5-TCGTTG, (vi) 5'-GGGCAC, (vii) 5'-CCAGAC, (viii) 5'-CTCCGT, (ix) 5'-CCCTTC, (x) 5'-GCGGTC, or the complement of any one of these sequences (i)-(x). In some embodiments, a reverse primer comprises a sequence of SEQ ID NO:6 or SEQ ID NO:15 to SEQ ID NO:23 as described in Example 11.

Libraries: The present teachings provide compositions, methods and kits for detecting an RNA molecule. According to certain embodiments, a library comprising a multiplicity of different amplified product species is generated wherein at least one species of amplified product corresponds to one species of small RNA present in the sample.

According to certain illustrative embodiments of the instant teachings, for example, a sample comprising a multiplicity of small RNA species, a multiplicity of mRNA species, or both, is combined with a multiplicity of different first adaptor species, a multiplicity of different second adaptor species, and a polypeptide comprising double-strand specific RNA ligase activity to form a ligation reaction composition. In some embodiments, the mRNA is fragmented, depleted of undesired nucleic acid species (for example but not limited to, rRNA, high copy number mRNAs or genomic DNA), or depleted and fragmented. The ligation reaction composition is incubated under conditions suitable for at least some of the adaptor species to hybridize with corresponding RNA molecules. It is to be understood that the process of (i) combining the adaptor species with the sample containing RNA, (ii) incubating to allow the adaptors to anneal with a corresponding RNA molecule, then (iii) adding the ligase to the reaction composition is within the intended scope of forming the ligation reaction composition and incubating, unless expressly stated otherwise.

The multiplicity of different adaptor species typically comprise sets of RNA/DNA oligonucleotides with single-stranded degenerate sequence at one end and in certain embodiments, a defined sequence at or near the other end that may serve as a binding site for amplification primers or reporter probes, sample identification (for example but not limited to pooling libraries generated from different starting materials and subsequently identifying the source of the amplified library), and/or sequencing of subsequently generated amplified products. In certain embodiments, hybridizing sample with Adaptor Mix A will yield amplified products suitable for SOLiD™ sequencing from the 5' ends of the sequence corresponding to the RNA molecule within the amplified product. Conversely, hybridization with Adaptor Mix B yields amplified products suitable for SOLiD™ sequencing from the 3' ends. A polypeptide comprising double-strand specific RNA ligase activity is then added to the mixture to ligate the hybridized adaptors to the small RNA molecules.

The ligation reaction composition is combined with a DNA polymerase comprising RNA-dependent DNA polymerase activity and the ligated product is reverse transcribed to generate cDNA. This reverse transcribed product is combined with RNase H to digest at least some of the small RNA or fragmented mRNA from the RNA/cDNA duplexes, generating amplification templates. Those in the art will appreciate that the concentration of unligated adaptors and adaptor by-products is also decreased during the ribonuclease digestion process. At this point, reactions contain cDNA copies of the RNA molecules in the sample. To meet the amplified product input requirements for certain sequencing techniques, and in some embodiments to append identifier sequences to the amplified products, the reverse transcribed products may be amplified using appropriate primer sets, wherein at least one forward primer, at least one reverse primer, or both may comprise one or more identifier sequences, and a number of PCR amplification cycles wherein detection is in a linear range when plotted vs. cycle number (~12-15 or ~12-18 cycles of PCR). Those in the art will appreciate that limiting the cycle number minimizes the synthesis of spurious PCR products and preserves the integrity of the RNA profile of the sample. In certain embodiments, at least one forward primer, at least one reverse primer, or at least one forward and at least one reverse primer comprise one or more identifier sequences. Certain embodiments comprise use of ten sets of PCR primers that have the same nucleotide sequence, except for a 6 bp "barcode" identifier sequence on the 3' (reverse) primer that is specific to that reverse primer species.

In certain embodiments, the amplification reaction products are subjected to size selection, for example but not limited to, gel electrophoresis, to concentrate the amplified products in a desired size range and remove PCR by-products. Appropriately size selected amplified products can be used in the SOLiD™ Sequencing System (Applied Biosystems) workflow at the emulsion PCR (ePCR) step where the amplified products are attached to beads, further amplified using ePCR and ultimately sequenced, which allows the presence, absence, and/or quantity of various RNA molecules in the sample to be determined.

Those in the art will appreciate that, in certain circumstances, an amplified product and/or a ligated product can serve as a surrogate for the corresponding RNA molecule and that by detecting the amplified product, the ligated product, or both, the RNA molecule is indirectly detected and that such detection is within the scope of the current teachings.

Kits: Kits for performing certain of the instant methods are also disclosed. Certain kit embodiments include first adaptors, second adaptors, a polypeptide comprising double-strand specific RNA ligase activity, reverse transcriptase, ribonuclease H (RNase H), DNA polymerase, primers, or combinations thereof. In some embodiments, kits further comprise an agent for removing 5' phosphates from RNA, for example but not limited to, tobacco acid pyrophosphatase.

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. In some embodiments, the kit components are optimized to operate in conjunction with one another.

In certain embodiments, kits comprise at least one first adaptor species, at least one second adaptor species, a polypeptide comprising double-strand specific RNA ligase activity, a DNA polymerase, including without limitation, a RNA-directed DNA polymerase, a DNA-directed DNA polymerase, or a DNA polymerase comprising both RNA-directed and DNA-directed DNA polymerase activities, ribonuclease H, or combinations thereof. In certain embodiments, the ligase comprises bacteriophage T4 RNA ligase 2 (Rnl2) or a ligase from the Rnl2 family. In some embodiments, the first adaptor, the second adaptor, or both the first adaptor and the second adaptor comprise a single-stranded portion comprising degenerate sequences.

In certain embodiments, a kit comprises a plurality of first adaptor species, wherein each first adaptor species comprises a different degenerate sequence, a plurality of second adaptor species, wherein each second adaptor species comprises a different degenerate sequence, a ligase of the Rnl2 family, a RNA-directed DNA polymerase, a plurality of different first primer species, a DNA-directed DNA polymerase and RNase H (EC 3.1.26.4). In some embodiments, the kit further comprises tobacco acid pyrophosphatase.

In certain embodiments, a kit comprises a plurality of first adaptor species, wherein at least some of the first adaptor species comprise a degenerate sequence, a plurality of second adaptor species, wherein at least some of the second adaptor species comprise a degenerate sequence, a polypeptide comprising double-strand specific RNA ligase activity, a DNA polymerase, at least one primer species, and a ribonuclease. In some embodiments, the DNA polymerase of the kit comprises an RNA-dependent DNA polymerase and a DNA-dependent DNA polymerase. In addition, the kit may comprise tobacco acid pyrophosphatase.

In certain embodiments, kits further comprise a forward amplification primer and a reverse amplification primer. In some embodiments, a forward primer, a reverse primer, or both a forward and a reverse primer comprise a universal priming sequence or the complement of a universal priming sequence. In some embodiments, kits comprise a forward primer, a reverse primer, or a forward primer and a reverse primer that further comprises a reporter group. In some such embodiments, the reporter group of a forward primer of a primer pair is different from the reporter group of the reverse primer of the primer pair. In some embodiments, kits further comprise at least one of: a reporter probe, a nucleic acid dye, a reporter group, or combinations thereof. In some embodiments, kits further comprise a control sequence, for example but not limited to an internal standard sequence such as a housekeeping gene or a polynucleotide ladder comprising molecular size or weight standards.

In certain kit embodiments a first adaptor, a second adaptor, a forward primer, a reverse primer, or combinations thereof, comprise an identification sequence or the complement of an identification sequence. In certain embodiments, the identification sequence comprises one of (i) 5'-AAGCCC, (ii) 5'-CACACC, (iii) 5'-CCCCTT, (iv) 5'-CATCGG, (v) 5-TCGTTG, (vi) 5'-GGGCAC, (vii) 5'-CCAGAC, (viii)

5'-CTCCGT, (ix) 5'-CCCTTC, (x) 5'-GCGGTC, or the complement of any one of these sequences (i)-(x). In some embodiments, a reverse primer comprises the sequence of one of SEQ ID NO:6 and SEQ ID NO:15 to SEQ ID NO:23. In some kit embodiments, mixtures of forward primers and reverse primers are provided. In some embodiments, kits provide a plurality of primer mixtures, for example but not limited to, at least two of: (i) a primer mixture comprising a first forward primer and a first reverse primer, wherein the first reverse primer comprises a first identification sequence; (ii) a primer mixture comprising the first forward primer and a second reverse primer, wherein the second reverse primer comprises a second identification sequence; (iii) a primer mixture comprising the first forward primer and a third reverse primer, wherein the third reverse primer comprises a third identification sequence; (iv) a primer mixture comprising the first forward primer and a fourth reverse primer, wherein the fourth reverse primer comprises a fourth identification sequence; (v) a primer mixture comprising the first forward primer and a fifth reverse primer, wherein the fifth reverse primer comprises a fifth identification sequence; (vi) a primer mixture comprising the first forward primer and a sixth reverse primer, wherein the sixth reverse primer comprises a sixth identification sequence; (vii) a primer mixture comprising first forward primer and a seventh reverse primer, wherein the seventh reverse primer comprises a seventh identification sequence; (viii) a primer mixture comprising first forward primer and an eighth reverse primer, wherein the eighth reverse primer comprises an eighth identification sequence; (ix) a primer mixture comprising the first forward primer and a ninth reverse primer, wherein the ninth reverse primer comprises a ninth identification sequence; and (x) a primer mixture comprising the first forward primer and a tenth reverse primer, wherein the tenth reverse primer comprises a tenth identification sequence.

Some kit embodiments comprise at least one adaptor mix, wherein each adaptor mix comprises a first adaptor and a second adaptor; at least one polypeptide comprising double-strand specific RNA ligase activity; a reverse transcriptase (RNA-directed DNA polymerase); a DNA polymerase (DNA-directed DNA polymerase); a ribonuclease; a mixture of deoxyribonucleotide triphosphates (dNTPs); and at least one amplification primer mix, wherein each amplification primer mix comprises a forward primer and reverse primer. In some embodiments, the RNA-directed DNA polymerase and the DNA-directed DNA polymerase comprise either an RNA-directed DNA polymerase that possesses DNA-directed DNA polymerase activity under certain reaction conditions or a DNA-directed DNA polymerase that possesses RNA-directed DNA polymerase activity under certain reaction conditions, for example but not limited to, Tth DNA polymerase and DNA polymerase I from *Carboxydothermus hydrogenoformans*. In some kit embodiments, the DNA-dependent DNA polymerase comprises Taq DNA polymerase, including enzymatically active mutants and variants thereof, for example but not limited to, AmpliTaq® DNA polymerase and AmpliTaq Gold® DNA polymerase (Applied Biosystems). In some embodiments, the ribonuclease comprises ribonuclease H (RNase H). Some kit embodiments comprise at least one control RNA molecule, for example but not limited to, at least one positive control RNA molecule, at least one negative control RNA molecule, or both.

Solid Supports: In certain embodiments, the disclosed methods and kits comprise a solid support. In some embodiments, a solid support is used in a separating and/or detecting step, for example but not limited to, for purifying and/or analyzing amplification products. Non-limiting examples of solid supports include, agarose, sepharose, polystyrene, polyacrylamide, glass, membranes, silica, semiconductor materials, silicon, organic polymers; optically identifiable microcylinders; biosensors comprising transducers; appropriately treated or coated reaction vessels and surfaces, for example but not limited to, micro centrifuge or reaction tubes, wells of a multiwell microplate, and glass, quartz or plastic slides and/or cover slips; and beads, for example but not limited to magnetic beads, paramagnetic beads, polymer beads, metallic beads, dye-impregnated or labeled beads, coated beads, glass beads, microspheres and nanospheres. Those in the art will appreciate that any number of solid supports may be employed in the disclosed methods and kits and that the shape and composition of the solid support is generally not limiting.

The current teachings, having been described above, may be better understood by reference to examples. The following examples are intended for illustration purposes only, and should not be construed as limiting the scope of the teachings herein in any way.

EXAMPLE 1

Generation of Amplified Products using Double Strand-Specific RNA Ligase Rnl2

Each of three RNA samples:
total RNA from human placenta (100 μg, Ambion P/N AM7950),
synthetic miRNA molecules (mirVana™ miRNA Reference Panel v. 9.1, 100 fmol, Ambion P/N 4388891, an equimolar pool of synthetic RNA oligonucleotides representing most of the human, mouse, and rat miRNA sequences in miRBase Sequence Database Version 9.1), and
flashPAGE™ Fractionation System-purified total RNA (human placenta) from 5 μg total RNA,
was mixed with 3 μL hybridization solution (300 mM NaCl, 20 mM Tris-HCl pH 8.0, 2 mM EDTA) and 2 μL Adaptor oligo mix containing oligonucleotides as follows:
3.1 μM (5'-upper, i.e., first oligonucleotide) 5'-CCUCUC-UAUGGGCAGUCGGUGAU-3', SEQ ID NO:1;
6.1 μM (5'-lower, i.e., second oligonucleotide) 5'-NNNNNNATCACCGACTGCCCATAGAGAGG-3', SEQ ID NO:2;
3.1 μM (3'-upper, i.e., third oligonucleotide) 5'-$PO_4$-CGC-CTTGGCCGTACAGCAG-3', SEQ ID NO:3; and
6.1 μM (3'-lower, i.e., fourth oligonucleotide) 5'-CTGCT-GTACGGCCAAGGCGNNNNNN-3'; SEQ ID NO:4)
where "N" represents degenerate bases (A, C, G or T) mixed in a 25:25:25:25 ratio.

The lyophilized oligonucleotides were resuspended to a stock concentration of 100 μM in nuclease-free water (Ambion P/N AM9937) and diluted accordingly. The RNA mixture was heated at 65° C. for 10 minutes followed by 5 minutes at 16° C. to hybridize the adaptors to the small RNA in the sample.

The hybridized RNA/Adaptors were then mixed with 10 μL Ligation Buffer (100 mM Tris-HCl pH 7.5, 20 mM $MgCl_2$, 20 mM dithiothreitol, 2 mM ATP, and 40% (w/v) PEG-8000) and ligated with 20 units of T4 RNA ligase 2 (NEB, Ipswich, Mass.) in a total of 20 μL for 16 hours at 16° C. In addition, a minus ligase control was prepared for the total RNA sample using nuclease-free water in place of the ligase enzyme.

The ligated products were reverse transcribed by incubating for 30 minutes at 42° C. with 200 units of ArrayScript™ reverse transcriptase (Ambion P/N AM2048), 4 μL 10×RT buffer (provided with the ArrayScript™ enzyme) and 2 μL 2.5 mM dNTP mix (Ambion P/N AM8228G) in a total volume of 40 µL. A minus RT control was included for the total RNA sample using nuclease-free water in place of the reverse transcriptase.

Excess RNA byproducts were removed by incubating a 10 µL aliquot of the sample at 37° C. for 30 minutes with 10 units of RNase H (Ambion P/N AM2292) and the RNase-treated cDNA was amplified by PCR. The 50 µL PCR reactions contained the following:

- 38.5 µL nuclease-free water (Ambion P/N AM9937),
- 5 µL GeneAmp® 10×PCR Buffer I (Applied Biosystems P/N N8080246),
- 4 µL 2.5 mM dNTP mix (Ambion P/N AM8228G),
- 0.5 µL 50 µM forward PCR primer: (5'-CCACTACGC-CTCCGCTTTCCTCTCTATGGGCAGTCGGTGAT-3' (SEQ ID NO: 5),
- 0.5 µL 50 µM reverse PCR primer: (5'-CTGCCCCGGGT-TCCTCATTCTCTCCAGACCTGCTGTACG-GCCAAGGCG-3')(SEQ ID NO:6),
- 1 µL AmpliTaq® DNA Polymerase (Applied Biosystems P/N N8080246), and
- 0.5 µL cDNA sample.

The PCR conditions were as follows: initial denaturation at 95° C. for 5 minutes, followed by 15 cycles of 95° C. for 30 seconds (denaturation), 62° C. for 30 seconds (annealing), and 72° C. for 30 seconds (extension). A final extension at 72° C. for 7 minutes followed.

Ten µL of each sample was mixed 1:1 with Gel Loading Buffer II (Ambion P/N AM8547) and the entire volume was loaded onto a 1.0 mm 6% polyacrylamide gel and electrophoresed for approximately 45 minutes at 180 volts constant in 1× tris-borate EDTA running buffer (Ambion P/N AM9863). The gel was removed from the cassette and stained in 1×SYBR® Gold nucleic acid gel stain (Invitrogen P/N S11494) in 1×TBE for 5 minutes. The gel was imaged using the Alpha Innotech FluorChem SP imager and the image processed with AlphaEase® FC software version 6.0.0.

As seen in FIG. 5, the amplified ligation products (amplified product) are shown by bracket A; arrow B denotes undesired by-products of the reaction that were amplified in the amplification reaction; bracket C indicates the residual unligated adaptors and primers in the amplification reaction composition.

Note that the forward PCR primer sequence contains SEQ ID NO:1, the sequence of the first oligonucleotide (with T substituted for U), beginning at nucleotide 19 of the forward primer. Note also that the reverse primer sequence contains SEQ ID NO:4, the sequence of the fourth oligonucleotide (with T substituted for U), beginning at nucleotide 30 of the reverse primer. Therefore, with this construction, a detected small RNA will have a length equal to a gel fragment size as seen in FIG. 5, for example, less the total of the lengths of the primers.

EXAMPLE 2

Generation of Amplified Product using Various Double-Strand Specific Ligases

Total RNA from human placenta (500 ng, Ambion P/N AM7950) was mixed with 3 µL Hybridization solution and 2 µL Adaptor oligo mix and hybridized as in Example 1. The hybridized RNA/Adaptors were then mixed with 10 µL Ligation Buffer (100 mM Tris-HCl pH 7.5, 20 mM MgCl₂, 20 mM dithiothreitol, 2 mM ATP, and 40% (w/v) PEG-8000) and ligated with 10 units of either bacteriophage T4 RNA ligase 2, bacteriophage T4 RNA ligase 1 (Ambion P/N AM2140), bacteriophage T4 DNA ligase (Ambion P/N AM2134), or a 1:1 mixture of T4 RNA ligase I and T4 DNA ligase in a total of 20 µL for 16 hours at 16° C. In addition, a minus ligase control was prepared using nuclease-free water in place of the ligase enzyme.

The ligated products were reverse transcribed, treated with RNase H and amplified as in Example 1. Ten µL of each sample was mixed 1:1 with Gel Loading Buffer II (Ambion P/N AM8547) and the entire volume was loaded onto a 1.0 mm 6% polyacrylamide gel (Invitrogen P/N EC6265BOX) and electrophoresed for approximately 45 minutes at 180 volts constant in 1× tris-borate EDTA running buffer (Ambion P/N AM9863). The gel was removed from the cassette and stained in 1×SYBR® Gold nucleic acid gel stain (Invitrogen P/N S11494) in 1×TBE for 5 minutes. The gel was imaged using the Alpha Innotech FluorChem SP imager and the image processed with AlphaEase® FC software ver. 6.0.0. Bands were compared to a 10 bp DNA ladder (100 ng; Invitrogen P/N 10821-015).

As seen in FIG. 6, the amplified ligation products (amplified product) are shown by bracket A; arrow B denotes undesired by-products of the reaction that were amplified; and bracket C indicates the residual unligated adaptors and primers in the amplification reaction composition. Surprisingly, when the amplified products generated using ligase Rnl2 (lane 2), ligase Rnl1 (lane 4), ligase Dnl (lane 6), or a combination of both Rnl1 and Dnl (lane 8) are compared, a different amplified product profile is observed. Amplified product in the 110 base pair (bp) to 130 bp size range (arrow A), which in this illustrative embodiment is in the size range expected for amplified miRNA, is observed when Rnl2 ligase is used, but not when Rnl1 or Dnl are used, either alone or in combination. Additionally, a prominent band of amplified product of approximately 100 bp (migrating slightly above B in FIG. 6) appears in all lanes corresponding to Rnl1, Dnl or both (with and without reverse transcriptase), but this band is not observed when Rnl2 is used. This difference in amplified products generated with Rnl2 in comparison to the amplified products generated using two different ligases either alone or in combination in parallel reactions is surprising and unexpected.

EXAMPLE 3

Generation of Barcoded Amplified Products for Sequencing

Small RNA is obtained from HeLa cells using the mirVana™ miRNA Isolation Kit (AM1560, Ambion) according to the manufacturer's Instruction Manual following the procedures for total RNA isolation.

Ligation reaction compositions were prepared as follows. Hybridization mixtures were prepared in 0.2 mL RNase-free thin-walled PCR tubes comprising for each reaction: 2 µL adaptor mix (first adaptor and second adaptor), 3 µL 2× hybridization solution (300 mM NaCl, 20 mM Tris, 2 mM EDTA, final pH 8.0), 1-3 µL RNA molecule solution from mirVana™ miRNA Isolation Kit (containing 1000 nanograms (ng) RNA) or 1000 ng positive control (FirstChoice® Total RNA: Human Placenta; AM7950, Ambion), and 0-2 µL nuclease free (NF) water (NF water volume adjusted to yield a total volume of 8 µL/reaction). The tube(s) comprising the hybridization mixture was mixed gently and placed in a thermal cycler programmed for 65° C. for ten minutes, then 16° C. for five minutes. The tube(s) were kept at 16° C. and ligation reaction compositions were prepared by combining in order 8 µL of the thermal cycled hybridization mixture, 10

µL 2× ligation buffer (100 mM Tris, 20 mM MgCl$_2$, 20 mM DTT, 2 mM ATP, 40% PEG 8000, pH 7.0) and 2 µL ligase mix (10 U/µL bacteriophage T4 RNA ligase 2 (Rnl2), 2 U/µL RNase Inhibitor Protein) for a final volume of 20 µL for each reaction. The tube(s) were mixed by pipetting up and down and then incubated at 16° C. for 16 hours in the thermal cycler. Typically, 2 hour incubation is sufficient for a first adaptor and a second adaptor to anneal with an RNA molecule and for ligation to occur, generating ligated product (see, e.g., 34 in FIG. 3).

The tube(s) comprising ligated product was placed on ice and a reverse transcription master mix (RTMM) prepared as follows. For each tube of ligated product, 13 µL NF water, 4 µL 10× RT buffer (500 mM Tris-HCl pH 8.3, 750 mM KCl, 30 mM MgCl$_2$, 50 mM DTT, final pH 8.25), 2 µL 2.5 mM dNTP mix, and 1 µL RT enzyme mix (200 U/µL ArrayScript™ reverse transcriptase (RNA-directed DNA polymerase), were combined to form the RTMM. Twenty µL of RTMM was added to each ligated product tube with mixing by pipetting up and down 3-5 times followed by incubation at 42° C. for thirty minutes to generate reverse transcribed product (see, e.g., 36 in FIG. 3). After this incubation, a ten µL aliquot of the solution comprising the reverse transcribed product was transferred to a fresh 0.2 mL tube to which 1 µL of RNase H enzyme (10 U/µL E. coli RNase H) was added. The tube(s) was mixed gently and incubated at 37° C. for thirty minutes, during which time the reverse transcribed product was digested and amplification template (see, e.g., 38 in FIG. 3) formed.

A PCR master mix was prepared comprising 38.5 µL NF water, 5 µL GeneAmp® PCR buffer I, 1 µL PCR primer mix (25 µM forward primer, 25 µM reverse barcoded primer), 4 µL 2.5 mM dNTP mix, and 1 µL AmpliTaq® DNA polymerase (5 U/µL; DNA-directed DNA polymerase)—a total of 49.5 µL per amplification reaction to be performed. This exemplary PCR primer mix includes one forward primer and a barcoded reverse primer.

To determine the appropriate number of PCR cycles to use with a given solution comprising amplified product, a small scale (i.e., 50 µL) PCR reaction is recommended. Small scale amplification reaction compositions were prepared by combining 49.5 µL of this PCR master mix with 0.5 µL of the solution comprising amplification template in a RNase-free 0.2 mL thin-walled PCR tube. The amplification reaction compositions were placed in a thermal cycler with a heated lid, heated at 95° C. for five minutes, then cycled for 12-15 cycles using a profile of 95° C. for 30 seconds-62° C. for 30 seconds-72° C. for 30 seconds; then a final extension step is performed at 72° C. for 7 minutes. The optimum number of amplification cycles depends on the amount of amplification product in the initial amplification reaction composition. A 5-10 µL aliquot of the amplification reaction composition comprising amplified product was analyzed by electrophoresis using a 6% native tris-borate EDTA (TBE) acrylamide gel to determine the optimum number of amplification cycles. Following such determination, a large scale amplification is performed.

To generate sufficient quantities of amplified product for sequencing and/or other downstream processes, a larger scale amplification reaction was performed by PCR. Master mix was prepared by combining, for each reaction to be performed, 77 µL NF water (Ambion AM9922), 10× Gene-Amp® PCR Buffer I (or 10×PCR Buffer I, Applied Biosystems P/N N8080160), 2 µL barcoded PCR primers (mix of forward and a barcoded reverse primer of choice), 8 µL dNTP mix, and 2 µL AmpliTaq® DNA-directed DNA Polymerase (Applied Biosystems P/N N8080160). A 99 µL aliquot of this master mix and 1 µL of the solution comprising amplification templates were combined in three separate wells of an RNase-free PCR plate (i.e., in triplicate) to form an amplification reaction composition. The PCR plate was heated to 95° C. for 5 minutes to denature the nucleic acid, cycled according to the previous temperature profile (95° C. for 30 seconds-62° C. for 30 seconds-72° C. for 30 seconds) for the previously determined number of cycles and finally the PCR reaction vessel was maintained at 72° C. for 7 minutes to generate amplified products in the amplification reaction composition. The amplified products were pooled analyzed by electrophoresing 5-10 µL of the pooled amplification reaction compositions on a 6% native TBE acrylamide gel as before.

Two hundred and fifty (250) µL of the pooled amplified product was combined with 250 µL phenol/chloroform/isoamyl alcohol (25:24:1, pH 7.9) in an RNase-free 1.5 mL polypropylene microfuge tube and mixed by vortexing. The tube was centrifuged at 12,000 rpm for 5 minutes at room temperature using a benchtop centrifuge. The aqueous phase was measured and transferred to a fresh RNase-free 1.5 ml polypropylene microfuge tube and an equal volume of 7.5 M ammonium acetate added to the tube along with 1/100 volume of glycogen (or GlycoBlue™ Co-precipitant (Ambion) and 0.7 volumes isopropanol. The contents of the tube are mixed thoroughly, incubated at room temperature for 5 minutes, and then centrifuged at 12,000 rpm for 20 minutes at room temperature. The resulting supernatant was removed and discarded and the pellet washed three times with 1 mL of 70% (v/v) ethanol. The pellet was air dried, then resuspended in 18 µL nuclease-free water to which 2 µL of 10× native gel loading dye is added. Ten µL of this suspension was added to each of two wells of a native TBE PAGE gel which contains a 10 basepair (bp) molecular weight ladder (Invitrogen 10821-015) as a marker in one of the other wells. The amplified products were electrophoresed in the gel at ~140 V until the dye front is about to elute off the bottom edge of the gel (~30 minutes for a 1.0 mm, 8 cm×8 cm gel). The nucleic acid bands in the gel were stained using SYBR® Gold (Invitrogen, Carlsbad, Calif.) following the manufacturer's instructions and illuminated using an ultraviolet light source. Using a clean razor blade, the gel was sliced in the lanes containing amplified product to obtain the nucleic acid in the size range of approximately 100 to 150 bp. A distinct band at 100 bp likely represents undesired byproducts and was not included with the slice excised from the gel. Likewise, nucleic acid larger than about 200 bp was also avoided when certain sequencing methods were employed, for example but not limited to, emulsion PCR sequencing using the SOLiD™ System (Applied Biosystems).

A hole was made in the bottom of an RNase-free 0.5 mL polypropylene microfuge tube using a 21 gauge needle and the excised gel piece is transferred to the tube. This 0.5 mL tube was then placed inside an RNase-free 1.5 mL polypropylene microfuge tube and centrifuged for 3 min at 12,000 rpm to shred the gel. The 0.5 mL tube is removed and discarded and the outer 1.5 mL tube containing the gel fragments is placed on ice. Two hundred (200) µL PAGE elution buffer (1.5 M ammonium acetate in 1×TE buffer pH 7.0) was added to tube, which was then incubated at room temperature for 20 minutes. After this first incubation, the supernatant was removed and transferred to a clean RNase-free 1.5 mL polypropylene microfuge tube and an additional 250 µL of PAGE elution buffer was added to the first tube (containing the gel fragments) and incubated for an additional 40 minutes at 37° C. Following the second incubation, the second supernatant was collected and added to the first. Residual gel pieces were removed form the pooled supernatants using a spin column (Ambion Cat#10065) and centrifugation, according to the manufacturer's instructions.

The resulting liquid was combined with an equal volume of phenol/chloroform/isoamyl alcohol (25:24:1, pH 7.9) in an RNase-free 1.5 mL polypropylene microfuge tube and mixed by vortexing. The tube was centrifuged at 12,000 rpm for 5 minutes at room temperature using a benchtop centrifuge. The aqueous phase was measured and transferred to a fresh RNase-free 1.5 ml polypropylene microfuge tube and an equal volume of 7.5 M ammonium acetate was added to the tube along with 1/100 volume of glycogen (AM9510, Ambion; or GlycoBlue™ Co-precipitant AM9515, Ambion) and 0.7 volumes isopropanol. The contents of the tube were mixed thoroughly, incubated at room temperature for 5 minutes, and then centrifuged at 12,000 rpm for 20 minutes at room temperature. The resulting supernatant was removed and discarded and the pellet washed three times with 1 mL of 70% (v/v) ethanol. The pellet was air dried, then resuspended in 20 µL NF water. The DNA comprising the amplified product was quantitated by determining the $A_{260}$ with a spectrophotometer or by analyzing on a 6% native PAGE gel, as described above.

To determine the sequence of the amplified product, emulsion PCR (ePCR) was performed on an Applied Biosystems SOLiD™ System according to the User Guide (Applied Biosystems, P/N4391578; the "User Guide"). To evaluate what concentration of amplified product that gives the best sequencing results in a full scale ePCR on the SOLiD™ System, four separate ePCR reactions were performed at amplified product concentrations of 0.2 pg/µL, 0.4 pg/µL, 0.6 pg/µL, and 0.8 pg/µL, followed by a titration/QC run according to the manufacturer's instructions (see particularly, the User Guide, Chapters 3 and 4). When the optimal amplified product concentration was determined, a "full scale" ePCR reaction was performed (see Section 3.1, Chapter 3 of the User Guide). By determining the sequence of at least part of the amplified product, one can directly or bioinformatically identify the RNA molecule from which that amplified product was derived, thereby detecting that RNA molecule. Those in the art will appreciate that such sequence information may be used to identify novel RNA molecules, including without limitation, small RNA discovery; may be used to quantitate the amount of one detected RNA molecule species in the starting sample relative to the amount another detected RNA species and such information may be useful for, among other things, expression profiling of mRNA, miRNA or other RNA molecules of interest.

EXAMPLE 4

Evaluation of Adaptor Overhang Length

First and second adaptors with various overhang lengths were synthesized and evaluated in an effort to maximize ligation efficiency while minimizing adaptor complexity.

Exemplary first adaptors comprised first oligonucleotides, depicted as "T3" in FIG. 7B wherein the first oligonucleotides comprised a DNA sequence from bacteriophage T3 and two ribonucleotides at the 3' end, and second oligonucleotides, depicted as "27 N" in FIG. 7B wherein the second oligonucleotides comprised a complementary deoxyribonucleotide sequence from bacteriophage T3 and an overhang of 4, 6 or 8 degenerate deoxyribonucleotides "N" at the 5' end. The upper strand (first oligonucleotide) of an illustrative first adaptor comprised a 27 nucleotide sequence from the bacteriophage T3 promoter 5'-CUCGAGAAUUAACCCUCAC-UAAAGGGA-3' (SEQ ID N0:7), shown as "T3" in FIG. 7B. The lower strand (second oligonucleotide) comprised the complementary sequence of the upper strand with either 4, 6, or 8 degenerate nucleotides (depicted as "N" for illustration purposes in FIG. 7B) on the 5' end of the lower strand 5'-$(N)_{468}$TCCCTTTAGTGA GGGTTAATTCTCGAG-3' (SEQ ID N0:8 (where N=8); SEQ ID N0:8 lacking either 2 or 4 5'-N's (i.e., where N is 6 or 4)), depicted as "27 N" for illustration purposes in FIG. 7B.

Exemplary second adaptors comprised third oligonucleotides, depicted as "T7" in FIG. 7B wherein the third oligonucleotides comprised a DNA sequence from bacteriophage T7, and fourth oligonucleotides, depicted as "N 28" in FIG. 7B wherein the fourth oligonucleotides comprised a complementary deoxyribonucleotide sequence from bacteriophage T7 and an overhang of 4, 6 or 8 degenerate deoxyribonucleotides "N" at its 3' end. The upper strand (third oligonucleotide of an illustrative second adaptor comprised a 28 nucleotide sequence from the bacteriophage T7 promoter 5'-$PO_4$-TCCCTATAGTGAGTCGTATTACGAATTC-3'(SEQ ID N0:9) shown as "T7" in FIG. 7B which comprises a 5' phosphate group (shown as $PO_4$). The lower strand (fourth oligonucleotide) comprised the complementary sequence of the upper strand with either 4, 6, or 8 degenerate nucleotides (depicted as "N" for illustration purposes in FIG. 7B) on the 3' end of the lower strand 5'-GAATTCGTAATACGACT-CACTATAGGGA$(N)_{4,6,8}$-3 (SEQ ID NO:10 (where N=8); SEQ ID N0:10 lacking either 2 or 4 3'-N's (i.e., where N is 6 or 4)), depicted as "N 28" for illustration purposes in FIG. 7B.

Fifty picomoles (pmol) of either the "T3" first adaptors (see FIG. 7B), the "T7" second adaptors (see FIG. 7B), or both the T3 first adaptors and the T7 second adaptors (both with the same number of degenerate nucleotides) in 2 µL water was incubated with 3 µL 2× Hybridization Buffer (300 mM NaCl, 20 mM Tris pH8, 2 mM EDTA) at 95° C. for 3 minutes, then cooled to 22° C. When the temperature reached 22° C., 1 µL of a 0.13 µM 5' $^{32}$P-labeled synthetic microRNA pool (mirVana™ miRNA Reference Panel 9.0, a pool of approximately 500 synthetic miRNA sequences from the Sanger miRBase 9.0 database (microrna.sanger.ac.uk/sequences/) in equimolar concentration) was added to each reaction tube, the tubes were incubated at 65° C. for 10 minutes, then cooled down to 22° C.

Reaction mixtures were then incubated at 16° C. for 30 minutes, then 14 µL ligation enzyme mix (0.5 µL RNA ligase 2 (10 µM), 2 µL 10× Rnl2 buffer (100 mM Tris pH7, 20 mM $MgCl_2$, 20 mM Dithiothreitol, 20 mM ATP), 1 µL RNase Inhibitor (Ambion AM2682, 40 U/µL), 10 µL 40% PEG 8000 (Sigma-Aldrich 202452) and 0.5 µL RNase-free water) was added to each tube. The reaction mixtures were incubated for another 16 hours at 16° C. Twenty µL of Gel Loading Buffer II (Ambion AM8546G) was then added to each reaction and heated at 95° C. for 5 minutes. The $^{32}$P-labeled products were resolved by 10% denaturing PAGE and visualized by autoradiography. Control reactions lacking (i) both RNA ligase 2 and adaptors or (ii) adaptors only, are shown in the first two lanes of FIG. 7A. Substantial amounts of the double ligation product (ligated product) were observed in the lanes of the gel corresponding to ligation reaction mixtures comprising both the first adaptors and the second adaptors (i.e., T3-4+T7-4; T3-6+T7-6; and T3-8+T7-8), as shown in FIG. 7A. Therefore, adaptor overhang lengths of 4, 6, and 8 nucleotides provide for detection of small RNA.

EXAMPLE 5

Adaptor Structure

Different structures of 5' (first) and 3' (second) adaptors with 6-nucleotide degenerate overhangs were tested which included dsDNA (with the exception of two 3' terminal RNA bases on the upper strand (first oligonucleotide) of the 5' (first) adaptor (e.g., T3r2:27 6N and T7:6N 28 in FIG. 8B (the numbers 27 and 28 refer to the length of the first and third oligonucleotides, respectively, as in Example 4) and dsRNA•DNA hybrid (upper (first and third oligonucleotides are RNA)-lower (second and fourth oligonucleotides are DNA) for both adaptors (e.g., rT3:27 6N and rT7:6N 28 in FIG. 8B).

In this illustrative embodiment of FIG. 8B, top first adaptor (rT3:27 6N) comprises an upper strand (first oligonucleotide) comprising the T3 sequence (SEQ ID NO:7) wherein all of the nucleosides comprise ribonucleosides, shown as "rT3," annealed to the lower strand (second oligonucleotide) comprising the complementary sequence and 6 degenerate nucleotides on the 5' end of the lower strand (SEQ ID NO:8 where N is 6), depicted as "27 6N" for illustration purposes; and the other illustrative first adaptor (T3r2:27 6N) comprises an upper strand comprising the T3 sequence wherein all of the nucleosides comprise deoxyribonucleosides except for the two 3'-most nucleosides which comprise ribose (SEQ ID NO:7 having 2 3'-terminal ribonucleotides), shown as "T3r2" annealed to the same lower strand as the top first adaptor (SEQ ID NO:8 where N is 6) depicted as 27 6N.

Again referring to FIG. 8B, a top illustrative second adaptor (rT7:6N 28) comprises an upper strand (third oligonucleotide) comprising the T7 sequence (SEQ ID NO:9) wherein all of the nucleosides comprise ribonucleosides and which sequence comprises a 5' phosphate group, depicted as "rT7" for illustration purposes, annealed to the lower strand which comprises the complementary sequence with 6 degenerate nucleotides on the 5' end of the lower strand (SEQ ID NO:10 where N is 6), depicted as "6N 28" for illustration purposes. The other illustrative second adaptor (T7:6N 28) comprises an upper strand comprising the T7 sequence (SEQ ID NO:9) wherein all of the nucleosides comprise deoxyribonucleosides and which sequence comprises a 5' phosphate group, depicted as "T7" for illustration purposes, annealed to the same lower strand as the top second adaptor (SEQ ID NO:10 where N is 6), depicted as 6N 28.

Fifty pmol of either the first adaptors, the second adaptors, or both the first adaptors and the second adaptors, in 2 µL water was incubated with 3 µL 2× Hybridization Buffer (300 mM NaCl, 20 mM Tris pH8, 2 mM EDTA) at 95° C. for 3 minutes and cooled down to 22° C. One (1) µL of a 0.13 µM 5' $^{32}$P-labeled miRNA pool (mirVana™ miRNA Reference Panel as cited above) was added to each reaction, then incubated at 65° C. for 10 minutes, and cooled down to 22° C.

Reaction mixtures were incubated at 16° C. for 30 minutes, then 14 µL of ligation enzyme mix (0.5 µL RNA ligase 2 (10 µM), 2 µL 10×Rnl2 buffer (100 mM Tris pH7, 20 mM MgCl$_2$, 20 mM Dithiothreitol, 20 mM ATP), 1 µL RNase Inhibitor (Ambion AM2682, 40 U/µL), 10 µL 40% PEG 8000 (Sigma-Aldrich 202452) and 0.5 µL RNase-free water) was added to each tube. The reaction mixtures were incubated at 16° C. for another 16 hours. Gel Loading Buffer II (20 µL, Ambion AM8546G) was then added to each reaction and heated at 95° C. for 5 minutes. The $^{32}$P-labeled products were resolved by 10% denaturing PAGE and visualized by autoradiography. As shown in FIG. 8A, substantial amounts of ligated products (indicated by arrow) are observed only when the ligation reaction mixtures comprised both first adaptors and second adaptors (T3r2-6+T7-6; and rT3-6+rT7-6), but more undesired reaction byproduct (indicated by *) is seen with the combined rT3-6+rT7-6 adaptors than with combined T3r2-6+T7-6 adaptors.

EXAMPLE 6

Adaptor Combinations

Three different combinations of first adaptors and second adaptors were tested for double ligation efficiency. These combinations included first adaptors and second adaptors with both DNA upper strands (i.e., first and third oligonucleotides are DNA with the exception that the first oligonucleotide has two 3' ribonucleotides), both RNA upper strands (i.e., first and third oligonucleotides), or RNA upper strand on 5' (first) adaptor (i.e., first oligonucleotide) and DNA upper strand on 3' (second) adaptor (i.e., third oligonucleotide) (see FIG. 9C for a schematic of the latter adaptor structure embodiment). One (1) µL of each adaptor (50 µM each) was combined and incubated with 3 µL 2× Hybridization Buffer (300 mM NaCl, 20 mM Tris pH8, 2 mM EDTA) at 95° C. for 3 minutes and cooled down to 22° C. One (1) µL of a 0.13 µM 5' $^{32}$P-labeled synthetic miRNA pool (cited above) was added to each 5 µL reaction, the reactions were then incubated at 65° C. for 10 minutes and then cooled down to 22° C.

Reaction mixtures were then incubated at 16° C. for 30 minutes before 14 µL of the ligation enzyme mix was added to each tube. Ligation mix was prepared by combining 0.5 µL RNA ligase 2 (10 µM), 2 µL 10×Rnl2 buffer (100 mM Tris pH7, 20 mM MgCl$_2$, 20 mM Dithiothreitol, 20 mM ATP), 1 µL RNase Inhibitor (Ambion AM2682, 40 U/µL), 10 µL 40% PEG 8000 (Sigma-Aldrich 202452) and 0.5 µL RNase-free water. The reaction mixtures were incubated at 16° C. for another 16 hours. Twenty (20) µL of Gel Loading Buffer II (Ambion AM8546G) was then added to each reaction and heated at 95° C. for 5 minutes. The $^{32}$P-labeled products were resolved by 10% denaturing PAGE and visualized by autoradiography. FIG. 9A and FIG. 9B depict the resulting electropherograms of ligated products. Adaptors with either DNA or RNA upper strands are doubly ligated to generate "ligated product" as depicted in FIG. 9A.

Different ratios of adaptors (upper vs. lower strand, i.e., first vs. second oligonucleotide and third vs. fourth oligonucleotide) with and without ribonuclease H (RNase H) digestion were evaluated to maximize double ligation products while minimizing undesired by-products generated by direct ligation between 5' (first) and 3' (second) adaptors ("Ligated adaptors" in FIG. 10A). Adaptors with different upper/lower strand ratios as indicated in the table of FIG. 10A were mixed with either 0.2 or 2 pmol mirVana™ miRNA Reference Panel (cited above) and 3 µL 2× Hybridization Buffer (300 mM NaCl, 20 mM Tris pH8, 2 mM EDTA) in a 6 µL reaction mixture followed by incubating at 65° C. for 15 minutes and 16° C. for 45 minutes. Ligation mix was prepared by combining 1 µL RNA ligase 2 (10 µM), 1 µL RNase Inhibitor (Ambion AM2682, 40 U/µL), 2 µL 10×Rnl2 buffer (100 mM Tris pH7, 20 mM MgCl$_2$, 20 mM Dithiothreitol, 20 mM ATP) and 10 µL 40% PEG 8000 (Sigma-Aldrich 202452). Ligation mix (14 µL) was added to each tube and incubated at 16° C. for 16 hours.

After 16 hours' incubation, 4 µL 10×RT Buffer which contains 500 mM Tris-HCl (pH8.3), 750 mM KCl, 30 mM MgCl$_2$ and 100 mM DTT was combined with 2 µL 2.5 mM dNTP, 1 µL ArrayScript™ reverse transcriptase (200 U/µL, Ambion AM2048), 1 µL SUPERase•In™ RNase inhibitor (20 U/µL, Ambion AM2694), and 12 µL RNase-free water and then added to 20 µL of ligation reaction for a total of 40 µL of RT mixture. The reverse transcription (RT) reaction mixture was incubated at 42° C. for 30 minutes.

For the samples of lanes 1 to 6 shown on the gel in FIG. 10A, PCR was performed as follows. One (1) µL sample from the RT mixture was combined with 10 µL 10× Complete Buffer (Ambion AM2050), 1 µL dNTP (25 mM), 0.5 µL 5' primer and 0.5 µL 3' primer (50 µM each), 1 µL of SuperTaq DNA polymerase (5 U/µL, Ambion AM2050) and 86 µL of RNase-free water. PCR was performed using 20 cycles of 30 seconds at 95° C., 30 seconds at 50° C. and 30 seconds at 72° C. Five (5) µL of PCR products were loaded on a 10% native PAGE gel and visualized by SYBR® Gold (Invitrogen 11494) staining.

For the samples of lanes 7-12 shown on the gel in FIG. 10A, an RNase H digestion reaction was performed as follows followed by PCR. Five µL of the RT reaction was transferred to a clean tube, mixed with 0.5 µL Ribonuclease H (RNase H, 10 U/µL, Ambion AM2292) and incubated at 37° C. for 30 minutes. One (1) µL of RNase H treated sample was used for PCR reaction at the same condition as described previously. All of these amplified products (both with and without RNase H digestion) were loaded on a 10% native PAGE gel, electrophoresed, and visualized by SYBR® Gold (Invitrogen 11494) staining, as shown in FIG. 10A.

Adaptors with different upper/lower strand ratios as indicated in the table shown in FIG. 10B were mixed with 2 pmol synthetic mirVana™ miRNA Reference Panel (cited above) and 3 µL 2× Hybridization Buffer (300 mM NaCl, 20 mM Tris pH8, 2 mM EDTA) in a 6 µL reaction mixture followed by incubating at 65° C. for 15 minutes and 16° C. for 1 hour. The ligation, RT and RNase H treatment were performed as described previously. One (1) µL of RNase H treated sample was used for PCR amplification with SuperTaq™ polymerase (Ambion AM2050) in 20 cycles as described before. Five µL of each of the PCR products were loaded on a 10% native PAGE gel, electrophoresed, and visualized by SYBR® Gold (Invitrogen 11494) staining, as shown in FIG. 10B. Adaptors with picomolar ratios of upper to lower strand of 1/50, 5/50 10/50, 25/50 and 5/100 were all competent to generate the desired products migrating at >50 bp. In contrast, use of an adaptor ratio of 5/500 did not efficiently generate the desired products.

EXAMPLE 7

Comparison of the Present Method with TaqMan® miRNA Assays

Samples that Vary in RNA Content

The present example provides a quantitative validation of the present methods as compared to the RT-PCR TaqMan® miRNA assays. FIG. 12 depicts a scatter plot depicting a relative fold change (FC) comparison of miRNA quantitation results obtained from human placental RNA and from human lung RNA using 5' nuclease assays with sequencing results obtained according to certain embodiments of the current teachings. The x-axis shows the $\log_2$ fold change of 5' nuclease assay results in $-\Delta\Delta CT$ ((generated using TaqMan® Human MicroRNA Array v 1.0 (P/N 4384792; Applied Biosystems) and Multiplex RT for TaqMan® MicroRNA Assays (P/Ns 4383403, 4383402, 4383401, 4383399, 4384791, 4382898, 4383405, 4383400, and 4383404; Applied Biosystems) performed essentially according to the manufacturer's protocol) and the y-axis shows the $\log_2$ fold change of sequencing data (generated using the SOLiD™ Sequencing System (Applied Biosystems) essentially according to the manufacturer's protocol) according to an embodiment of the current teachings. TaqMan® MicroRNA Assays (Applied Biosystems) that generated $C_T$ values above 35 were presumed to be negative and not included in the analysis. For SOLiD™ sequencing data, data from at least 3 sequenced tags were required for the corresponding sequence to be considered as 'observed.' Using this approach an R value of 0.88 was obtained.

The present example also provides for total RNA input amounts since some sample types contain minimal small RNAs. One embodiment of a current method was performed using total RNA from either human placenta (FIG. 13A) or mouse liver (FIG. 13B) at the amounts indicated in the figures. In general, adaptor mix A (2 µl) (SOLiD™ adaptor mix A) containing 25 pmol RNA upper strand (first oligonucleotide) and 50 pmol DNA bottom strand (second oligonucleotide) with 6 degenerate DNA nucleotides forming an overhang at the 5' end as 5' (first) adaptor, and 25 pmol 5'-phosphorylated DNA upper strand (third oligonucleotide) and 50 pmol DNA bottom strand (fourth oligonucleotide) with 6 degenerate DNA nucleotides forming an overhang at the 3' end as 3' (second) adaptor were incubated with 3 µl 2× Hybridization Buffer (300 mM NaCl, 20 mM Tris pH8, 2 mM EDTA) and 1 µl total RNA with indicated amounts at 65° C. for 10 minutes and 16° C. for 5 minutes.

A ligation mix was prepared by combining 1 µL RNA ligase 2 (10 µM), 1 µl RNase Inhibitor (Ambion AM2682, 40 U/µL), 2 µL 10×Rnl2 buffer (100 mM Tris pH7, 20 mM MgCl₂, 20 mM Dithiothreitol, 20 mM ATP), and 10 µL 40% PEG 8000 (Sigma-Aldrich 202452). The ligation reaction mixtures were incubated at 16° C. fir 16 hours.

After 16 hours' incubation, 4 µL 10×RT Buffer which contains 500 mM Tris-HCl (pH8.3), 750 mM KCl, 30 mM MgCl₂ and 100 mM DTT was combined with 2 µL 2.5 mM dNTP, 1 µL ArrayScript™ reverse transcriptase (200 U/µL, Ambion AM2048), and 13 µL RNase-free water and then added to 20 µL ligation reaction composition. The reverse transcription (RT) reaction mixture was incubated at 42° C. for 30 minutes.

Then 5 µL of RT reaction was transferred to a clean tube, mixed with 0.5 µL Ribonuclease H (RNase H, 10 U/µL, Ambion AM2292) and incubated at 37° C. for 30 minUtes. 0.5 µL of RNase H treated sample was then combined with 5 µL 10× AmpliTaq® Buffer I (Applied Biosystems N8080171), 4 µL dNTP (2.5 mM), 0.5 µL 5' primer and 0.5 µL 3' primer (50 µM each), 1 µL of AmpliTaq® DNA polymerase (5 U/µL, Applied Biosystems N8080171) and 38.5 µL of RNase-free water. PCR was performed using 16 cycles of 30 seconds at 95° C., 30 seconds at 62° C. and 30 seconds at 72° C. Five (5) µL of PCR products were loaded on a 10% native PAGE gel and visualized by SYBR® Gold (Invitrogen 11494) staining. As shown by FIG. 13A, note that the placenta sample is fairly rich in small RNAs and the method presented herein is capable of producing small RNA products from ≤25 ng total RNA. In contrast, the mouse liver sample as shown by FIG. 13B is very poor in small RNAs by comparison and thus, according to certain embodiments of the current teachings, enrichment of such samples may provide better results.

Sequences for the adaptor Mix A are as for SEQ ID NO:1- SEQ ID NO:4 of Example 1.

EXAMPLE 8

Real-time PCR Demonstrates Dynamic Range of Small RNA Library Construction

Four synthetic RNA oligonucleotides containing 5'-PO4 (spike in controls, SIC; sequences shown below) were mixed at varying concentration spanning a 1000-fold input range (1000, 100, 10, and 1 pg in 1000× mix), and the mixture was serially diluted to 1×. Mixtures were spiked into 500 ng placenta total RNA as background (FIG. 14, FIG. 16A) and the ligation reaction was performed on the four samples as described previously except that the ligation reaction composition was incubated for two hours (instead of sixteen hours) at 16° C.

The samples were then treated with RNase H as described above and 0.5 µL of RNase H treated sample was then combined with 5 µL 10× AmpliTaq® Buffer I (Applied Biosystems N8080171), 4 µL dNTP (2.5 mM), 0.5 µL 5' primer and 0.5 µL 3' primer (50 µM each), 1 µL of AmpliTaq® DNA polymerase (5 U/µL, Applied Biosystems N8080171) and 38.5 µL of RNase-free water. PCR was performed using 15 cycles of 30 seconds at 95° C., 30 seconds at 62° C. and 30 seconds at 72° C. Following PCR cleanup by Qiagen PCR purification kit (Qiagen 28104), samples were eluted in 30 µL water and further diluted in a 1:400 ratio. Two µL diluted sample was then combined with 12.5 µL 2×SYBR® Green PCR Master Mix (Applied Biosystems 4309155), 1 ul primer mix (1 µM each) and 9.5 µL water (schematically shown in FIG. 15). Real-Time PCR was performed on an ABI 7500 Real-Time PCR System (Applied Biosystems 4351104) using 95° C. for 10 minutes, 40 cycles of 15 seconds at 95° C. and 1 minute at 68° C., followed by 15 seconds at 95° C., 1 minutes at 60° C. and 15 seconds at 95° C.

Cycle threshold values (Cts) for each target sequence (FIG. 16A, y-axis: Mean Ct) were plotted against log 10 values representing the four sample inputs (x-axis: log (mix concentration) 1000× to 1×, FIG. 16A). As seen in FIG. 16B, Cts for two endogenous miRNA control sequences in the background RNA (miR-16 and miR-21) were fairly constant across samples.

The four synthetic RNA oligonucleotides used in this example as "spike in controls" (SIC) were: (1) SIC 8: 5'-Phos GCGAAUUAAUGAAAGUGGGCA (SEQ ID NO:11; data shown using triangles in FIG. 16A); (2) SIC 34: 5'-Phos ACCCGACAUUAAAGGUGGCAU (SEQ ID NO:12; data shown using circles in FIG. 16A); (3) SIC 36: 5'-Phos CUCA-CAUUUCGGAACUGAUGC (SEQ ID NO:13; data shown using diamonds in FIG. 16A); and (4) SIC 37: 5'-Phos ACG-GACCUCGAACUUCACCCA (SEQ ID NO:14; data shown using squares in FIG. 16A). Therefore, the spike-in-control assays demonstrate an ability of the present methods to detect small RNA in a dynamic range spanning at least 1000-fold.

EXAMPLE 9

One-Step RT-PCR

The present example provides an exemplary method for generating amplification templates and amplified products, wherein the RNA-directed DNA Polymerase and DNA-directed DNA Polymerase are in the Reverse Transcription Reaction Composition.

Following the ligation reaction a mixture containing appropriate buffer, dNTPs, ArrayScript™ reverse transcriptase, AmpliTaq® DNA polymerase and both forward and reverse PCR primers are added directly to the ligation reaction and mixed by gentle pipetting up and down several times (3-4×). The reaction mixture is then incubated at 42° C. for 30 minutes in a thermal cycler to permit reverse transcription to generate an amplification template. RNase H is then added to the reaction mixture and incubated at 37° C. for 30 minutes in a thermal cycler. The reaction temperature is then ramped up to 95° C. and held for 5 minutes followed by standard amplification cycles, i.e., 30 seconds at 62° C. and 30 seconds at 72° C., as described in Example 1 to generate amplified products.

EXAMPLE 10

Generating Amplification Templates and Amplified Products with One DNA Polymerase Following the ligation reaction a mixture containing appropriate buffer (containing optimized concentrations of both manganese and magnesium), dNTPs, a DNA polymerase comprising both DNA dependent DNA polymerase activity and RNA dependent DNA polymerase activity and both forward and reverse PCR primers is added to the ligation reaction composition and mixed by gentle pipetting up and down several times (3-4×) to from a reverse transcription composition. The reverse transcription composition is incubated at 42° C. for 30 minutes in a thermal cycler to permit the reverse transcriptase activity to generate an amplification template. RNase H is then added to the reaction mixture and incubated at 37° C. for 30 minutes in a thermal cycler. The reaction temperature is then ramped up to 95° C. and held for 5 minutes followed by standard amplification cycles, i.e., 30 seconds at 62° C. and 30 seconds at 72° C., as described in Example 1 to generate amplified products.

EXAMPLE 11

Exemplary Method for Generating a Small RNA Library

The present example provides exemplary methods for generating a small RNA library as depicted in FIG. 17. When the RNA molecule of interest is a small RNA, the starting material should comprise the small RNA fraction. FirstChoice® prepared Total RNA (Applied Biosystems) is certified to contain miRNA and other small RNAs. Alternatively, total RNA that includes the small RNA fraction of a sample may be obtained using the mirVana™ miRNA Isolation Kit or mirVana™ PARIS™ Kit according to user's manual following the procedures for total RNA isolation.

Since RNA samples can vary widely in small RNA content based on their source and the RNA isolation method, evaluating the small RNA content of samples to determine whether to use total RNA or size-selected RNA in reactions may be desirable, using for example, but not limited to, an Agilent bioanalyzer with the Small RNA Chip.

Total RNA samples that contain more than 0.5% small RNA (in the ~10-40 nt size range) can be used without size-selection. When total RNA is used in the procedure the resulting reaction products will be a larger size range than those produced from PAGE-purified small RNA samples. In addition, SOLiD™ sequencing results from total RNA samples will typically include a slightly higher number of rRNA and tRNA reads.

RNA samples that contain less than 0.5% small RNA content should be enriched for the ~18-40 nt RNA fraction, for example but not limited to, by PAGE and elution, by the flashPAGE™ Fractionator and flashPAGE™ Reaction Clean-Up Kit (Applied Biosystems).

The relative amount of small RNA in different sample types varies greatly as described in Example 7. For example, RNA from tissue samples typically has a rich supply of small RNAs, whereas RNA from cultured cell lines often has very few small RNAs.

Recommended input RNA quantities include:

| RNA Source | Amount |
| --- | --- |
| Total RNA isolated from tissue | 10-500 ng |
| Total RNA isolated from cultured cells | 100-500 ng |
| Small RNA size-selected using PAGE | 1-200 ng |
| Control RNA (human placenta total RNA) | 100 ng |

Hybridization and Ligation: Hybridization and Ligation are carried out as follows. An adaptor mix A is designed for SOLiD™ sequencing from the 5' ends of small RNAs, for example, and an adaptor mix B is designed for SOLiD™ sequencing from the 3' ends. To sequence the small RNA in a sample from both the 5' and 3' ends, two ligations were set up, one with each adaptor mix. Each adaptor mix contains first, second, third and fourth oligonucleotides. Adaptor mix B is in the reverse complement orientation as compared to adaptor mix A so that each strand of an amplified product can be detected. On ice, the hybridization mix is prepared in 0.2 mL PCR tubes as follows.

Hybridization Mixture (8 µL Total Volume)

| Amount | Component |
| --- | --- |
| 2 µL | Adaptor Mix A or B |
| 3 µL | Hybridization Solution |
| 1-3 µL | RNA sample (1-500 ng) |
| to 8 µL | Nuclease-free Water |

The contents were mixed well by gently pipetting up and down a few times, then centrifuged briefly to collect the solution at the bottom of the tube. The reactions were placed in a thermal cycler with a heated lid, programmed as follows.

Adaptor Hybridization Incubation

| Temperature | Time |
| --- | --- |
| 65° C. | 10 min |
| 16° C. | hold |

The sample was incubated at 16° C. for 5 minutes. Maintaining the reaction(s) at 16° C., add the RNA ligation reagents to each sample in the order shown.

Ligation Reaction Mix (20 µL Final Volume)

| Amount | Component (add in order shown) |
| --- | --- |
| 10 µL | 2X Ligation Buffer |
| 2 µL | Ligation Enzyme Mix |

The mix was incubated for 16 hours in a thermal cycler set to 16° C. A 2 hour incubation is generally sufficient for ligation, however, an overnight incubation resulted in slightly higher amounts of ligated product.

Reverse Transcription and RNase H Digestion: The sample(s) were placed on ice and a Reverse Transcription (RT) Master Mix was prepared on ice by combining the following reagents. An extra 5-10% volume was included in the master mix to compensate for pipetting errors.

RT Master Mix (20 µL Per Sample)

| Amount | Component |
| --- | --- |
| 13 µL | Nuclease-free Water |
| 4 µL | 10X RT Buffe |
| 2 µL | dNTPs |
| 1 µL | ArrayScript Reverse Transcriptase |
| 20 µL | Total volume per reaction |

RT Master Mix (20 µL) was added to each sample and the samples were vortexed gently to mix thoroughly and microcentrifuged briefly to collect the mixture at the bottom of the tube. The samples were then incubated at 42° C. for 30 minutes to synthesize cDNA.

The cDNA can be stored at −20 C for a few weeks, at −80° C. for long term storage, or used immediately in the RNase H digestion (next).

RNase H incubation was carried out as follows. A volume (10 µL) of the RT reaction mixture was transferred from the previous step (cDNA) to a fresh tube. RNase H (1 µL) was added. The mixture was vortexed gently to mix, microcentrifuged briefly to collect the mixture at the bottom of the tube, and incubated at 37° C. for 30 minutes.

After the RNase H treatment, samples can be stored at −20° C. overnight or used immediately in the PCR.

Small RNA Library Amplification: Pilot and Large Scale PCRs: Because different sample types can contain substantially different amounts of small RNA, the number of PCR cycles needed to obtain enough DNA for SOLiD™ sequencing also varies. A 50 µL trial PCR was performed to determine the number of PCR cycles needed for a given sample type before proceeding to a set of three or more replicate 100 µL reactions (Large Scale PCRs) used to synthesize template for the next step in SOLiD™ sequencing sample preparation.

Most samples should be amplified for 12-15 cycles. For pilot experiments, 12 PCR cycles are recommended for samples from starting material with a relatively high amount of small RNA (i.e., total RNA from tissue of ~200-500 ng, or ~50-200 ng size-selected small RNA) and 15 cycles for those with relatively little small RNA (i.e., total RNA from tissue of ~1-200 ng, or total RNA from cultured cells of ~100-500 ng, or 1-50 ng size-selected small RNA.

Small RNA PCR Primer Sets: Ten different PCR primer sets for synthesis of SOLiD™ sequencing template are provided with the SOLiD™ Small RNA Expression Kit (Applied Biosystems). The primer sets are identical except for a 6 bp barcode located near the middle of the primers. This barcode feature of the PCR primers enables sequencing and analysis of multiplexed samples. That is, it is possible to sequence up to ten different samples, one amplified with each of the supplied SOLiD™ Small RNA PCR Primer Sets, in a single SOLiD™ sequencing reaction. Any of the primer sets can be used but samples are not mixed at this point.

Exemplary PCR primers include without limitation the forward primer and barcoded reverse primers shown below (individual barcode sequences are underlined).

```
Forward Primer (SEQ ID NO: 5):
5'-CCACTACGCCTCCGCTTTCCTCTCTATGGGCAGTCGGTGAT-3'

Reverse Primer BC1 (SEQ ID NO: 15):
5'-CTGCCCCGGGTTCCTCATTCTCTAAGCCCCTGCTGTACGGCCAA
GGCG-3'

Reverse Primer BC2 (SEQ ID NO: 16):
5'-CTGCCCCGGGTTCCTCATTCTCTCACACCCTGCTGTACGGCCAA
GGCG-3'
```

```
Reverse Primer BC3 (SEQ ID NO: 17):
5'-CTGCCCCGGGTTCCTCATTCTCTCCCCTTCTGCTGTACGGCCAA
GGCG-3'

Reverse Primer BC4 (SEQ ID NO: 18):
5'-CTGCCCCGGGTTCCTCATTCTCTCATCGGCTGCTGTACGGCCAA
GGCG-3'

Reverse Primer BC5 (SEQ ID NO: 19):
5'-CTGCCCCGGGTTCCTCATTCTCTTCGTTGCTGCTGTACGGCCAA
GGCG-3'

Reverse Primer BC6 (SEQ ID NO: 20):
5'-CTGCCCCGGGTTCCTCATTCTCTGGGCACCTGCTGTACGGCCAA
GGCG-3'

Reverse Primer BC7 (SEQ ID NO: 6):
5'-CTGCCCCGGGTTCCTCATTCTCTCCAGACCTGCTGTACGGCCAA
GGCG-3'

Reverse Primer BC8 (SEQ ID NO: 21):
5'-CTGCCCCGGGTTCCTCATTCTCTCTCCGTCTGCTGTACGGCCAA
GGCG-3'

Reverse Primer BC9 (SEQ ID NO: 22):
5'-CTGCCCCGGGTTCCTCATTCTCTCCCTTCCTGCTGTACGGCCAA
GGCG-3'

Reverse Primer BC10 (SEQ ID NO: 23):
5'-CTGCCCCGGGTTCCTCATTCTCTGCGGTCCTGCTGTACGGCCAA
GGCG-3'
```

A PCR Master Mix was prepared on ice by combining reagents as follows for a single 50 µL Trial PCR or a 100 µL Large Scale PCR.

PCR Master Mix (for a Single Reaction)

| Trial PCR (50 µL) | Large Scale PCR (100 µL) | Component |
|---|---|---|
| 38.9 µL | 77.8 µL | Nuclease-free Water |
| 5 µL | 10 µL | 10X PCR Buffer I |
| 1 µL | 2 µL | SOLID Small RNA PCR Primer Set (one set) |
| 4 µL | 8 µL | 2.5 mM dNTP Mix |
| 0.6 µL | 1.2 µL | AmpliTaq ® DNA Polymerase |
| 49.5 µL | 99 µL | Total volume per reaction |

The mix was vortexed gently to mix thoroughly and microcentrifuged briefly to collect the mixture at the bottom of the tube. (Once the appropriate number of PCR cycles for the sample type was determined, 3 or more replicate large scale PCRs are run for each sample. Reaction products are pooled to generate enough material for gel purification and subsequent SOLiD™ sequencing sample preparation.)

PCR Master Mix for a single reaction was pipetted into wells of a PCR plate or 0.2 mL PCR tubes. For a trial PCR (50 µL), 0.5 µL RNase H-treated cDNA was added to each aliquot of PCR Master Mix. For large scale PCR (100 µL), 1 µL RNase H-treated cDNA was added to each aliquot of PCR Master Mix. Greater than 1 µL cDNA in a 50 µL PCR is not recommended due to possible reaction inhibition.

Sample(s) were placed in a thermal cycler with a heated lid and the thermal profile shown below was carried out.

PCR Cycling Conditions

| | Stage | Reps | Temp | Time |
|---|---|---|---|---|
| Denaturation (hold) | 1 | 1 | 95° C. | 5 min |
| PCR (cycle) | 2 | 12-15 | 95° C. | 30 sec |
| | | | 62° C. | 30 sec |
| | | | 72° C. | 30 sec |
| Final Extension | 3 | 1 | 72° C. | 7 min |

PCR product (5-10 µL) was run on a native 6% polyacrylamide gel and the gel is stained with SYBR® Gold following the manufacturer's instructions.

FIG. 5 shows results from reactions that were amplified using an appropriate number of PCR cycles. Results are discussed in Example 1 and generalized here for illustration.

The amplified product derived from small RNA migrates at ~108-130 bp (the total length of the primers is ~89 bp, therefore, RNA of about 19-41 bp migrate in the cited range).

Note that higher molecular weight bands at approximately 150 and 200 bp are expected from reactions using total RNA as input, whereas these larger products are not expected from reactions using size-selected small RNA as input (see FIG. 5).

Self-ligated adaptors and their amplified products form a band at 89 bp. This band is typically present in all reactions. Further by-products migrate at ~100 bp. Underamplified samples exhibit very little material in the ~108-130 bp size range. Conversely, overamplified samples typically show a significant amount of material in the ~108-130 bp size range, plus a smear of reaction products larger than ~140-150 bp. Overamplified samples from total RNA input may also have a higher molecular weight ladder of bands that represent concatenated PCR products.

Amplified Small RNA Library Cleanup: The PCR products derived from small RNA were then cut from the gel, eluted out of the acrylamide, purified, and concentrated as follows. Samples were not heated at any step of this purification so that the DNA duplexes remain annealed and migrate according to their size during subsequent gel purification.

An equal volume of phenol/chloroform/isoamyl alcohol (25:24:1, pH 7.9) was added to each sample. Samples were vortexed to mix, then centrifuged at 13,000×g for 5 min at room temperature. The aqueous (upper) phase was transferred to a fresh 1.5 mL tube, with the volume measured during transfer. An equal volume of 5 M ammonium acetate was added to each sample. An amount (1/100 volume) of glycogen and 0.7 volume isopropanol were added (the sample volume after addition of ammonium acetate is used as a baseline). The mixture was mixed thoroughly, incubated at room temperature for 5 minutes, and centrifuged at 13,000×g for 20 minutes at room temperature. The supernatant was carefully removed and discarded. The DNA pellet was washed 3 times with 1 mL of 70% ethanol each time and allowed to air dry for ~15 minutes or until visible droplets of ethanol had evaporated.

PAGE gels were prepared, e.g., 0.75 mm, native TBE, 6% polyacrylamide gel. The size of the gel is not important; minigels (~60-100 cm2) are typically the most convenient. Gels cast in-house within a few hours of use provide better resolution than purchased pre-cast gels. PAGE elution buffer is also prepared. For example, for 10 mL elution buffer, 5 mL of TE Buffer pH 8 (10 mM Tris-HCl, pH 8, 1 mM EDTA) is combined with 5 mL of 5 M Ammonium acetate (2.5 M final conc); ~450 µL is needed for each sample.

A needle (e.g., 21-gauge) was used to poke a hole through the bottom-center of 0.5 mL microcentrifuge tube for each sample. The gel pieces excised above were placed in these tubes, and the centrifugation in the subsequent step shred the DNA-containing gel pieces for elution of the DNA. The DNA pellet from above in 20 µL 1× nondenaturing gel loading buffer was loaded onto a 6% native TBE polyacrylamide gel. A DNA Ladder, or a similar ladder, was loaded in a separate lane as a marker. The gel was run at ~140 V (~30 minutes for a minigel) or until the leading dye front almost exits the gel and stained with SYBR® Gold following the manufacturer's instructions. The gel piece containing 105-150 bp DNA was excised using a clean razor blade and placed in a 0.5 mL tube prepared with a hole in the bottom, the 0.5 mL tube placed within a larger 1.5 mL tube. The gel piece was shredded by microcentrifuging for 3 min at 13,000×g. An amount (200 µL) PAGE elution buffer was added to the shredded gel pieces; the mixture incubated at room temperature for 1 hour, and the buffer was transferred to a fresh tube, leaving the gel fragments behind. The shredded gel pieces were extracted again, this time at 37° C. and the elution buffers were combined. Transfer the mixture to a Spin Column and centrifuged at top speed for 5 minutes to remove gel pieces. The DNA was in the flow-through.

An amount (1/100 volume) of glycogen and 0.7 volume isopropanol were added to each sample. The samples were mixed thoroughly, incubated at room temperature for 5 minutes, and centrifuged at 13,000×g for 20 min at room temperature. The supernatant was carefully removed and discarded and the pellet was air dried, then resuspended in 20 µL nuclease-free water.

DNA in each sample was quantitated by measuring the $A_{260}$ in a spectrophotometer (1 $A_{260}$=50 µg DNA/mL) and verifying the size and quality using an Agilent bioanalyzer or 6% native PAGE. The minimum amount of DNA that can be used for SOLiD™ sequencing is 200 ng at 20 ng/L, but more DNA is preferable. SOLiD™ Small RNA Expression Kit reaction products enter the SOLiD™ sample preparation workflow at the "SOLiD™ System Template Bead Preparation" stage, in which emulsion PCR is used to attach molecules to beads. SOLiD™ sequencing and emulsion PCR is described, for example, in published PCT applications WO 06/084132 entitled "Reagents, Methods, and Libraries For Bead-Based Sequencing and WO 07/121489 entitled "Reagents, Methods, and Libraries for Gel-Free Bead-Based Sequencing."

EXAMPLE 12

Validation of Present Methods for Mapping and Transcript Coverage

The present example provides for validation of present methods by demonstrating that the methods are useful for mapping short (25-70 base) tags of sequences to the human genome or other databases and provides uniform transcript coverage.

For example, at least 15 libraries testing different conditions were separately made, pooled and then sequenced in a single run. A relatively equal number of miRNA sequences were found across the libraries; any deviations from equal numbers detected likely represent pipetting errors in the pooling step. In a single sample, 389 out of 555 miRNAs were detected (70%). Undetected miRNAs predominantly represent RNA molecules that are not present in the sample.

Sequence reads cs.fasta files generated on the SOLiD™ instrument were mapped to databases of miRNAs, tRNAs, rRNAs, Refseqs and the genome. Out of 17.7 million reads, 55% were mapped to the genome, 12% to RefSeq sequences, 1% to rRNA, 0.5% to tRNA, 8.25% to miRNA and 23% were not mapped. Reads that mapped to the genome uniquely were found to be clustered, i.e., ~3000 have at least two reads and a size of <70 bases. These sequences are candidates for novel miRNAs or ncRNAs.

An analysis of transcriptome sequencing using the SOLiD™ System of fifteen barcoded and pooled libraries found that, out of about 59.16 million reads, 36.22% were mapped to the genome, 6.98% to RefSeq sequences, 0.32% to rRNA, and 0.01% to tRNA.

RNA detection was demonstrated to be reproducible. Placenta poly(A) RNase III fragmented libraries generated under similar but not identical conditions were found to have good reproducibility (R2 values of 0.97) and a dynamic range of detection spanning at least 5 logs.

A whole transcript analysis was carried out using the SOLiD™ System and the coverage for mRNA to brain-specific angiogenesis inhibitor 2 (BAI2) was found to be uniform from 5' to 3'. Overlapping individual 50 base tags representing nearly the entire length of the mRNA were observed. Specific tags represented multiple times can be a reflection of the relative amount of the mRNA contained within the sample (that is, the more RNA molecules present in the sample the higher the probability of capturing the same tag of sequence), bias in the cleavage site of the fragmented RNA, or possibly PCR amplification artifacts.

The density of starting points for sequencing tags was plotted relative to the length of the RNA transcripts analyzed. The results indicated that tag density is uniform across the body of the transcripts and there is a drop off at the extreme 5' and 3' ends. This decrease in capture tags at the ends of the RNA represent the inefficiency of ligating to the 5' cap contained on all RNA polymerase II generated RNA transcripts. Regarding the 3' end of mRNAs that typically contain a polyA tail, the ability to capture and amplify this material appears hindered and the proportion of tags is low, possibly due to the homopolymer nature of the tail.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

The invention claimed is:

1. A method for detecting an RNA molecule, comprising:
   (a) forming a single ligation reaction mixture containing (i) at least one RNA molecule including at least a first and a second RNA molecule, (ii) a plurality of a first double-stranded nucleic acid adaptor, (iii) a plurality of a second double-stranded nucleic acid adaptor, and (iv) an RNA ligase, wherein a first strand of the first double-stranded nucleic acid adaptors of the plurality include at least two ribonucleosides at the 3' end, and a second strand of the first double-stranded nucleic acid adaptors of the plurality include a first single-stranded portion at the 5' end, and wherein a first strand of the second double-stranded nucleic acid adaptors of the plurality include a terminal 5' phosphate group, and a second strand of the second double-stranded nucleic acid adaptors of the plurality include a second single-stranded portion at the 3' end, and wherein the first and the second single-stranded portions contain a nucleotide sequence that hybridizes to a portion of the at least first RNA molecule from the mixture of different RNA molecules, and wherein the first double-stranded adaptors of the plurality, or the second double-stranded adaptors of the plurality, or the first and second double-stranded adaptors comprise a unique bar code sequence; and
   (b) producing a plurality of different RNA ligation product by ligating the first double-stranded adaptor to a first end of the at least one RNA molecule and ligating the second double-stranded adaptor to a second end of the at least one RNA molecule.

2. The method of claim 1 further comprising:
   (a) producing a first strand cDNA product by reverse transcribing the at least one RNA ligation product;
   (b) producing a plurality of amplification products by amplifying the first strand cDNA product; and
   (c) detecting at least one amplification product.

3. The method of claim 1, wherein the RNA ligase comprises an Rnl2 family ligase.

4. The method of claim 3, wherein the RNA ligase comprises bacteriophage T4 RNA ligase 2 (Rnl2).

5. The method of claim 1, wherein the first single-stranded portion of the first double-stranded adaptors of the plurality and the second single-stranded portion of the second double-stranded adaptors of the plurality, comprise degenerate sequences.

6. The method of claim 1, wherein the amplifying in step (b) comprises PCR amplifying with at least one forward amplification primer and at least one reverse amplification primer.

7. The method of claim 6, wherein the at least one forward amplification primer or the at least one reverse amplification primer includes a unique identification sequence.

8. The method of claim 1, wherein the RNA molecule is a small non-coding RNA or an RNA fragment.

9. The method of claim 1, wherein the first strand of the first double-stranded adaptor and the first strand of the second double-stranded adaptor comprise different nucleotide sequences.

10. The method of claim 1, wherein the first single-stranded portions of the plurality of first double-stranded nucleic acid adaptors contain different sequences, and wherein the second single-stranded portions of the plurality of second double-stranded nucleic acid adaptors contain different sequences.

11. The method of claim 2, wherein the detecting comprises sequencing the plurality of amplification product.

12. The method of claim 1, wherein the first single-stranded portion or the second single-stranded portion, or the first single-stranded portion and the second single-stranded portion comprise a sequence-specific region to selectively hybridize with the portion of the RNA molecule.

13. The method of claim 1, wherein first single-stranded portion of the first double-stranded adaptors of the plurality and the second single-stranded portion of the second double-stranded adaptors of the plurality, comprises adenosine, guanosine, cytidine, and thymidine.

14. The method of claim 2, wherein the reverse transcribing of step (a) comprises contacting the at least one RNA ligation product with triphosphate nucleotides, and (i) an RNA-dependent DNA polymerase, (ii) a DNA polymerase having DNA-dependent DNA polymerase activity and RNA-dependent DNA polymerase activity, or (iii) an RNA-dependent DNA polymerase and a DNA-dependent DNA polymerase.

15. The method of claim 2, wherein the amplifying in step (b) comprises contacting the first strand cDNA product with triphosphate nucleotides, at least one forward amplification primer, at least one reverse amplification primer and a DNA-dependent DNA polymerase.

16. The method of claim 1, wherein at least one of the at least one first double-stranded adaptor or at least one second double-stranded adaptor comprises an identification sequence.

* * * * *

SEQUENCE LISTING

<160> NUMBER OF SEQ ID NOS: 23

<210> SEQ ID NO 1
<211> LENGTH: 23

```
<212> TYPE: RNA
<213> ORGANISM: Artificial Sequence
<220> FEATURE:
<223> OTHER INFORMATION: Synthetic DNA/RNA

<400> SEQUENCE: 1
ccucucuaug ggcagucggu gau                                       23

<210> SEQ ID NO 2
<211> LENGTH: 29
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (1)..(6)
<223> OTHER INFORMATION: N is A, C, G, or T/U

<400> SEQUENCE: 2
nnnnnnatca ccgactgccc atagagagg                                 29

<210> SEQ ID NO 3
<211> LENGTH: 19
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (1)..(1)
<223> OTHER INFORMATION: 5'-phosphate

<400> SEQUENCE: 3
cgccttggcc gtacagcag                                            19

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (20)..(25)
<223> OTHER INFORMATION: N is A, C, G, or T/U

<400> SEQUENCE: 4
ctgctgtacg gccaaggcgn nnnnn                                     25

<210> SEQ ID NO 5
<211> LENGTH: 41
<212> TYPE: DNA
<213> ORGANISM: Artificial Sequence
<220> FEATURE:
<223> OTHER INFORMATION: primer_bind

<400> SEQUENCE: 5
ccactacgcc tccgctttcc tctctatggg cagtcggtga t                   41

<210> SEQ ID NO 6
<211> LENGTH: 48
<212> TYPE: DNA
<213> ORGANISM: Artificial Sequence
<220> FEATURE:
<223> OTHER INFORMATION: primer_bind

<400> SEQUENCE: 6
```

```
ctgccccggg ttcctcattc tctccagacc tgctgtacgg ccaaggcg                         48
```

<210> SEQ ID NO 7
<211> LENGTH: 27
<212> TYPE: RNA
<213> ORGANISM: Artificial Sequence
<220> FEATURE:
<223> OTHER INFORMATION: Synthetic DNA/RNA

<400> SEQUENCE: 7

```
cucgagaauu aacccucacu aaaggga                                                27
```

<210> SEQ ID NO 8
<211> LENGTH: 35
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (1)..(8)
<223> OTHER INFORMATION: N is A, C, G, or T/U

<400> SEQUENCE: 8

```
nnnnnnnntc cctttagtga gggttaattc tcgag                                       35
```

<210> SEQ ID NO 9
<211> LENGTH: 28
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (1)..(1)
<223> OTHER INFORMATION: 5'-phosphate

<400> SEQUENCE: 9

```
tccctatagt gagtcgtatt acgaattc                                               28
```

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (29)..(36)
<223> OTHER INFORMATION: N is A, C, G, or T/U

<400> SEQUENCE: 10

```
gaattcgtaa tacgactcac tatagggann nnnnnn                                      36
```

<210> SEQ ID NO 11
<211> LENGTH: 21
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<222> LOCATION: (1)..(1)
<223> OTHER INFORMATION: 5'-phosphate

<400> SEQUENCE: 11

```
gcgaauuaau gaaagugggc a                                                      21
```

```
<210> SEQ ID NO 12
<211> LENGTH: 21
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<222> LOCATION: (1)..(1)
<223> OTHER INFORMATION: 5'-phosphate

<400> SEQUENCE: 12
acccgacauu aaagguggca u                                             21

<210> SEQ ID NO 13
<211> LENGTH: 21
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<222> LOCATION: (1)..(1)
<223> OTHER INFORMATION: 5'-phosphate

<400> SEQUENCE: 13
cucacauuuc ggaacugaug c                                             21

<210> SEQ ID NO 14
<211> LENGTH: 21
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<222> LOCATION: (1)..(1)
<223> OTHER INFORMATION: 5'-phosphate

<400> SEQUENCE: 14
acggaccucg aacuucaccc a                                             21

<210> SEQ ID NO 15
<211> LENGTH: 48
<212> TYPE: DNA
<213> ORGANISM: Artificial Sequence
<220> FEATURE:
<223> OTHER INFORMATION: primer_bind

<400> SEQUENCE: 15
ctgccccggg ttcctcattc tctaagcccc tgctgtacgg ccaaggcg                48

<210> SEQ ID NO 16
<211> LENGTH: 48
<212> TYPE: DNA
<213> ORGANISM: Artificial Sequence
<220> FEATURE:
<223> OTHER INFORMATION: primer_bind

<400> SEQUENCE: 16
ctgccccggg ttcctcattc tctcacaccc tgctgtacgg ccaaggcg                48

<210> SEQ ID NO 17
<211> LENGTH: 48
<212> TYPE: DNA
<213> ORGANISM: Artificial Sequence
<220> FEATURE:
<223> OTHER INFORMATION: primer_bind
```

```
<400> SEQUENCE: 17
ctgccccggg ttcctcattc tctccccttc tgctgtacgg ccaaggcg                48

<210> SEQ ID NO 18
<211> LENGTH: 48
<212> TYPE: DNA
<213> ORGANISM: Artificial Sequence
<220> FEATURE:
<223> OTHER INFORMATION: primer_bind

<400> SEQUENCE: 18
ctgccccggg ttcctcattc tctcatcggc tgctgtacgg ccaaggcg                48

<210> SEQ ID NO 19
<211> LENGTH: 48
<212> TYPE: DNA
<213> ORGANISM: Artificial Sequence
<220> FEATURE:
<223> OTHER INFORMATION: primer_bind

<400> SEQUENCE: 19
ctgccccggg ttcctcattc tcttcgttgc tgctgtacgg ccaaggcg                48

<210> SEQ ID NO 20
<211> LENGTH: 48
<212> TYPE: DNA
<213> ORGANISM: Artificial Sequence
<220> FEATURE:
<223> OTHER INFORMATION: primer_bind

<400> SEQUENCE: 20
ctgccccggg ttcctcattc tctgggcacc tgctgtacgg ccaaggcg                48

<210> SEQ ID NO 21
<211> LENGTH: 48
<212> TYPE: DNA
<213> ORGANISM: Artificial Sequence
<220> FEATURE:
<223> OTHER INFORMATION: primer_bind

<400> SEQUENCE: 21
ctgccccggg ttcctcattc tctctccgtc tgctgtacgg ccaaggcg                48

<210> SEQ ID NO 22
<211> LENGTH: 48
<212> TYPE: DNA
<213> ORGANISM: Artificial Sequence
<220> FEATURE:
<223> OTHER INFORMATION: primer_bind

<400> SEQUENCE: 22
ctgccccggg ttcctcattc tctcccttcc tgctgtacgg ccaaggcg                48

<210> SEQ ID NO 23
<211> LENGTH: 48
<212> TYPE: DNA
<213> ORGANISM: Artificial Sequence
<220> FEATURE:
<223> OTHER INFORMATION: primer_bind

<400> SEQUENCE: 23
ctgccccggg ttcctcattc tctgcggtcc tgctgtacgg ccaaggcg                48
```